US010100027B2

(12) United States Patent
Zhang et al.

(10) Patent No.: US 10,100,027 B2
(45) Date of Patent: Oct. 16, 2018

(54) BENZOFURAN ANALOGUE AS NS4B INHIBITOR

(71) Applicants: CHANGZHOU YINSHENG PHARMACEUTICAL CO., LTD., Changzhou, Jiangsu (CN); SICHUAN UNIVERSITY, Chengdu, Sichuan (CN)

(72) Inventors: Yang Zhang, Shanghai (CN); Zhifei Fu, Shanghai (CN); Jianfei Wang, Shanghai (CN); Jian Li, Shanghai (CN); Shuhui Chen, Shanghai (CN); Yuquan Wei, Chengdu (CN); Luoting Yu, Chengdu (CN); Xin Tao, Jiangsu (CN)

(73) Assignees: CHANGZHOU YINSHENG PHARMACEUTICAL CO., LTD., Changzhou (CN); SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 15/514,389

(22) PCT Filed: Sep. 23, 2015

(86) PCT No.: PCT/CN2015/090335
§ 371 (c)(1),
(2) Date: May 9, 2017

(87) PCT Pub. No.: WO2016/045587
PCT Pub. Date: Mar. 31, 2016

(65) Prior Publication Data
US 2017/0240519 A1 Aug. 24, 2017

(30) Foreign Application Priority Data

Sep. 26, 2014 (CN) .......................... 2014 1 0504810

(51) Int. Cl.
*C07D 471/04* (2006.01)
*C07D 487/04* (2006.01)
*C07D 405/00* (2006.01)
*C07D 307/85* (2006.01)
*C07D 405/14* (2006.01)
*C07D 405/12* (2006.01)
*C07D 413/14* (2006.01)
*C07D 413/12* (2006.01)
*C07D 405/06* (2006.01)

(52) U.S. Cl.
CPC ......... *C07D 307/85* (2013.01); *C07D 405/06* (2013.01); *C07D 405/12* (2013.01); *C07D 405/14* (2013.01); *C07D 413/12* (2013.01); *C07D 413/14* (2013.01); *C07D 471/04* (2013.01)

(58) Field of Classification Search
CPC ... C07D 471/04; C07D 487/04; C07D 405/00
See application file for complete search history.

(56) References Cited

U.S. PATENT DOCUMENTS

| 4,221,793 | A | 9/1980 | Weber et al. |
| 8,071,797 | B2 | 12/2011 | Labadie et al. |
| 8,198,449 | B2 | 6/2012 | Pracitto et al. |
| 2003/0065179 | A1* | 4/2003 | Chu-Moyer .......... C04B 35/632 544/295 |
| 2010/0204265 | A1 | 8/2010 | Baskaran et al. |
| 2014/0147412 | A1 | 5/2014 | Zhang et al. |

FOREIGN PATENT DOCUMENTS

| CN | 102863428 A | 1/2013 |
| CN | 105732602 A | 7/2016 |
| EP | 1346987 A1 | 9/2003 |
| JP | 55500001 A | 1/1980 |
| JP | H11500123 A | 1/1999 |
| JP | 2002-541109 A | 12/2002 |
| JP | 2008-526755 A | 7/2008 |
| JP | 2009-538358 A | 11/2009 |
| JP | 2010-528114 A | 8/2010 |
| JP | 2010-535773 A | 11/2010 |
| JP | 2011-512341 A | 4/2011 |
| JP | 2012-502099 A | 1/2012 |
| WO | WO-7900426 A1 | 7/1979 |
| WO | WO-1996/25414 A1 | 8/1996 |
| WO | WO-2000/59510 A1 | 10/2000 |
| WO | WO-2002/053550 A1 | 7/2002 |
| WO | WO-2006/074025 A1 | 7/2006 |
| WO | WO-2007/140005 A2 | 12/2007 |
| WO | WO-2008/153752 A2 | 12/2008 |
| WO | WO-2009/023179 A2 | 2/2009 |
| WO | WO-2010091411 A1 | 8/2010 |
| WO | WO-2011041713 A2 | 4/2011 |
| WO | WO-2011050284 A1 | 4/2011 |
| WO | WO-2012122716 A1 | 9/2012 |
| WO | WO-2013095275 A1 | 6/2013 |

OTHER PUBLICATIONS

Miller, J.F. et al., "Hepatitis C Replication Inhibitors That Target the Viral NS4B Protein", Journal of Medicinal Chemistry, vol. 57, No. 5, Apr. 1, 2013 (Apr. 1, 2013).
Shotwell, J. B. et al., "Imidazo[1, 2-a]pyridines That Directly Interact with Hepatitis C NS4B: Initial Preclinical Characterization", ACS Medicinal Chemistry Letters, vol. 3, No. 7, May 24, 2012 (May 24, 2012).
International Search Report and Written Opinion of the ISA for PCT/CN2015/090335, ISA/CN, Beijing, dated Nov. 26, 2015.
Nov. 26, 2015 Written Opinion of the International Searching Authority issued in International Patent Application No. PCT/CN2015/090335.
Stephen M. Berge et al., "Pharmaceutical Salts", Journal of Pharmaceutical Science, vol. 66(1), pp. 1-19, 1977.
Hubert Maehr et al., "A Proposed Hew Convention for Graphic Presentation of Molecular Geometry and Topography", Journal of Chemical Education, vol. 62(2), pp. 114-120, 1985.

(Continued)

*Primary Examiner* — Bruck Kifle
(74) *Attorney, Agent, or Firm* — Harness, Dickey & Pierce, P.L.C.

(57) ABSTRACT

Provided is a benzofuran analog having a structure represented by formula (I) and used as an NS4B inhibitor, or a pharmaceutically acceptable salt of the benzofuran analog. The benzofuran analog has anti-hepatitis C virus activity.

7 Claims, No Drawings

(56) References Cited

OTHER PUBLICATIONS

Nov. 21, 2016 Chinese Office Action issued in Chinese Patent Application No. 201610070866.9.
Remington: The Science and Practice of Pharmacy, 21st Ed., Lippincott, Williams & Wilkins, 2005.
Notification of European publication number and information on the application of Article 67(3) EPC, PCT/CN2015090335 (2017).
Sep. 6, 2017 extended Search Report issued in International Patent Application No. PCT/CN2015/090335.
Vincent et al. "Design and synthesis of spirocyclic compounds as HCV replication inhibitors by targeting viral NS4B protein", vol. 24, 2014.
Jinyoung Kim et al. "Identification of Novel HCV RNA-dependent RNA polymerase Inhibitors Using Pharmacophore-Guided Virtural Screening", vol. 72, 2008.
The First Office Action dated Apr. 17, 2018 issued on counterpart Japanese Patent Application 2017-535953.

\* cited by examiner

BENZOFURAN ANALOGUE AS NS4B INHIBITOR

CROSS-REFERENCE TO RELATED APPLICATIONS

This application is a 371 U.S. National Stage of International Application No. PCT/CN2015/090335, filed on Sep. 23, 2015, which claims the benefit of and priority to Chinese Patent Application No. 2014105048100, filed on Sep. 26, 2014. The entire disclosures of the above applications are incorporated herein by reference.

FIELD OF INVENTION

The present invention relates to a novel class of benzofuran analogues as NS4B inhibitors, specifically relates to a compound having a structure of formula (I) or a pharmaceutically acceptable salt thereof.

PRIOR ARTS

HCV is one of the major human pathogens, it is estimated that there are about 0.17 billion chronic HCV infectors worldwide, which is 5 times the number of human immunodeficiency virus type-1 infectors. Chronic HCV infectors can develop into severe progressive liver diseases, including the liver cirrhosis and the hepatocellular carcinoma. Thus, the chronic HCV infection is the leading cause of death due to liver diseases in the world.

At present, the standard therapy of chronic HCV infection is through coadministration of α-interferon, ribavirin and a direct acting antiviral (DAA) drug, which is one of the drugs licensed in recent two years. Although the curative effect is significantly improved compared to the coadministration of α-interferon and ribavirin, the therapy is ineffective for some chronic HCV infectors and the virus can become drug resistance. In addition, α-interferon and ribavirin have obvious adverse reactions. Therefore, a novel and effective drug for chronic HCV infection treatment is urgently desirable.

HCV is a single-stranded RNA virus, which belongs to a separate genus of the flaviviridae family. All members in the flaviviridae family are enveloped virus particles containing the strand RNA genome, which encodes all known viral specific proteins through the translation of a single uninterrupted open-reading frame (ORF).

There are considerable heterogeneities among the nucleotides of the HCV genome and the encoded amino acid sequences. It has been identified that there are at least 6 major genotypes and more than 50 subtypes. The distribution of main HCV genotypes varies in the world. Despite of a large number of studies on the role of genotypes for the pathogenesis and treatment, the clinical importance of HCV genetic heterogeneity is still unclear.

The HCV RNA genome has about 9500 nucleotides, with a single open-reading frame, encoding a single polyprotein of about 3000 amino acids. In the infected cells, the polyprotein is cleaved by cellular proteases and viral proteases at multiple sites to provide the structural and non-structural (NS) protein. As far as HCV, the formation of mature non-structural protein (NS2, NS3, NS4A, NS4B, NS5A and NS5B) was achieved by two kind of viral proteases. It is generally believed that the first kind (NS2) is a metal protease, cleaving at the NS2-NS3 junction site; the second protease is a serine protease contained in the N-terminal region of NS3 (also called the NS3 protease herein), which mediates all subsequent NS3 downstream cleavages, a cis-cleavage at the NS3-NS4A junction site, and trans-cleavages at the NS4A-NS4B, NS4B-NS5A and NS5A-NA5B junction sites. NS4A protein appears to have a variety of functions, for example, being a cofactor of NS3 protease and possibly assisting NS3 and other viral to replicate enzyme components to carry out the membrane localization. The NS3 protein also shows nucleoside triphosphatase and RNA helicase activities. The functions of the two proteins NS4B and NS5A are not completely clear, but they play an important role in the replication of HCV. NS4B is a transmembrane protein participating in the formation of virus replication complex. NS5A is a phosphorylated protein participating in viral RNA replication and viral particle formation. NS5B (also known as HCV polymerase) is a RNA-dependent RNA polymerase participating in RNA replication of HCV genome.

WO2013095275, WO2012122716, CN102863428A and etc. respectively reported a series of compounds as HCV inhibitors, whose effects in the aspects of activity, solubility and so on need to be further improved.

CONTENT OF THE PRESENT INVENTION

The aim of the present invention is to provide a compound having a structure of formula (I) or a pharmaceutically acceptable salt thereof,

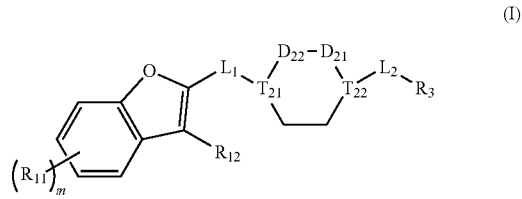

wherein,
the moiety

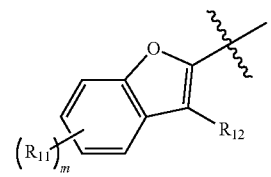

can be replaced by

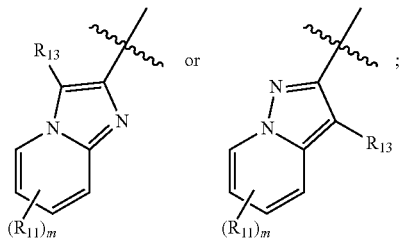

none, one or two of $T_{21-22}$ are selected from N, the rest of which are selected from $C(R_t)$;

each of $D_{21-22}$, $L_{1-2}$ is independently selected from the group consisting of $-[C(R_{d1})(R_{d2})]_{0-2}-$, $-C(=O)-$, —C(=O)N(R_{d3})—,  —N(R_{d4})—,  —C(=NR_{d5})—,  —S(=O)_2N(R_{d6})—,  —S(=O)N(R_{d7})—,  —O—,  —S—,  —C(=O)O—,  —C(=S)—,  —S(=O)—,  —S(=O)_2— and —N(R_{d8})C(=O)N(R_{d9})—;

m is selected from the group consisting of 1, 2, 3 and 4;

$R_3$ is selected from the group consisting of H, F, Cl, Br, I, CN, OH, SH, $NH_2$, CHO, COOH, C(=O)$NH_2$, S(=O)$NH_2$, S(=O)$_2NH_2$, or selected from the group, optionally substituted by none, one, two or three of $R_t$, consisting of a $C_{1-10}$ alkyl or heteroalkyl, a $C_{3-10}$ cyclohydrocarbyl or heterocyclohydrocarbyl, a $C_{1-10}$ alkyl or heteroalkyl substituted by a $C_{3-10}$ cyclohydrocarbyl or heterocyclohydrocarbyl;

each of $R_{11-13}$, $R_t$, $R_{d1}$, $R_{d2}$ is independently selected from the group consisting of H, F, Cl, Br, I, CN, OH, SH, $NH_2$, CHO, COOH, C(=O)$NH_2$, or selected from the group consisting of a $C_{1-10}$ alkyl or heteroalkyl optionally substituted by $R_{01}$, a $C_{3-10}$ cyclohydrocarbyl or heterocyclohydrocarbyl, a $C_{1-10}$ alkyl or heteroalkyl substituted by a $C_{3-10}$ cyclohydrocarbyl or heterocyclohydrocarbyl;

$R_{01}$ is selected from the group consisting of F, Cl, Br, I, CN, OH, SH, $NH_2$, and $R_{02}$;

$R_{02}$ is selected from the group consisting of a $C_{1-10}$ alkyl, a $C_{1-10}$ alkylamino, a N,N-bis($C_{1-10}$ alkyl)amino, a $C_{1-10}$ alkoxyl, a $C_{1-10}$ alkanoyl, a $C_{1-10}$ alkoxycarbonyl, a $C_{1-10}$ alkylsulfonyl, a $C_{1-10}$ alkylsulfinyl, a $C_{3-10}$ cycloalkyl, a $C_{3-10}$ cycloalkylamino, a $C_{3-10}$ heterocycloalkylamino, a $C_{3-10}$ cycloalkoxyl, a $C_{3-10}$ cycloalkanoyl, a $C_{3-10}$ cycloalkoxycarbonyl, a $C_{3-10}$ cycloalkylsulfonyl, and a $C_{3-10}$ cycloalkylsulfinyl;

the "hetero" represents a heteroatom or a heteroatomic group, which is selected from the group consisting of —C(=O)N(R_{d3})—,  —N(R_{d4})—,  —C(=NR_{d5})—,  —S(=O)_2N(R_{d6})—,  —S(=O)N(R_{d7})—,  —O—,  —S—,  —C(=O)O—,  —C(=O)—,  —C(=S)—,  —S(=O)—,  —S(=O)_2— and/or —N(R_{d8})C(=O)N(R_{d9})—;

each of $R_{d3-d9}$ is independently selected from the group consisting of H, OH, $NH_2$, and $R_{02}$;

$R_{02}$ is optionally substituted by $R_{001}$;

$R_{001}$ is selected from the group consisting of F, Cl, Br, I, CN, OH, N(CH_3)_2, NH(CH_3), $NH_2$, CHO, COOH, C(=O)$NH_2$, trihalomethyl, dihalomethyl, monohalomethyl, aminomethyl, hydroxymethyl, methyl, methylamino, formyl, methoxycarbonyl, methylsulfonyl, and methylsulfinyl;

the number of $R_{01}$, $R_{001}$, the heteroatom or the heteroatomic group is independently selected from the group consisting of 0, 1, 2 and 3;

optionally, there is another linking bond $(CH_2)_{1-3}$ between $T_{21}$ and $T_{22}$.

In some embodiments of the present invention, each of $D_{21-22}$, $L_{1-2}$ is independently selected from the group consisting of $(CH_2)_{0-2}$, —C(=O)—, —C(=O)NH—, and —C(=O)N(Me)-.

In some embodiments of the present invention, the moiety

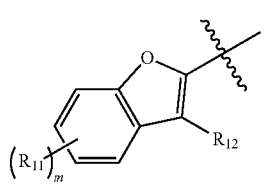

is selected from

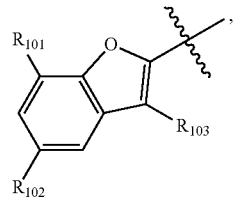

each of $R_{101-103}$ is independently selected from the group consisting of H, F, Cl, Br, I, CN, OH, SH, $NH_2$, CHO, COOH, C(=O)$NH_2$, or selected from the group, optionally substituted by none, one, two or three of $R_{01}$, consisting of a $C_{1-10}$ alkyl or heteroalkyl, a $C_{3-10}$ cyclohydrocarbyl or heterocyclohydrocarbyl, and a $C_{1-10}$ alkyl or heteroalkyl substituted by a $C_{3-10}$ cyclohydrocarbyl or heterocyclohydrocarbyl, $R_{01}$ is defined as claims.

In some embodiments of the present invention, each of $R_{101-103}$ is independently selected from the group consisting of F, Cl, Br, —$CF_3$, —$CHF_2$, CN, Me, ethyl, propyl, cyclopropyl and iso-propyl.

In some embodiments of the present invention, the moiety

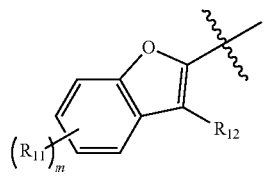

is selected from the group consisting of

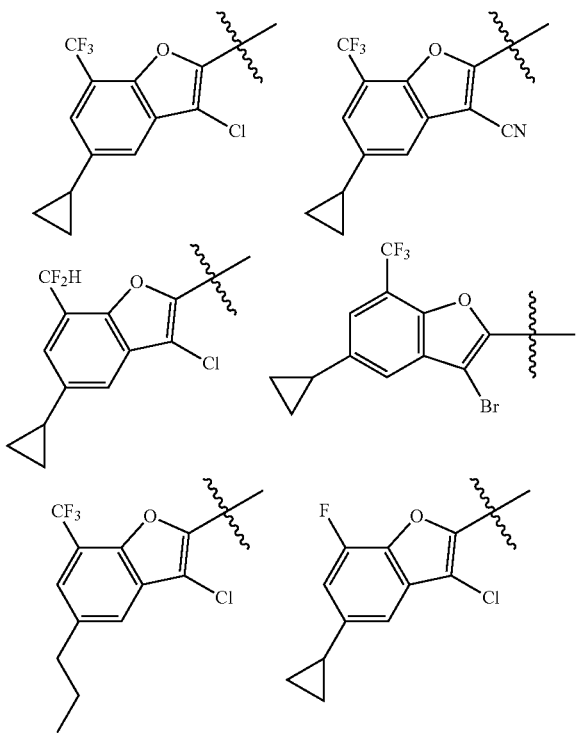

-continued

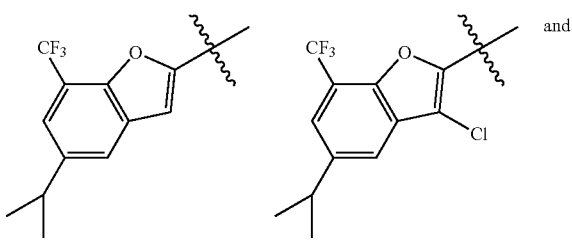

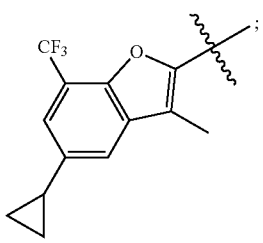

or the moiety is selected from

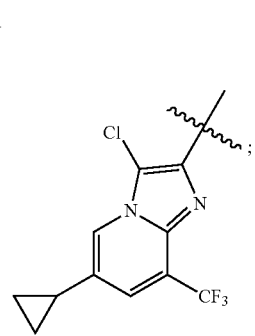 [SMILES: *c1nc2c(C(F)(F)F)cc(C3CC3)cn2c1Cl]

or the moiety

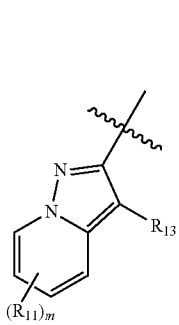

is selected from

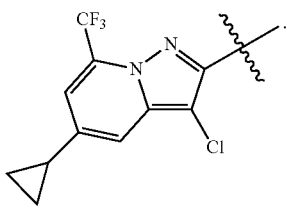 [SMILES: *c1nn2c(C(F)(F)F)cc(C3CC3)cc2c1Cl]

In some embodiments of the present invention, the moiety

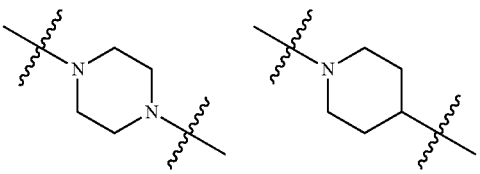

is selected from the group consisting of

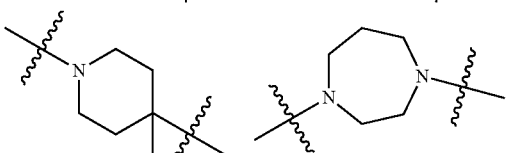

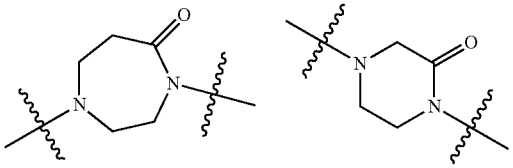

In some embodiments of the present invention, $R_3$ is selected from the group consisting of

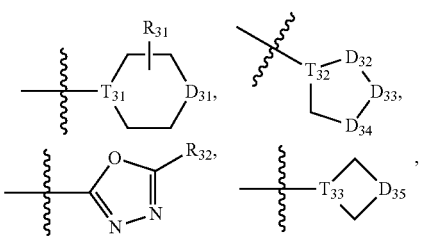

—$N(R_{33})(R_{34})$, and $O(R_{35})$, or selected from a $C_{1-3}$ alkyl, cyclopropyl, phenyl or pyridyl which is substituted by $R_{001}$, wherein, each of T$_{31-33}$ is dependently selected from the group consisting of N and C(R$_t$);

each of D$_{31-35}$ is dependently selected from the group consisting of —[C(R$_{d1}$)(R$_{d2}$)]$_{0-2}$—, —C(=O)—, —C(=O)N(R$_{d3}$)—, —N(R$_{d4}$)—, —C(=NR$_{d5}$)—, —S(=O)$_2$N(R$_{d6}$)—, —S(=O)N(R$_{d7}$)—, —O—, —S—, —C(=O)O—, —C(=S)—, —S(=O)— and —S(=O)$_2$—;

each of R$_{31-35}$ is dependently selected from the group consisting of H, F, Cl, Br, I, CN, OH, SH, NH$_2$, CHO, COOH, and C(=O)NH$_2$, or selected from the group consisting of a C$_{1-10}$ alkyl or heteroalkyl optionally substituted by R$_{01}$, a C$_{3-10}$ cyclohydrocarbyl or heterocyclohydrocarbyl, a C$_{1-10}$alkyl or heteroalkyl substituted by a C$_{3-10}$ cyclohydrocarbyl or heterocyclohydrocarbyl;

the definitions of R$_t$, R$_{d1-d7}$, R$_{01}$ refer to that in claim 1;

optionally, there is another linking bond (CH$_2$)$_{1-3}$ between T$_{31}$ and D$_{31}$, D$_{33}$ and D$_{34}$, T$_{33}$ and D$_{35}$.

In some embodiments of the present invention, each of D$_{31-35}$ is dependently selected from the group consisting of —C(=O)—, —O—, methylene, —N(CH$_3$)—, —CH(OH)—, and —CF$_2$—; each of R$_{31-34}$ is dependently selected from H, methyl, ethyl, n-propyl, iso-propyl.

In some embodiments of the present invention, R$_3$ is selected from the group consisting of

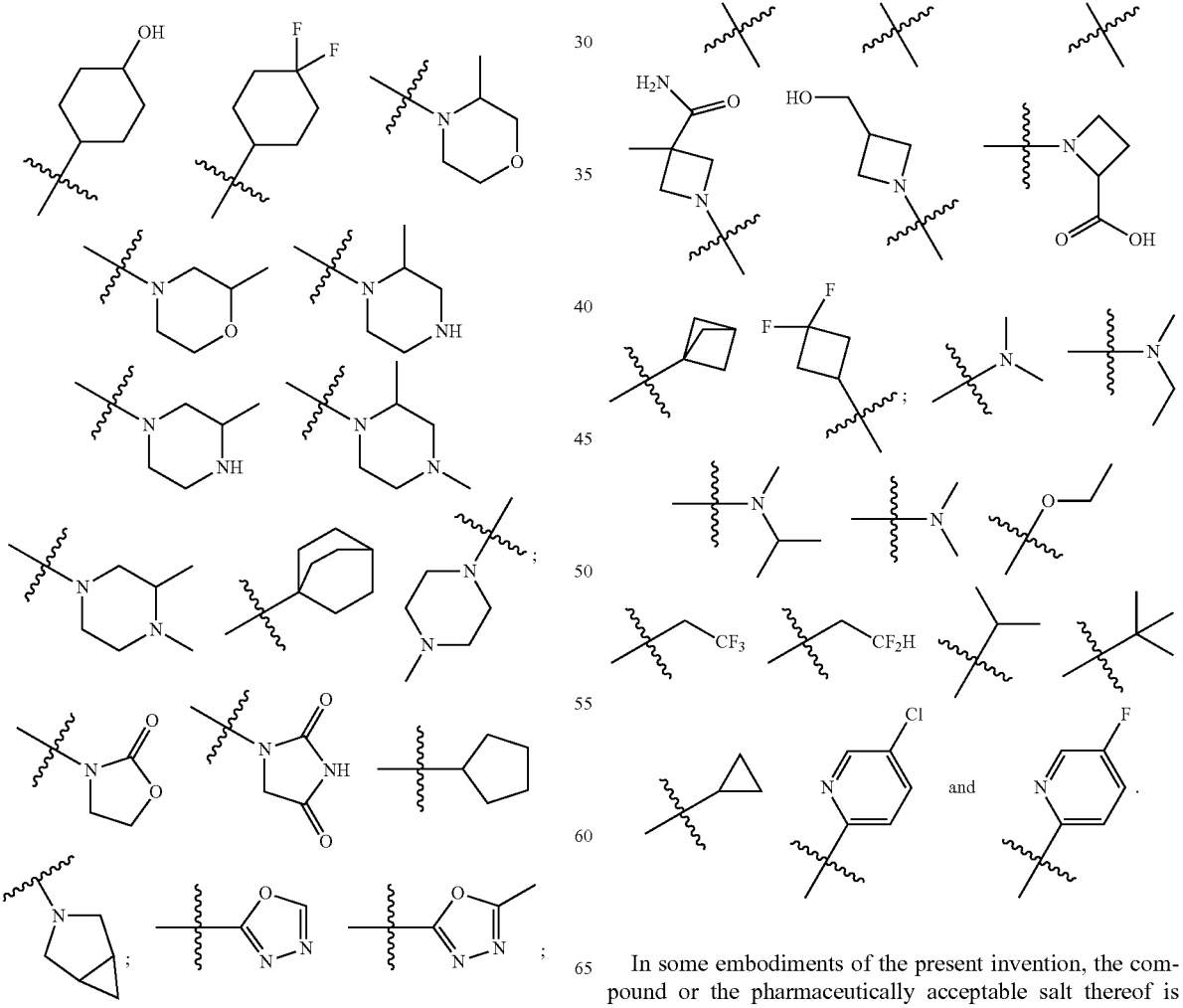

In some embodiments of the present invention, the compound or the pharmaceutically acceptable salt thereof is selected from the group consisting of

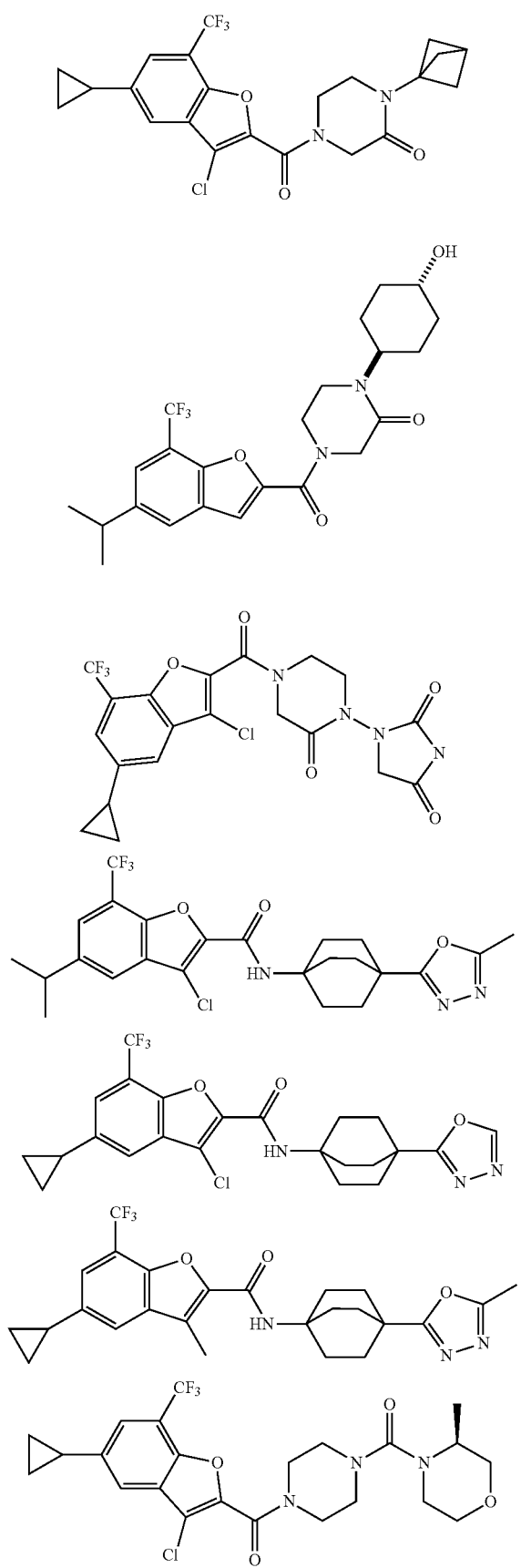
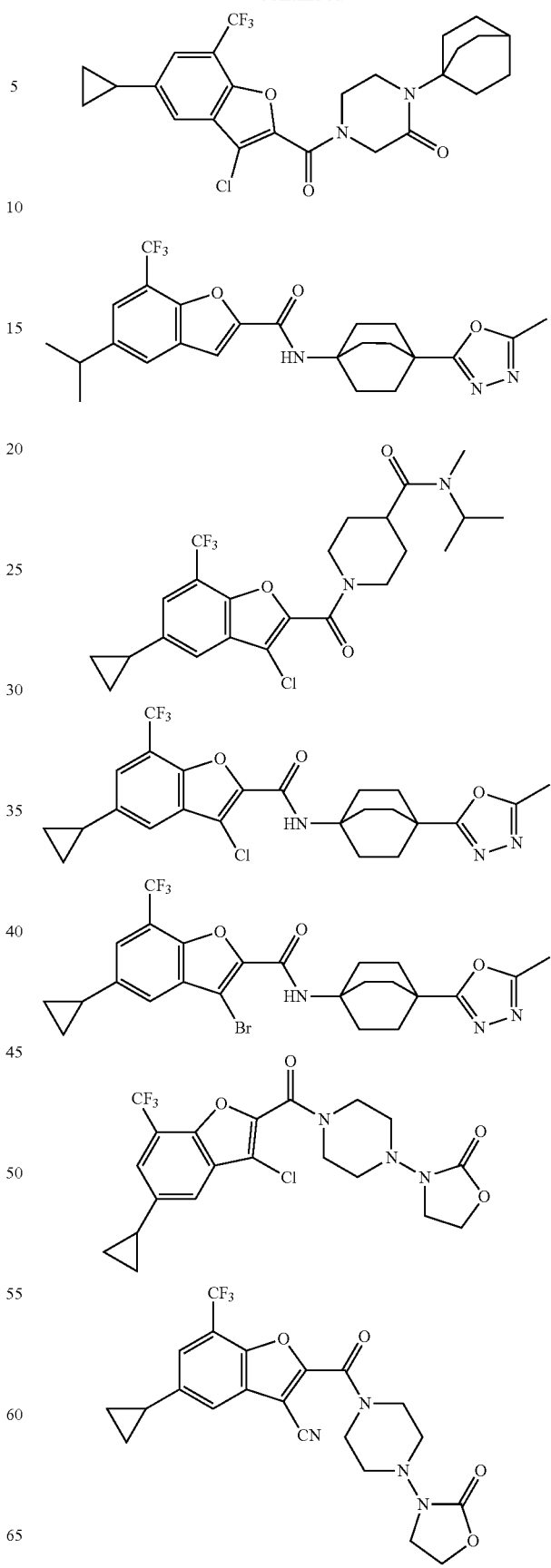

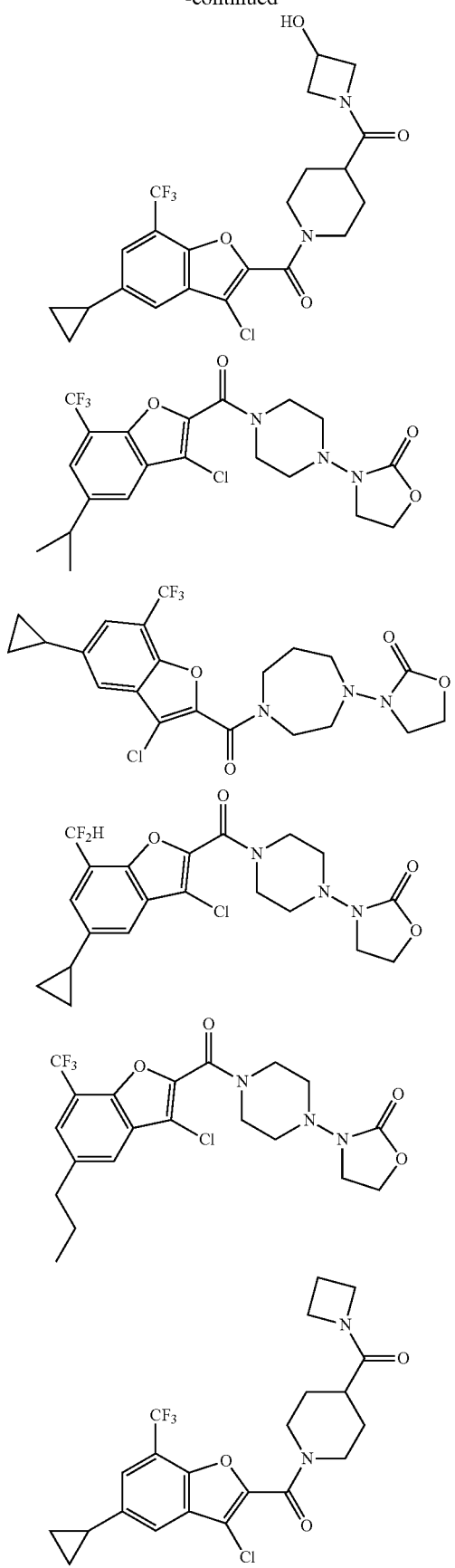
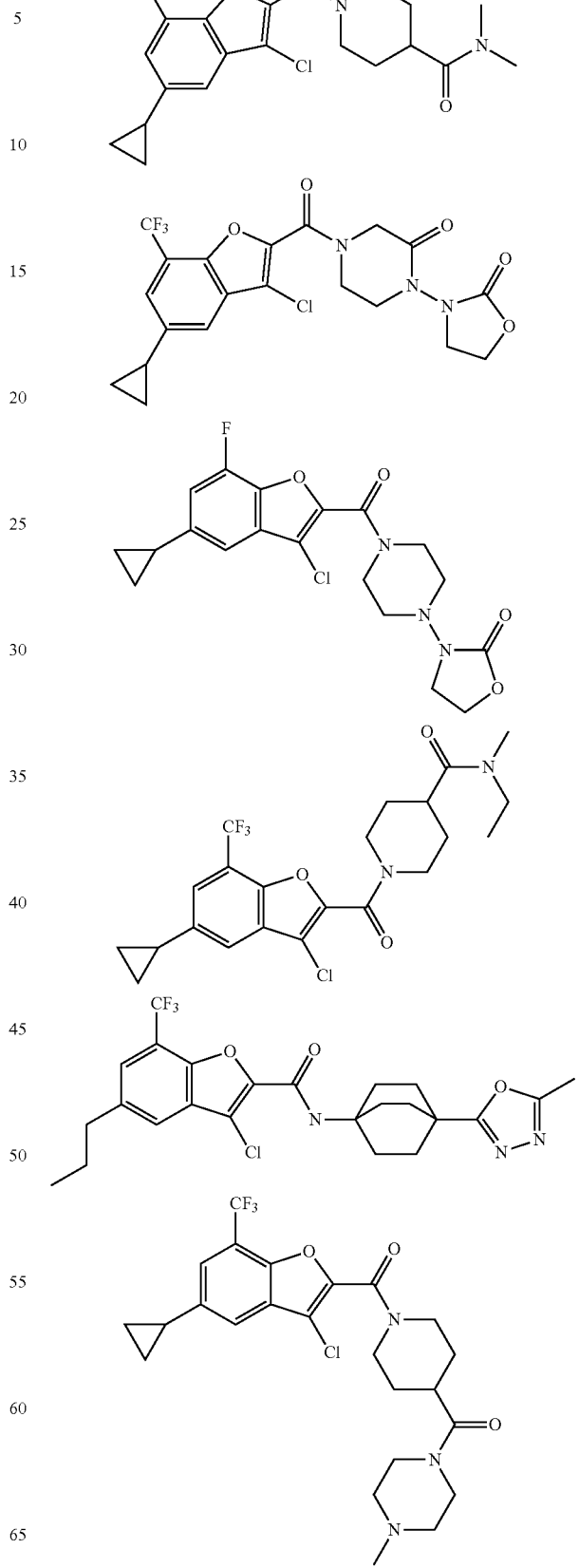

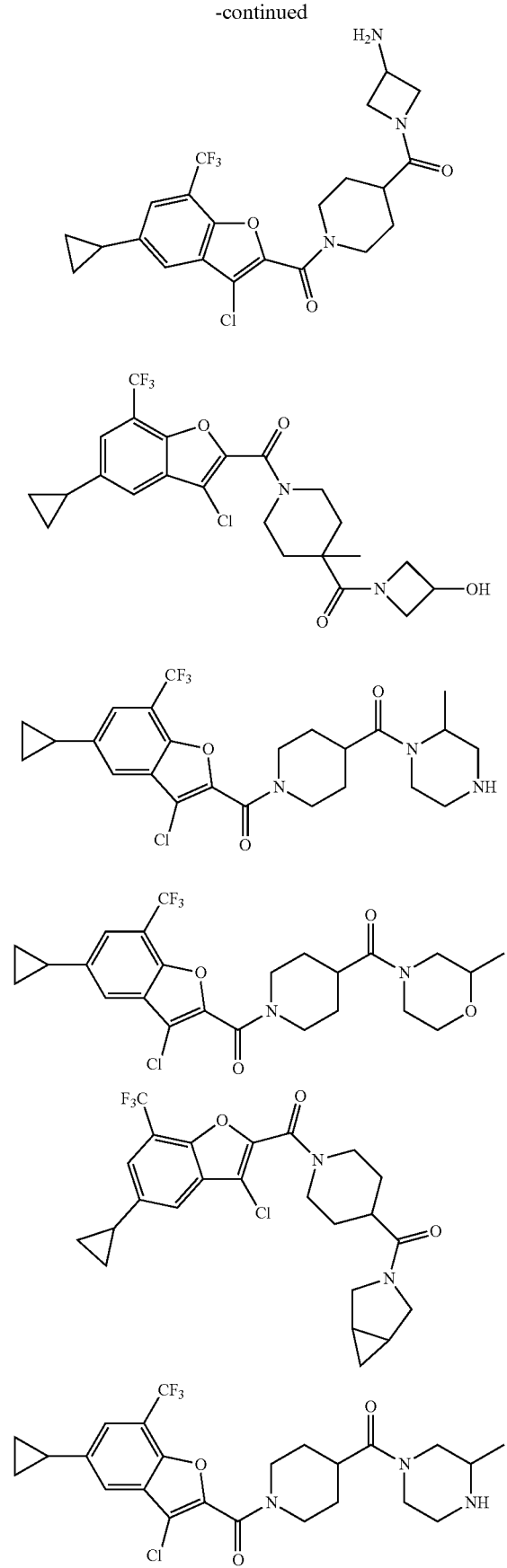
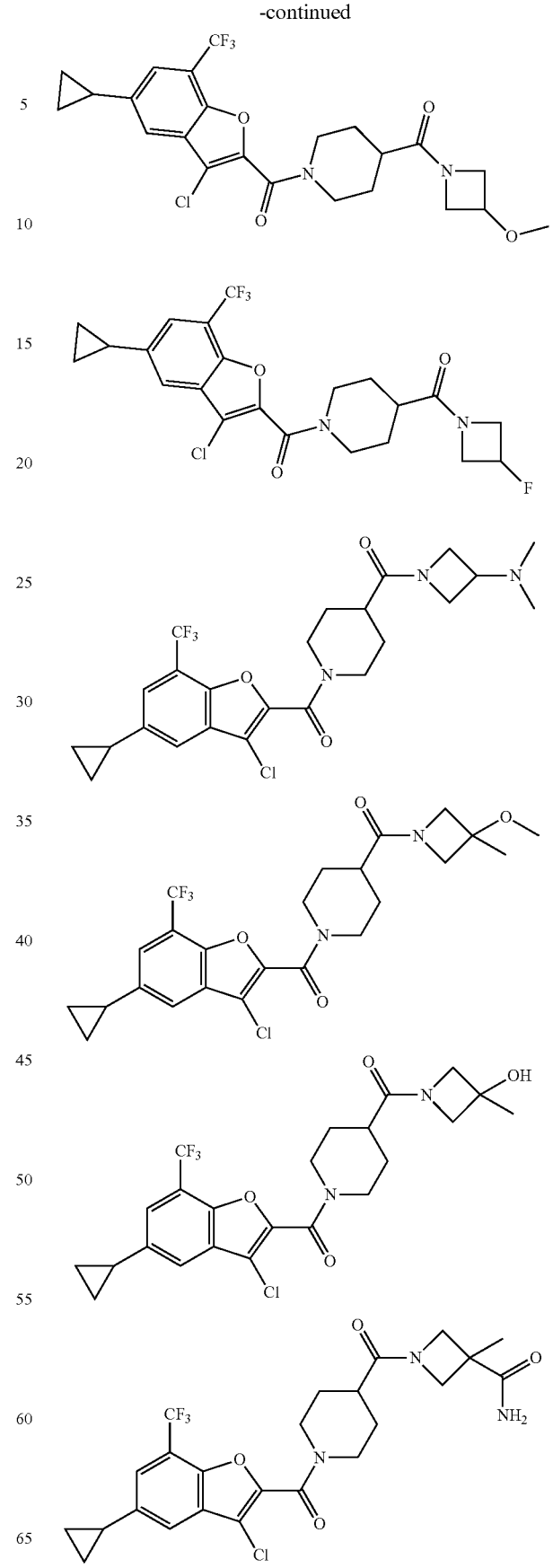

-continued
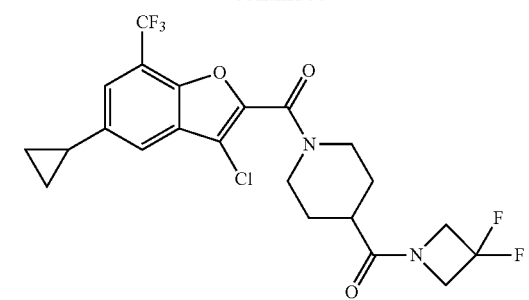
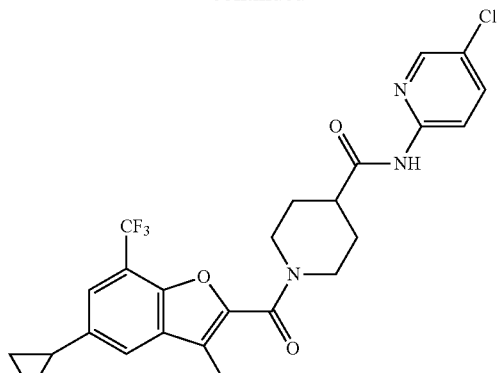
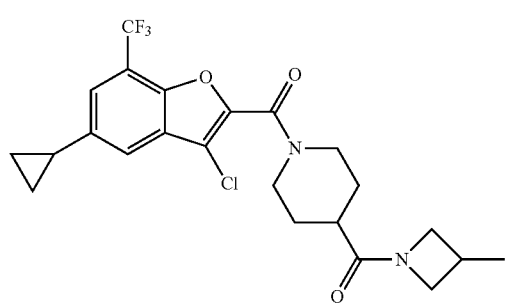
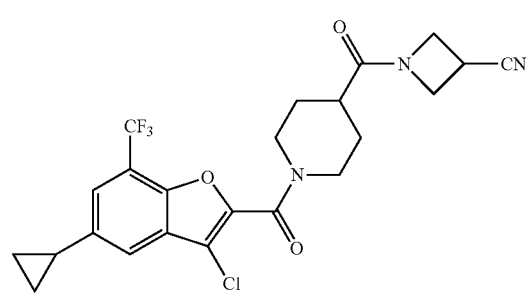
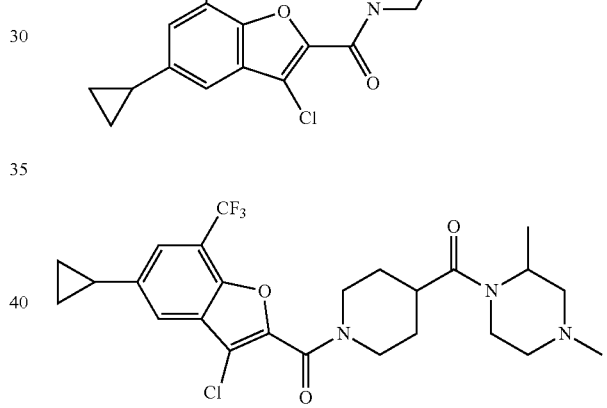
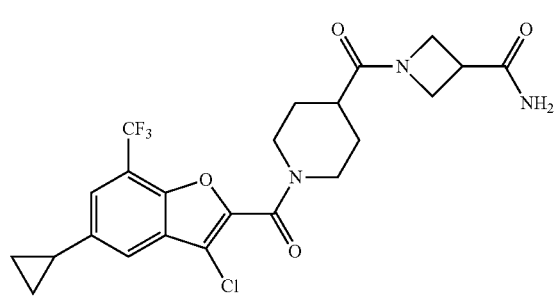
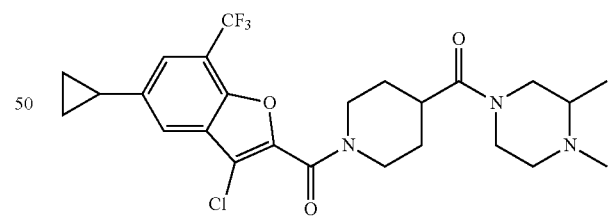
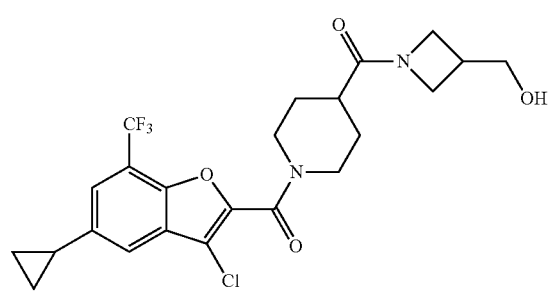
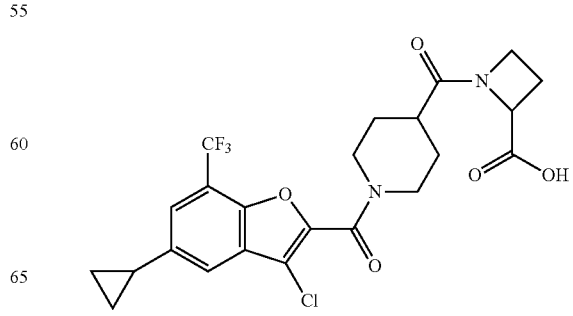

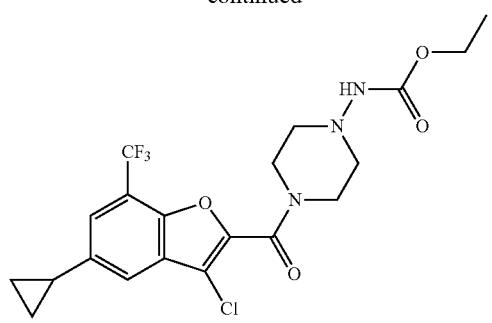
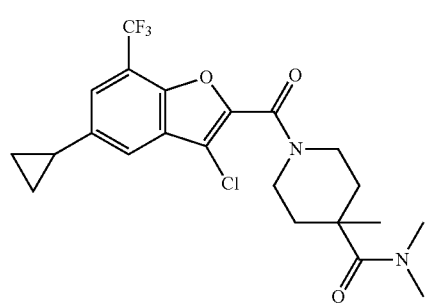
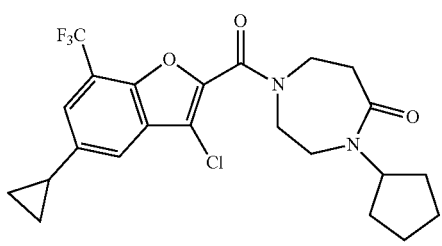
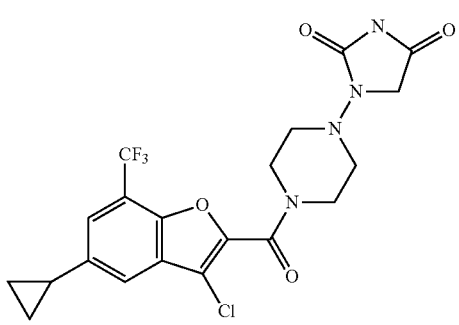
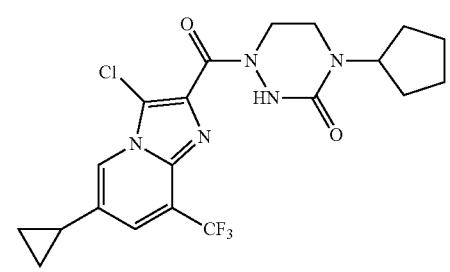
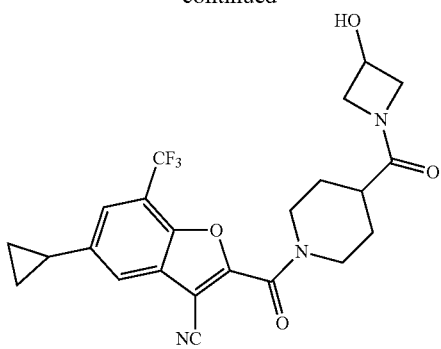
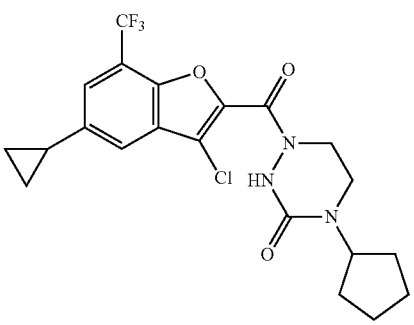
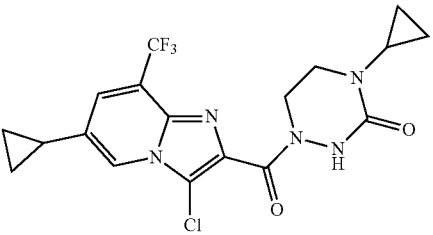
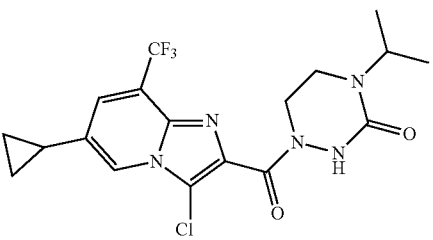
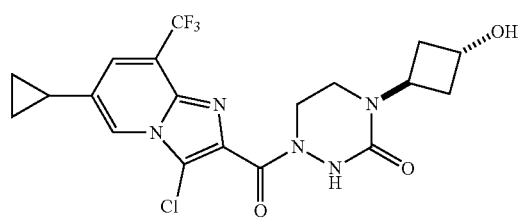
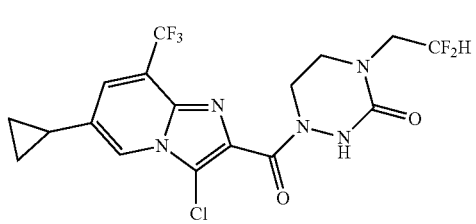

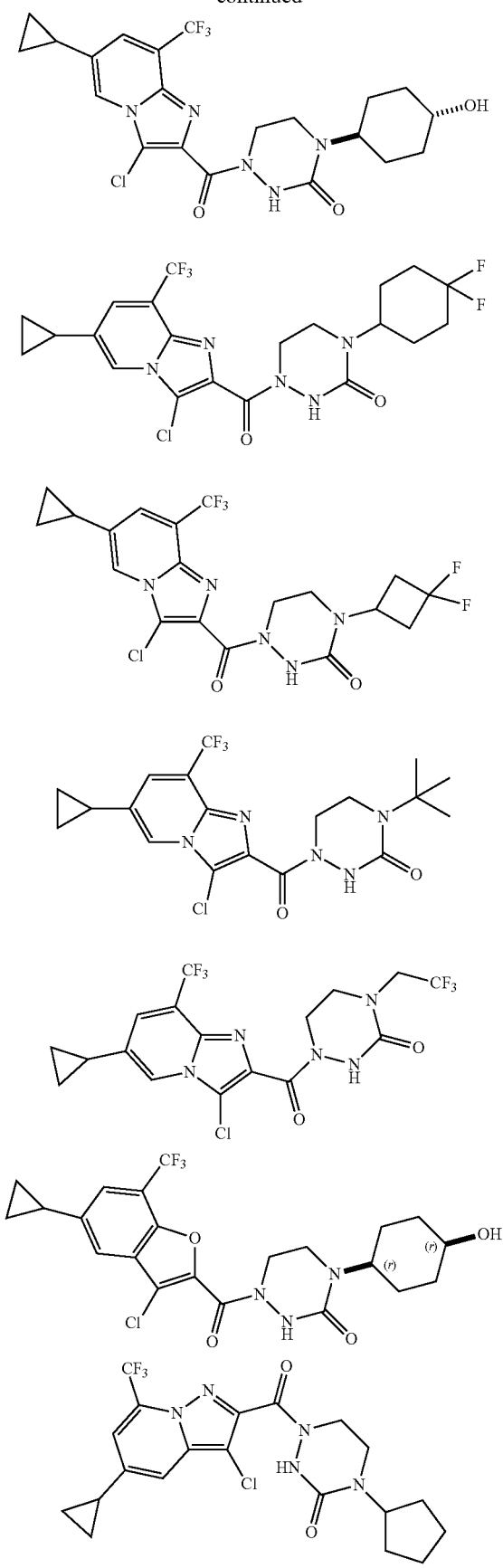

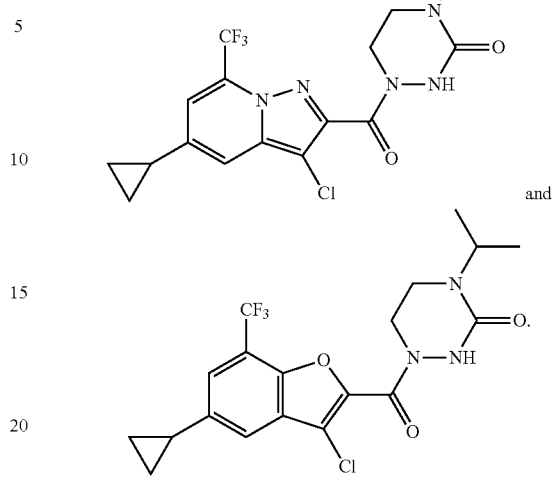

Relevant Definitions

Unless otherwise specified, the following terms and phrases used herein are intended to have the following meanings. A particular term or phrase should not be considered uncertain or unclear in the absence of a specific definition while should be understood according to the ordinary meaning. When a trade name appears herein, it refers to the corresponding commodity or its active ingredient.

$C_{1-10}$ is selected from $C_1$, $C_2$, $C_3$, $C_4$, $C_5$, $C_6$, $C_7$, $C_8$, $C_9$ and $C_{10}$; $C_{3-10}$ is selected from $C_3$, $C_4$, $C_5$, $C_6$, $C_7$, $C_8$, $C_9$ and $C_{10}$.

The $C_{1-10}$ alkyl or heteroalkyl, the $C_{3-10}$ cyclyl or heterocyclic hydrocarbonyl, the $C_{1-10}$ alkyl or heteroalkyl substituted by the $C_{3-10}$ cyclic hydrocarbonyl or the heterocyclic hydrocarbonyl include but not limited to:

a $C_{1-10}$ alkyl, a $C_{1-10}$ alkylamino, a N,N-bis($C_{1-10}$ alkyl) amino, a $C_{1-10}$ alkoxyl, a $C_{1-10}$ alkyl acyl, a $C_{1-10}$ alkoxycarbonyl, a $C_{1-10}$ alkyl sulfonyl, a $C_{1-10}$ alkyl sulfinyl, a $C_{3-10}$ cycloalkyl, a $C_{3-10}$ cycloalkyl amino, a $C_{3-10}$ heterocycloalkyl amino, a $C_{3-10}$ cycloalkoxy, a $C_{3-10}$ cycloalkyl acyl, a $C_{3-10}$ cycloalkoxy carbonyl, a $C_{3-10}$ cycloalkyl sulfonyl, a $C_{3-10}$ cycloalkyl sulfinyl;

methyl, ethyl, n-propyl, isopropyl, —CH$_2$C(CH$_3$)(CH$_3$)(OH), cyclopropyl, cyclobutyl, propyl methylene, cyclopropyl carbonyl, benzyloxy, trifluoromethyl, aminomethyl, hydroxymethyl, methoxy, formyl, methoxy carbonyl, methyl sulfonyl, methyl sulfinyl, ethoxy, acetyl, ethyl sulfonyl, ethoxy carbonyl, dimethylamino, diethylamino, dimethyl amino carbonyl, diethyl amino carbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN,

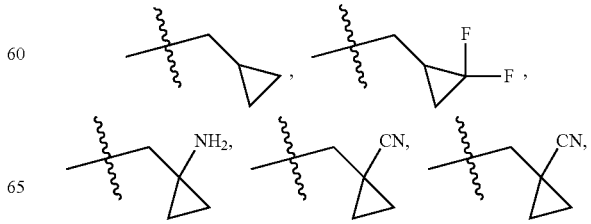

-continued
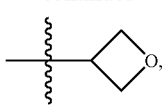
—CH$_2$CH(OH)(CH3)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$,
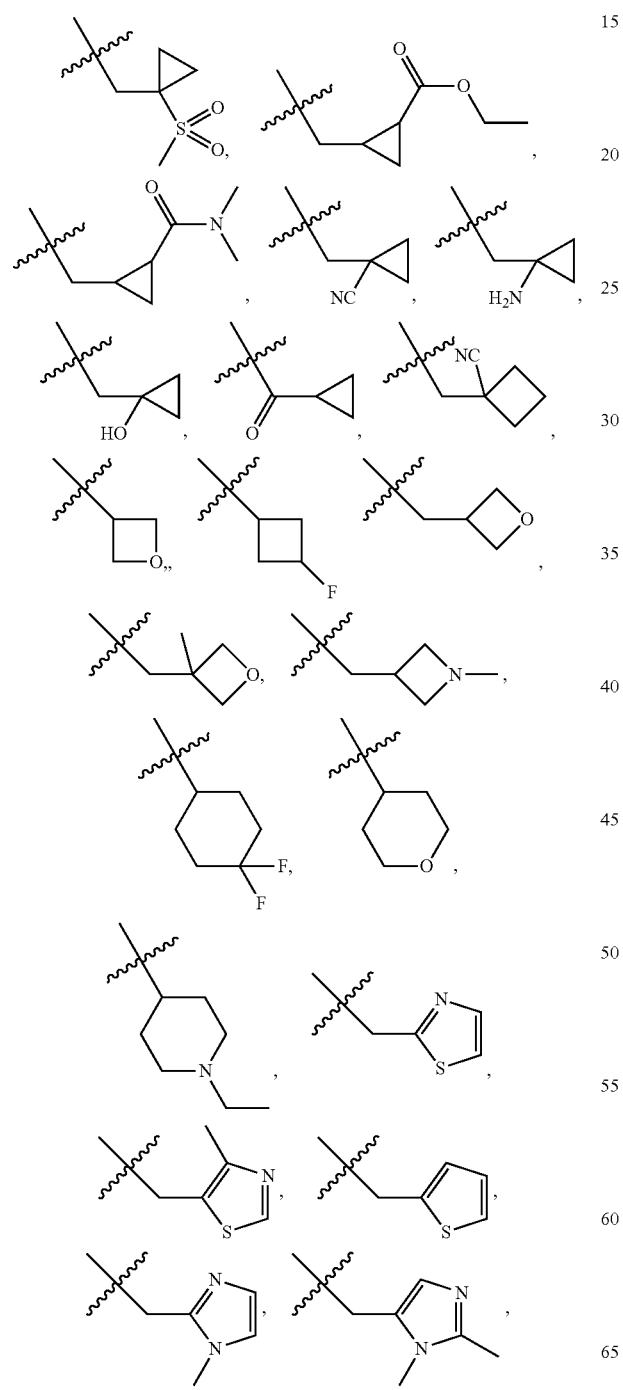
-continued
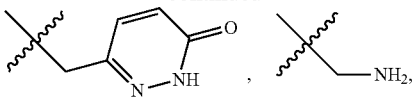
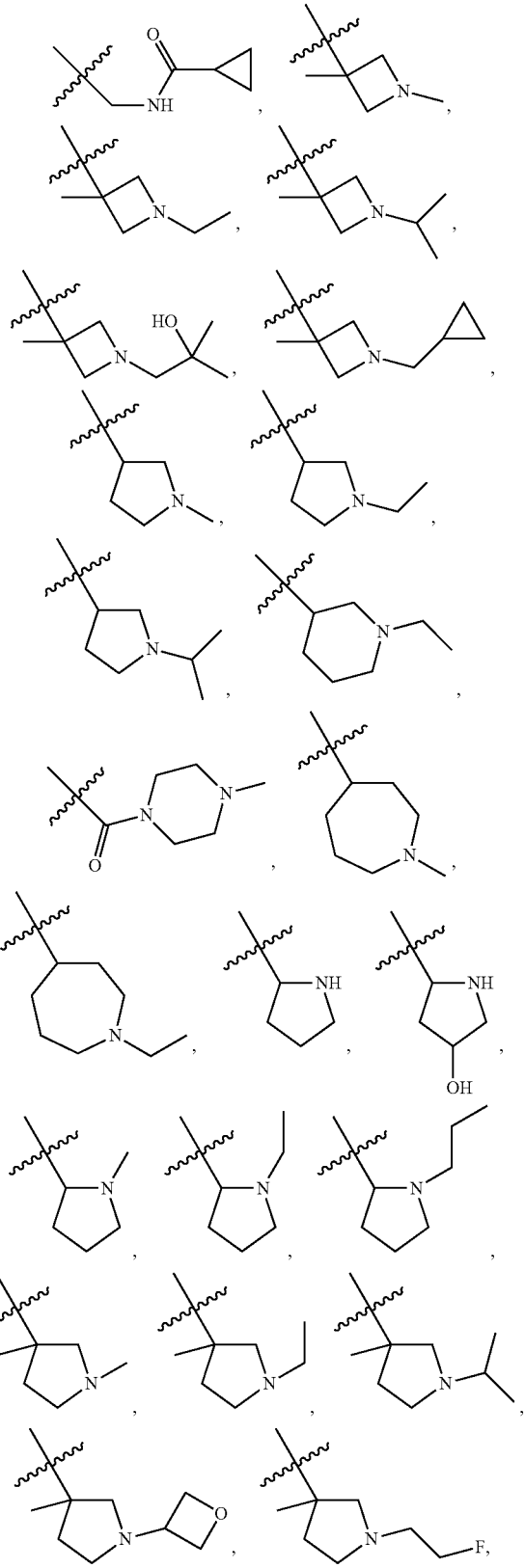

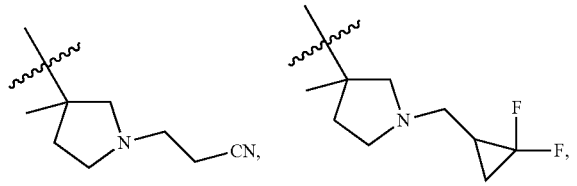 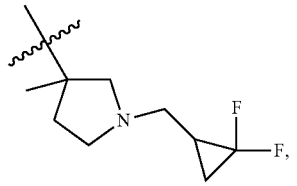 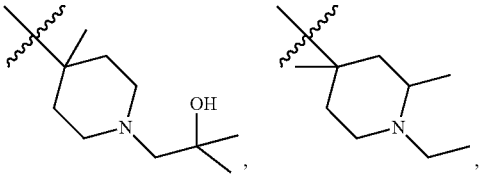 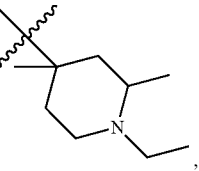
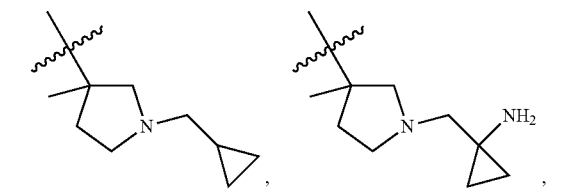 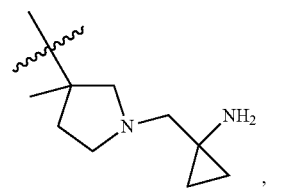 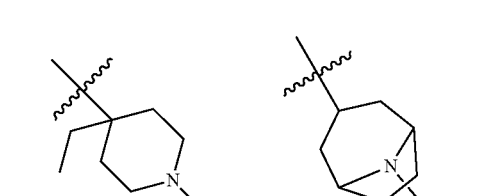 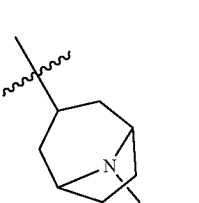
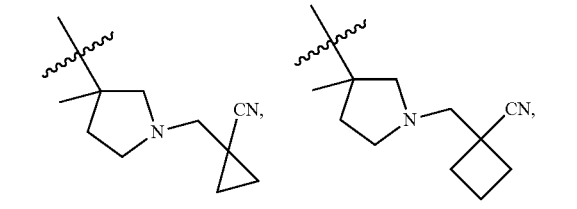 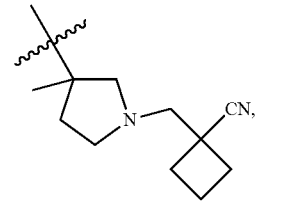 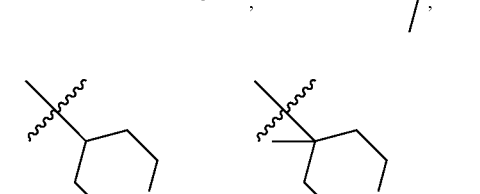 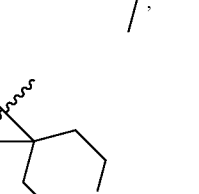
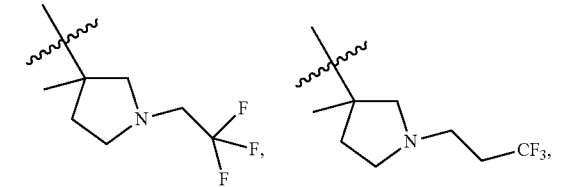 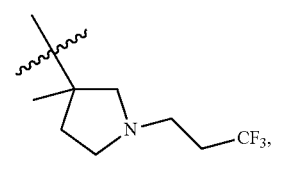 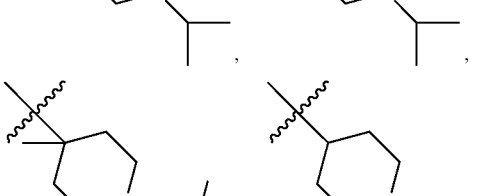 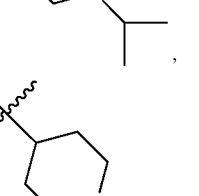
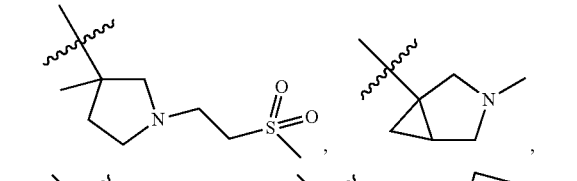 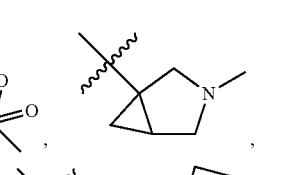 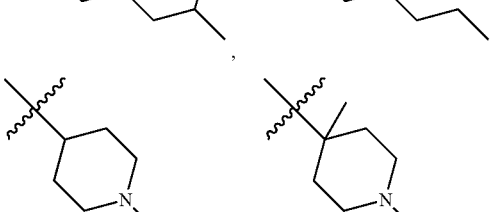 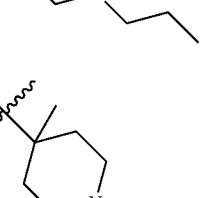
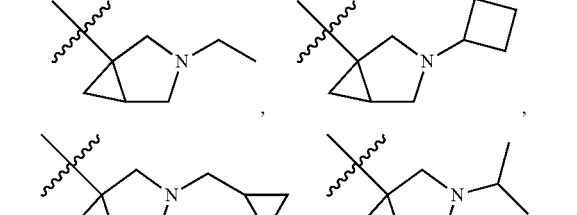 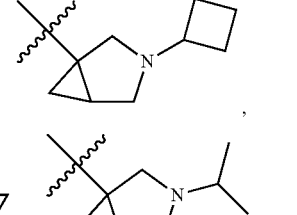 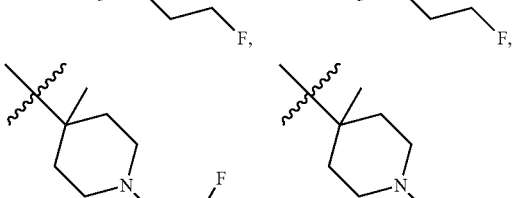 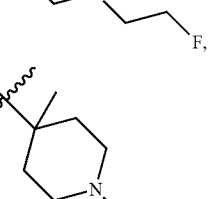
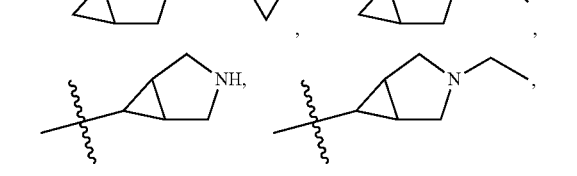 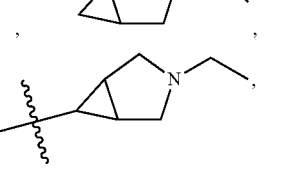 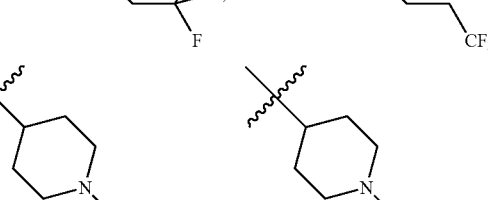 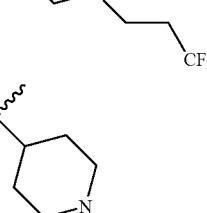
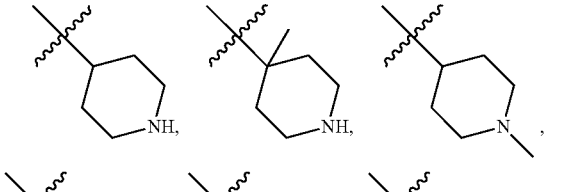 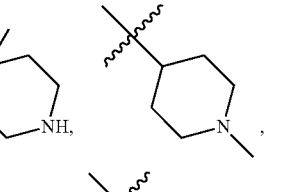 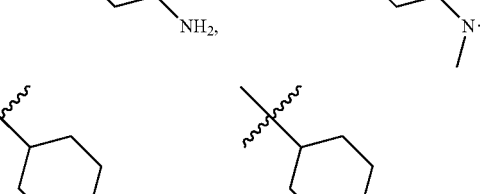 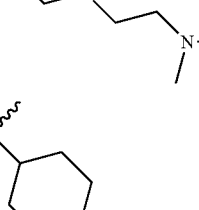
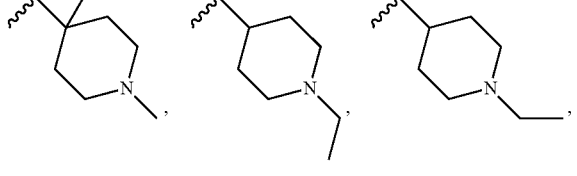 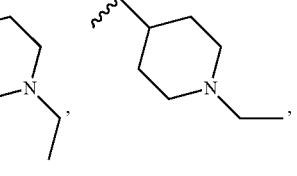 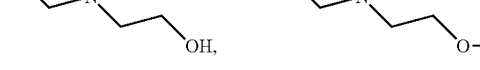 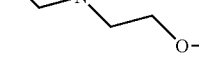
 

-continued
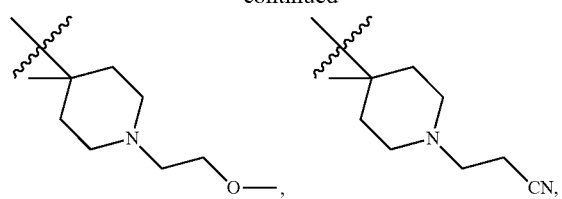
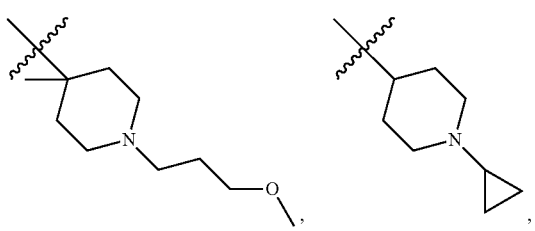
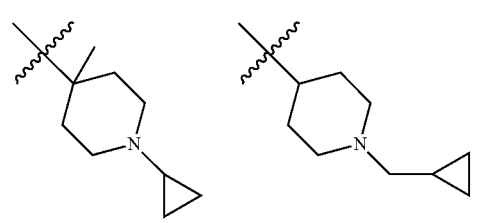
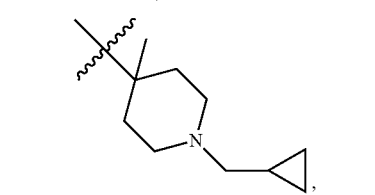
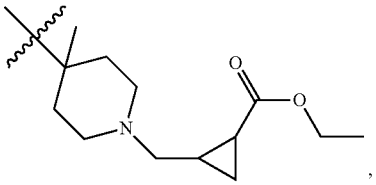
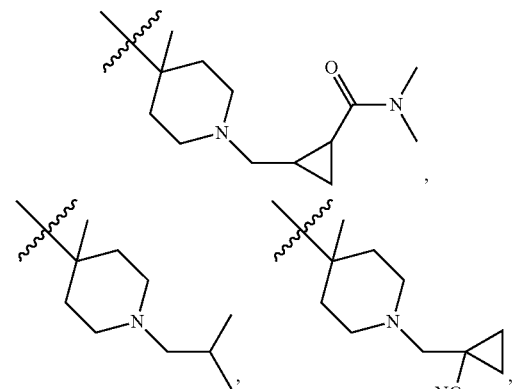
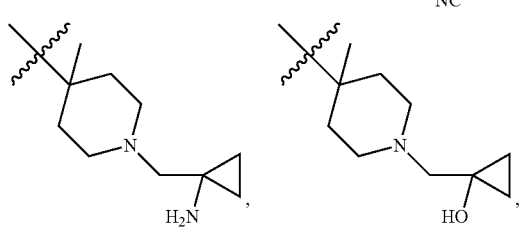
-continued
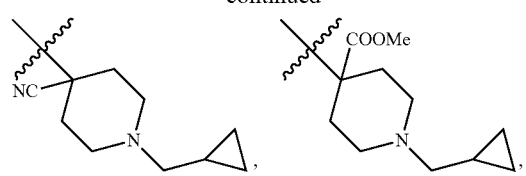
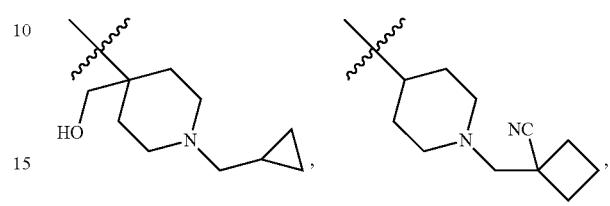
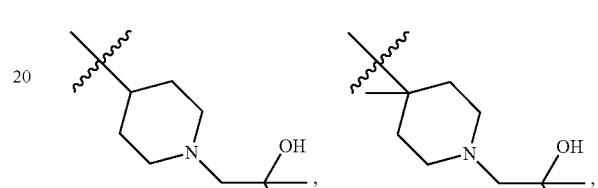
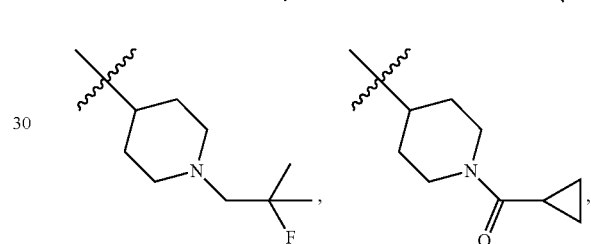
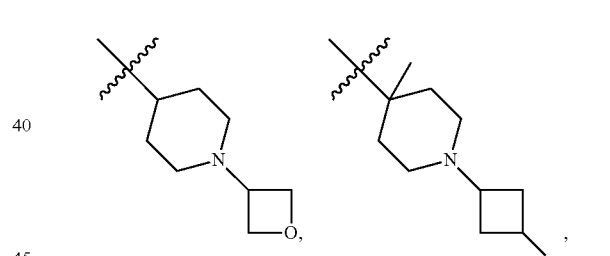
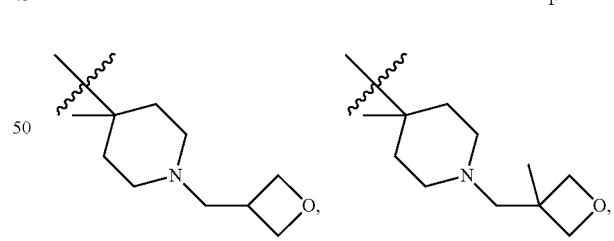
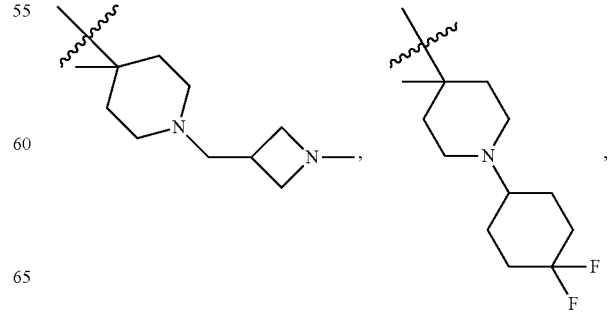

-continued

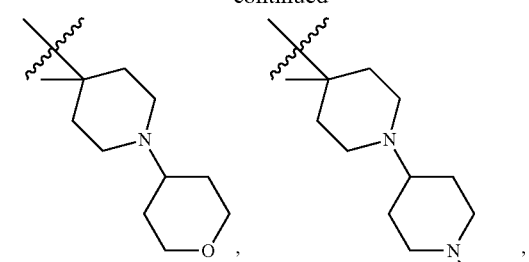
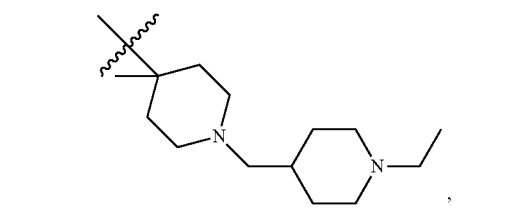
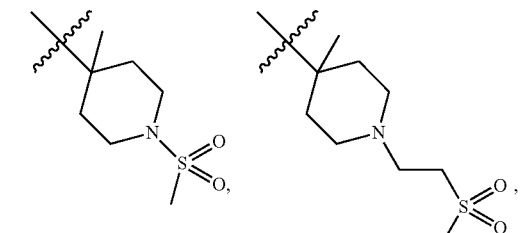
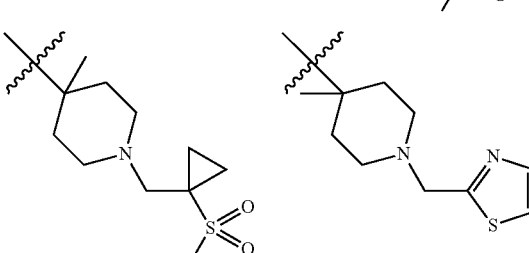
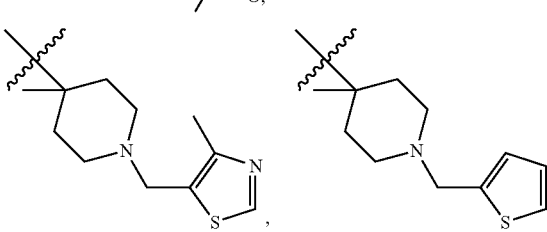
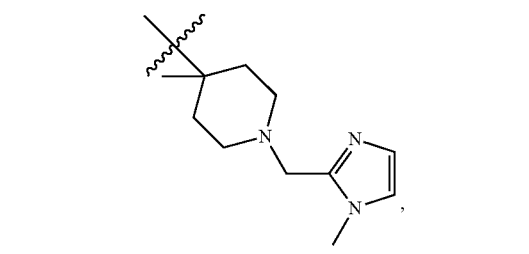
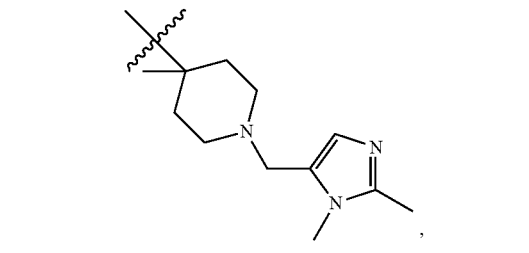

-continued

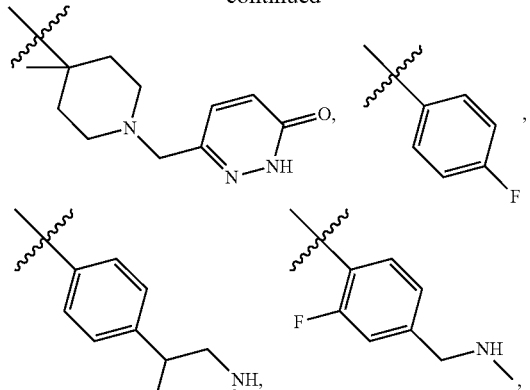
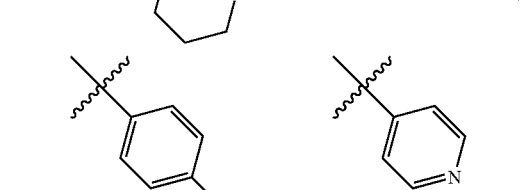
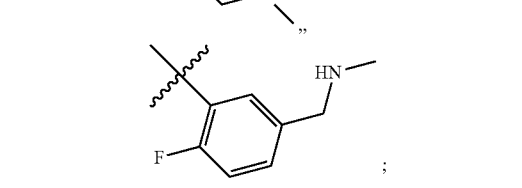

and phenyl, thiazolyl, biphenyl, naphthyl, cyclopentyl, furyl, 3-pyrrolinyl, pyrrolidinyl, 1,3-dioxolanyl, pyrazolyl, 2-pyrazolinyl, pyrazolidinyl, imidazolyl, oxazolyl, thiazolyl, 1,2,3-azolyl, 1,2,3-triazolyl, 1,2,4-triazolyl, 1,3,4-thiadiazolyl, 4H-pyranyl, pyridyl, piperidyl, 1,4-dioxanyl, morpholinyl, pyridazinyl, pyrimidinyl, pyrazinyl, piperazinyl, 1,3,5-trithianyl, 1,3,5-triazinyl, benzofuranyl, benzothiophenyl, indolyl, benzimidazolyl, benzothiazolyl, purinyl, quinolinyl, isoquinolinyl, cinnolinyl or quinoxalinyl;

$C_{6-12}$ aryl, $C_{6-12}$ aralkyl, $C_{6-12}$ heteroaromatics or $C_{6-12}$ heteroaralkyl;

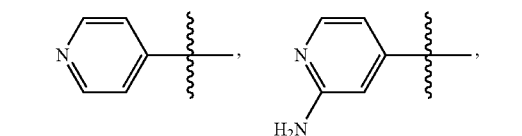
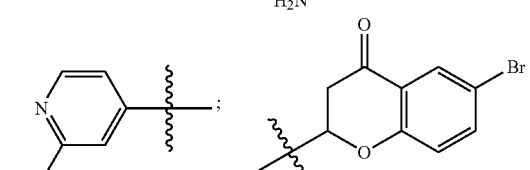
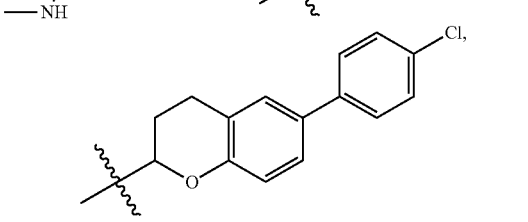

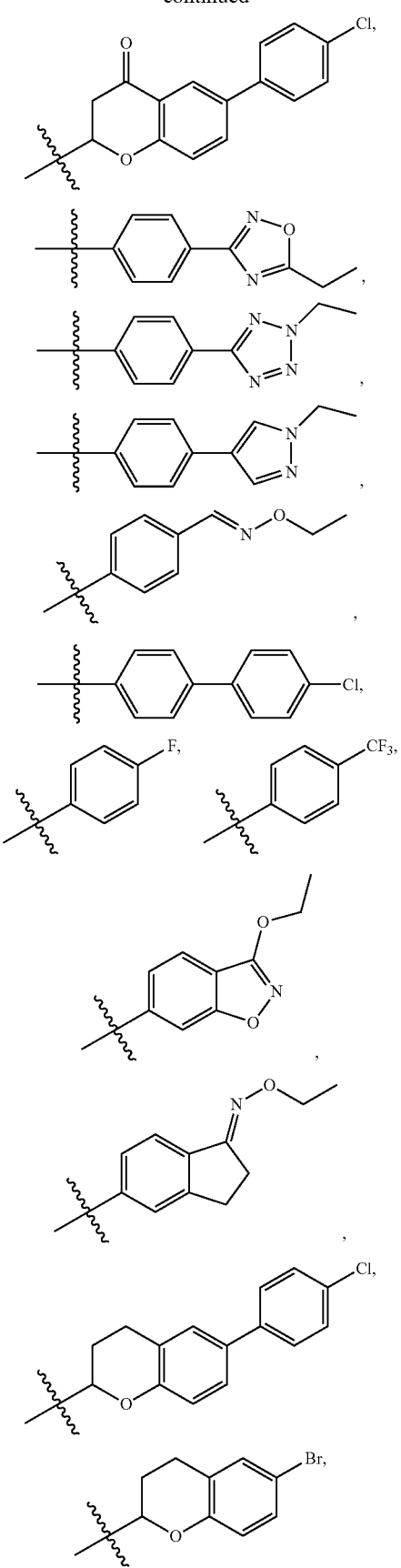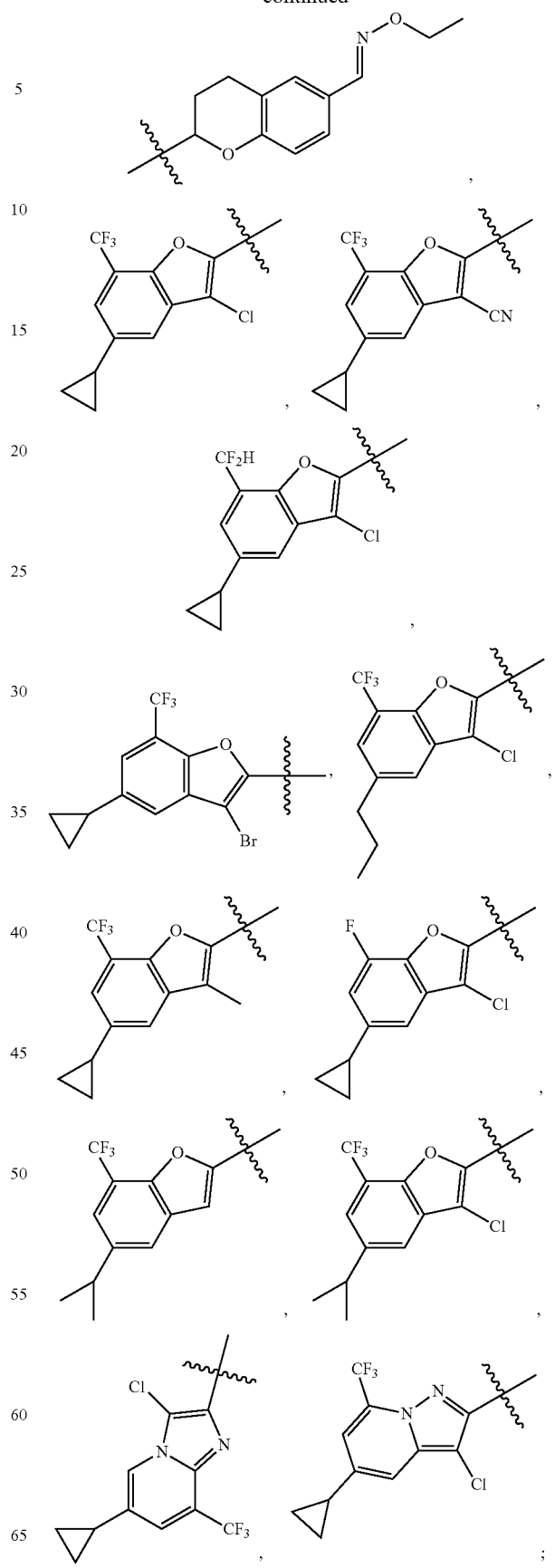

-continued

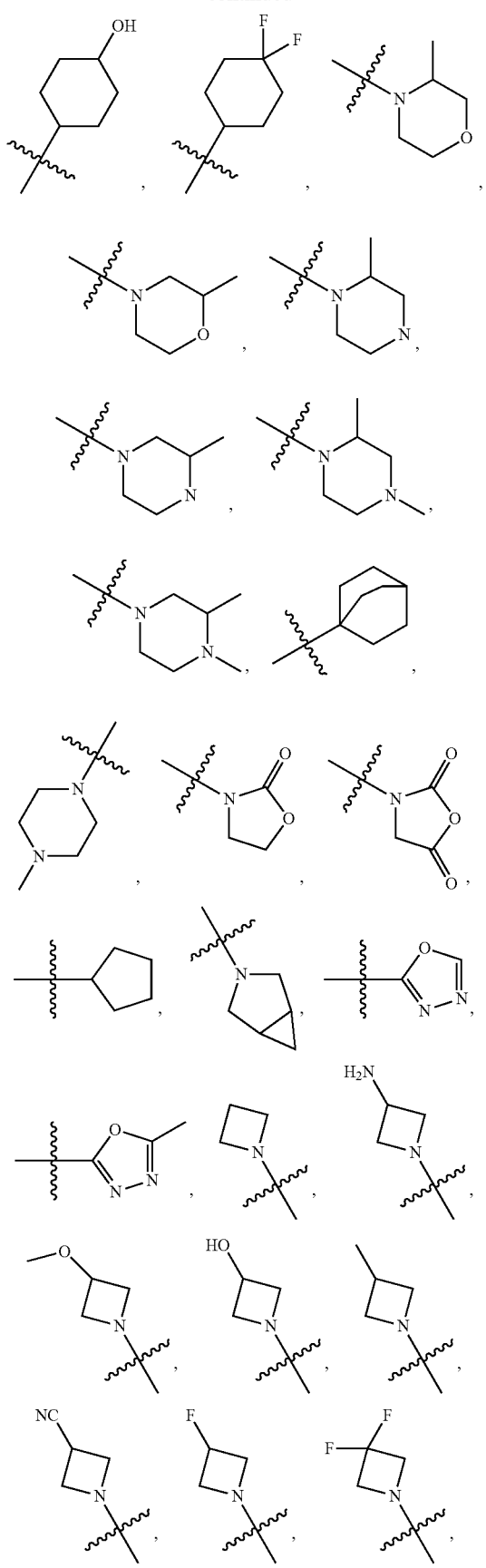

-continued

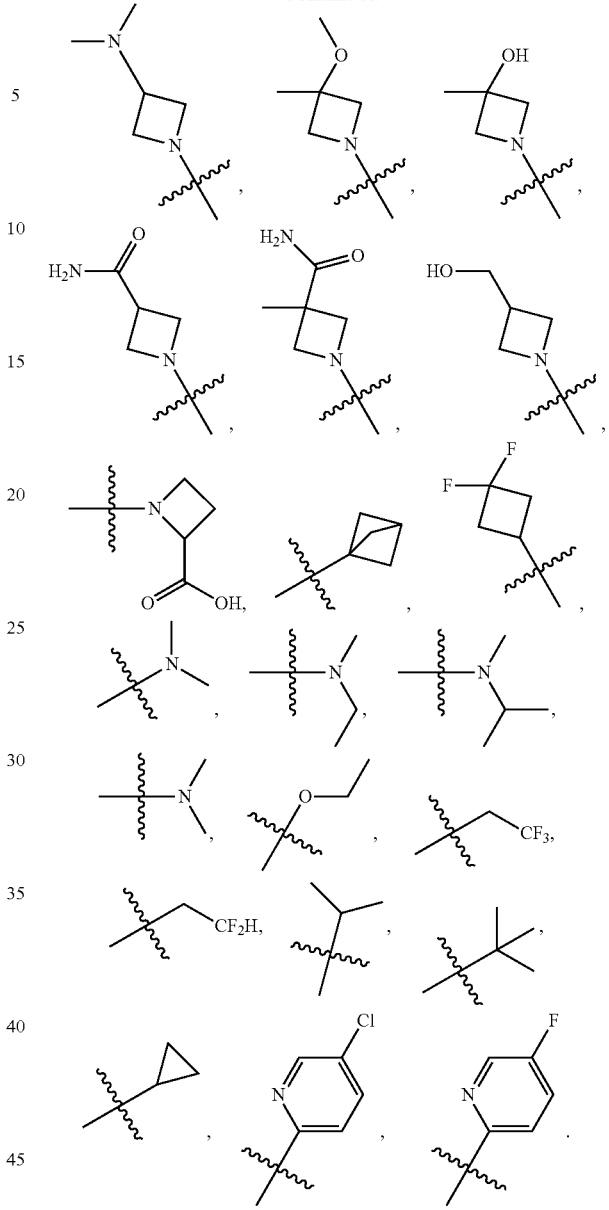

Herein, the term "pharmaceutically acceptable" is aimed at those compounds, materials, compositions and/or dosage forms, which are within the scope of reliable medical judgment and applicable for use in contact with human and animal tissue but without too much toxicity, irritation, allergic reactions or other problems or complications, also meet the reasonable benefit/risk ratio.

The term "pharmaceutically acceptable salt" refers to the salt of the compound of the present invention, which is prepared by the compound with specific substituent discovered by the present invention and relatively non-toxic acid or alkali. When the compound of the present invention contains a relatively acidic functional group, an alkali-addition salt can be obtained by contacting the compound in a neutral form with sufficient amount of alkali in a pure solution or suitable inert solvent. The pharmaceutically acceptable alkali-addition salt includes the salt of sodium, potassium, calcium, ammonium, organic ammonia or magnesium or the like. When the compound of the present invention contains a relatively alkaline functional group, an acid-addition salt can be obtained by contacting the compound in a neutral form with sufficient amount of acid in a pure solution or suitable inert solvent. Examples of the pharmaceutically acceptable acid-addition salt include a salt of inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and salt of organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes salt of amino acid (e.g. arginine etc.), and salt of organic acid such as glucuronic acid and the like (see Berge et al., "Pharmaceutical Salts", Journal of Pharmaceutical Science 66: 1-19 (1977)). Some specific compound of the present invention contains both alkaline and acidic functional groups so as to be transformed to be any alkali-addition or acid-addition salt.

Preferably, the neutral form of a compound is regenerated by contacting a salt with a base or an acid in a conventional manner and then separating the parent compound. The difference between a parent form of a compound and the various salt forms lies in some physical properties, such as that the solubility in a polar solvent is different.

The "pharmaceutically acceptable salt" in the present invention is the derivatives of the compound of the present invention, wherein, the parent compound is modified by salifying with an acid or an alkali. Examples of the pharmaceutically acceptable salt include but not limited to: an inorganic acid or organic acid salt of an alkali such as amine, an alkali metal or organic salt of acid radical such as carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes but not limited to those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthoic, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinate acid, succinic acid, aminosulfonic acid, sulfanilic acid, sulphuric acid, tannic acid, tartaric acid and p-toluene sulfonic acid.

The pharmaceutically acceptable salt of the present invention can be prepared by a conventional method with a parent compound containing an acidic or alkaline group. Generally, the preparation method of the salt comprises that in water or an organic solvent or the mixture of water and organic solvent, reacting these compounds in forms of free acids or alkalis with stoichiometric amount of proper alkalis or acids. In general, preferably choose non-aqueous media such as ether, ethyl acetate, ethanol, isopropanol or acetonitrile and so on.

Except for the form of salt, there is a form of prodrug for the compound in the present invention. The prodrug of the compound described in the present invention is easily transformed to be the compound of the present invention via chemical changes under physiological conditions. Besides, the prodrug can be transformed to be the compound of the present invention via chemical or biochemical method in vivo environment.

Some compounds of the present invention can exist in the form of non-solvate or solvate forms, including hydrate forms. In general, the solvate form is similar to the non-solvate form, both of which are included within the scope of the present invention. Some compounds of the present invention can contain asymmetric carbon atoms (optical center) or double bonds. The racemic isomers, diastereomers, geometric isomers and single isomers are included within the scope of the present invention.

The diagrammatic representation of the racemic isomer, the ambiscalemic and scalemic or the enantiopure compound of the present invention is from Maehr, J. Chem. Ed. 1985, 62: 114-120. Unless otherwise indicated, the absolute configuration of a stereocenter is represented by the wedge and dashed lines. When the compound of the present invention contains a vinyl double bond or other geometric asymmetric center, unless otherwise specified, E, Z geometric isomers are included. Similarly, all tautomeric forms are included within the scope of the present invention.

The compound of the present invention may exist as a specific geometric or stereoisomeric isomer. The present invention envisages all of this class of compounds, including cis- and trans-isomers, (–)- and (+)-antimers, (R)- and (S)-antimers, diastereomers, (D)-isomer, (L)-isomer, as well as racemic mixtures and other mixtures, such as enantiomers- or diastereoisomers-enriched mixtures, all of these mixtures are within the scope of the present invention. Other asymmetric carbon atoms may exist in substituents such as in an alkyl. All of these isomers and their mixtures are included within the scope of the present invention.

Optically active (R)- and (S)-isomers, (D)- and (L)-isomers can be prepared by asymmetric synthesis or chiral reagents or other conventional techniques. If an enantiomer of a compound of the present invention are wanted, asymmetric synthesis or derivatization action of the chiral auxiliaries can be employed in preparation, in which the resulting diastereomer mixtures are isolated, and the auxiliary groups are cleaved to provide the pure desired enantiomer. Or, when a molecule contains an alkaline functional group (such as amino) or an acidic functional groups (such as carboxyl), a salt of diastereomer is formed with an appropriate optical active acid or alkali, and then the pure enantiomer can be recycled after resolution on the salt of diastereomer by common methods which is known in the art. In addition, the separation of an enantiomer and a diastereomer is usually realized by the chromatographic method, the chromatography method employs a chiral stationary phase, and optionally combined with the chemical derivatization method (e.g. an amine generates a carbamate).

One or more than one atoms constituting the compound of the present invention may comprise an unnatural proportion of atomic isotopes. For example, the compound can be labeled by a radioactive isotope, such as tritium ($^3$H), iodine-125 ($^{125}$I) or C-14 ($^{14}$C). All the variations in the isotopic composition of the compound disclosed in the present invention, whether radioactive or not, are included within the scope of the present invention.

The term "a pharmaceutically acceptable carrier" refers to any formulation or carrier medium which is capable of delivering effective amount of the active substance disclosed in the present invention, does not interfere with the biological activity of the active substance, and is with no toxic side-effects on host or patient, representative carrier includes water, oil, vegetables and minerals, cream base, lotion matrix, ointment matrix etc. The matrix comprises a suspension, a viscosity increaser, transdermal enhancers etc. Their formulation are well known to the person in cosmetic or topical drug art. Other information about the carrier can refer to Remington: The Science and Practice of Pharmacy, 21st Ed., Lippincott, Williams & Wilkins (2005), the content of which is incorporated herein by its entirety.

The term "excipient" usually refers to a carrier, diluent and/or medium required for the preparation of an effective pharmaceutical composition.

In terms of drug or pharmacological active agent, the term "effective amount" or "therapeutically effective amount" refers to enough quantity of the drug or formulation that can achieve desired effects but is with no toxicity. For the oral formulation of the present invention, "an effective amount" of one active substance in the composition is the amount required to achieve desired effects in combination with another active substance in the composition. The determination of the effective amount varies from person to person, which depends on the age and the general situation of the recipient, also on the specific active substance. In one case, an appropriate effective amount can be determined by the person skilled in the art according to conventional tests.

The term "active ingredient", "therapeutic agent", "active substance" or "active agent" refers to a chemical entity, which can effectively treat disorder, illness or disease of a target subject.

The term "substituted" refers to one or more hydrogen atoms in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of stability available in chemistry.

When any parameter (e.g. R) shows an occurrence for more than one times in the composition or structure of the compound, the definition of each occurrence is independent. Therefore, for example, if a group is substituted by 0-2 of R, the group may optionally be substituted by at most two R, and R has an independent option in each case. In addition, the combination of substituents and/or their variants is allowed only if such a combination will lead to a stable compound.

When the number of the connection group is 0, such as —(CRR)$_0$—, it indicates that the connection group is a single bond.

When one of the parameters is selected from a single bond, it indicates that the two groups which it is attached are directly connected, for example, when the L in A-L-Z represents a single bond, it indicates that the structure actually is A-Z.

When one bond of a substituent can be crossly connected to two atoms of a ring, the substituent can be bonded to arbitrary atoms in the ring. When the listed substituent does not specify through which atom it is connected to the general structure formula including the compound that is not specifically mentioned, the substituent can be bonded through any of its atoms. The combination of substituents and/or their variants is allowed only if such a combination will lead to a stable compound. For example, the structural unit

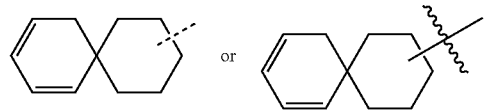

represents that the connection can occur on any atom in the cyclohexyl or cyclohexadiene.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated ($C_1$-$C_4$) alkyl" is intended to include but not limited to trifluoromethyl, 2,2,2-trifluoroethyl, 4-chlorobutyl and 3-bromopropyl, etc.

Examples of halogenated alkyl include but not limited to: trifluoromethyl, trichloromethyl, pentafluoroethyl, and pentachloroethyl. The "alkoxy" represents that the alkyl group with a specific number of carbon atoms is connected by an oxygen bridge. The $C_{1-6}$ alkoxy includes $C_1$, $C_2$, $C_3$, $C_4$, $C_5$ and $C_6$ alkoxy. Examples of alkoxy include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes $C_3$, $C_4$, $C_5$, $C_6$ and $C_7$ cycloalkyl. The "alkenyl" includes linear or branched hydrocarbon chain, wherein any stable sites on the chain exist one or more C=C double bonds, such as vinyl and propenyl.

The term "halo" or "halogen" refers to fluorine, chlorine, bromine and iodine.

Unless otherwise specified, the term "hetero" refers to a heteroatom or a heteroatomic group (i.e. a group containing a heteroatom), including atoms except carbon (C) and hydrogen (H) and groups containing these heteroatoms, such as including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. A number of the atoms in the ring is usually defined as the member of the ring, for example, "5- to 7-membered ring" is a ring looped with 5 to 7 atoms. Unless otherwise specified, the ring optionally contains 1-3 of heteroatoms. Therefore, "5- to 7-membered ring" includes, for example, phenyl pyridine and piperidinyl; on the other hand, the term "5- to 7-membered heterocycloalkyl ring" includes pyridyl and piperidinyl, but does not include phenyl. The term "ring" also includes a ring system containing at least one ring, wherein each ring is of the above definition independently.

Unless otherwise specified, the term "heterocycle" or "heterocyclyl" refers to a stable monocyclic, bicyclic or tricyclic ring containing a heteroatom and a heteroatomic group, they can be saturated, partially unsaturated or unsaturated (aromatic), they contain carbon atoms and 1, 2, 3 or 4 of heteroatom in the ring which is independently selected from the group consisting of N, O and S, wherein any of the heterocycle can be fused to a benzene ring to form a bicyclic ring. Nitrogen and sulfur atoms can be optionally oxidized (i.e., NO and $S(O)_p$, p is 1 or 2). The nitrogen atom can be substituted or unsubstituted (i.e. N or NR, wherein R is H or other substituent that has been defined herein). The heterocycle can be attached to the side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment of the present invention, when the total number of S and O atoms contained in the heterocycle exceeds 1, these heteroatoms are not adjacent to each other. As another preferred embodiment of the present invention, the total number of S and O atoms in the heterocycle is no more than 1. As used herein, the term "aromatic heterocyclic group" or "heteroaryl" refers to a stable 5-, 6-, 7-membered monocycle or bicycle or 7-, 8-, 9- or 10-membered bicyclic heteroaromatic ring, which contains carbon atoms and 1, 2, 3 or 4 of heteroatom in the ring which independently selected from the group consisting of N, O and S. The nitrogen atom can be substituted or unsubstituted (i.e. N or NR, wherein R is H or other substituent that has been defined herein). Nitrogen and sulfur atoms can be optionally oxidized (i.e., NO and $S(O)_p$, p is 1 or 2). It is worth noting that, the total number of S and O atoms in the heteroaromatic ring is no more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to: one carbon atom, two carbon atoms, one nitrogen atom, two nitrogen atoms and one carbon-nitrogen group. It is worth noting that, a bridge always converts a monocyclic ring into a tricyclic ring. In the bridged ring, the substituent in the ring can also locate on the bridge.

Examples of heterocyclic compound include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2, 3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, triazinyl, 1,2,3-triazolyl, 1,2,4-triazolyl, 1,2,5-triazolyl, 1,3,4-triazolyl and xanthenyl. Fused ring and spiro ring compound are also included.

Unless otherwise specified, the term "hydrocarbonyl" or its specific concept (such as alkyl, alkenyl, alkynyl, phenyl, etc.) itself or as a part of another substituent represents a linear, branched or cyclic hydrocarbonyl or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1-10 carbon atoms). The term "alkyl" includes but not limited to an aliphatic hydrocarbonyl and aromatic hydrocarbonyl, the aliphatic hydrocarbonyl includes linear and cyclic structures, specifically includes but not limited to alkyl, alkenyl and alkynyl, the aromatic hydrocarbonyl includes but not limited to 6- to 12-membered aromatic hydrocarbonyl such as benzene, naphthalene and the like. In some embodiments, the term "hydrocarbonyl" refers to linear or branched groups or their combination, which can be completely saturated, monocyclic or polycyclic unsaturated, can include divalent and polyvalent groups. Examples of saturated hydrocarbonyl include but not limited to homologues or isomers of methyl, ethyl, n-propyl, iso-propyl, n-butyl, tert-butyl, iso-butyl, sec-butyl, iso-butyl, cyclohexyl, (cyclohexyl) methyl, cyclopropyl methyl, and n-amyl, n-hexyl, n-heptyl, n-octyl and the like. Unsaturated alkyl has one or more double or triple bond, examples of which includes but not limited to vinyl, 2-propenyl, butenyl, crotyl, 2-isopentenyl, 2-butadienyl, 2,4-(pentadienyl), 3-(1, 4-pentadienyl), acetenyl, 1- and 3-propinyl, 3-butynyl, and more advanced homologues and isomers.

Unless otherwise specified, the term "heterohydrocarbonyl" or its specific concepts (such as heteroalkyl, heteroalkenyl, heteroalkynyl, heteroaryl, etc.) itself or the term combining with another term refers to a stable linear, branched or cyclic hydrocarbonyl or their combinations, which consists of a certain number of carbon atoms and at least one heteroatom. In some embodiments, the term "heterohydrocarbonyl" itself or the term combining with another term refers to a stable linear, branched hydrocarbonyl or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. Heteroatoms B, O, N and S can be located in any internal position of the heterohydrocarbonyl (including the position where hydrocarbonyl is attached to the rest part of the molecule). Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms are adjacent, such as —$CH_2$—NH—$OCH_3$.

The terms "alkoxy", "alkylamino" and "alkylthio" (or thioalkoxy) are the idiomatic expressions, which refers to the alkyl group is attached to the rest of molecule through an oxygen, an amino, or a sulfur atom, respectively.

Unless otherwise specified, the term "cyclohydrocarbonyl", "heterocyclohydrocarbonyl" or its specific concepts (such as aryl, heteroaryl, cycloalkyl, heterocycloalkyl, cycloalkenyl, heterocyclovinyl, cycloalkynyl, heterocycloalkynyl, etc.) itself or the term combining with other terms respectively refers to a cyclic "hydrocarbonyl", "heterohydrocarbonyl". In addition, in terms of heterohydrocarbonyl or heterocyclohydrocarbonyl (such as heteroalkyl, heterocycloalkyl), heteroatoms can occupy the position where the heterocyclic ring is attached to the rest part of the molecule. Examples of the cycloalkyl include but not limited to cyclopentyl, cyclohexyl, 1-cyclohexenyl, 3-cyclohexenyl, cycloheptyl etc. Unrestricted examples of the heterocyclyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent. It can be monocyclic or polycyclic (preferably 1-3 rings). They fuse together or connect by a covalent linkage. The term "heteroaryl" refers to an aryl (or ring) containing 1-4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted examples of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

For simplicity, when used in combination with other terms (e.g. aryloxy, arylthio, aralkyl), the aryl includes the definition of aryl and heteroaryl ring defined above. Therefore, the term "aralkyl" is intended to include the groups that aryl attached to alkyl (e.g. benzyl, phenyl ethyl, pyridyl methyl), including those alkyls wherein carbon atoms (such as methylene) has been replaced by such as oxygen atoms, such as phenoxy methyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but not limited to "the protecting group of an amino", "the protecting group of a hydroxyl", or "the protecting group of a mercapto". The term "the protecting group of an amino" refers to a protecting group that is suitable for preventing side reactions occur at the nitrogen atom of an amino group. A representative protecting group of an amino includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl) methyl; silyl, such as trimethylsilyl (TMS) and tert-butyldimethylsilyl (TBS) and etc. The term "the protecting group of a hydroxyl" refers to a protecting group that is suitable for preventing side reactions of a hydroxyl group. A representative protecting group of a hydroxyl includes but not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

The compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

The solvents used in the present invention are commercially available, which can be used without further purification. The reactions are carried out under the inert nitrogen gas atmosphere with anhydrous solvents. The NMR spectra data are recorded by Bruker Avance III 400 (400 MHz) spectrometer, and the chemical shift (ppm) is calculated based on a reference signal of tetramethylsilane in low field. Mass spectrometry is measured by Agilent 1200 series and 6110 (&1956A). LC/MS or Shimadzu MS contain a DAD: SPD-M20A (LC) and Shimadzu Micromass 2020 detector. The mass spectrometer is equipped with an electrospray ionization (ESI) which can operated in positive-ion or negative-ion mode.

The present invention adopts the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents m-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; Cbz represents benzyloxycarbonyl, a protecting group of an amino; Boc represents tert-butoxycarbonyl, a protecting group of an amine; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluene sulfonic acid; NFSI represents N-fluorobenzenesulfonimide; NCS represents N-chlorosuccinimide; $n-Bu_4NF$ represents tetrabutylammonium fluoride; iPrOH represents 2-propanol; mp represents melting point; LDA represents lithium diisopropylamide; Pd(dppf)$_2$Cl$_2$ represents 1,1'-[bis(diphenylphosphino)ferrocene]dichloropalladium; (c-hex)$_3$P represents tricyclohexyl phosphate; (PinB)$_2$ represents bis(pinacolato)diboron; Ir(OMe)(COD)]$_2$ represents bis(1,5-cyclooctadiene)di-μ-methoxydiiridium (I); dtbpy represents 4,4'-di-tert-butyl-2,2'-dipyridine; NBS represents N-bromosuccinimide; DAST represents diethylaminosulphur trifluoride; DIEA represents N,N-diisopropylethylamine; DPPA represents diphenylphosphoryl azide; TsCl represents p-toluenesulfonyl chloride; HOBT represents 1-hydroxybenzotriazole; EDCI represents 1-ethyl-3-(3-dimethylaminopropyl)carbodiimide hydrochloride; PhSH represents thiophenol; DMAD represents dimethyl acetylenedicarboxylate.

Compounds are named manually or by software ChemDraw®, commercially available compounds are named in accordance with suppliers' catalogue.

DETAILED DESCRIPTION OF THE PREFERRED EMBODIMENT

The following examples further illustrate the present invention, but the present invention is not limited thereto.

Reference 1: Fragment BB-1

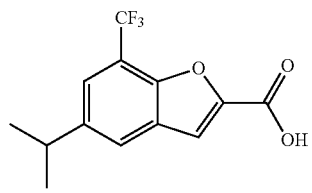

Synthetic Route:

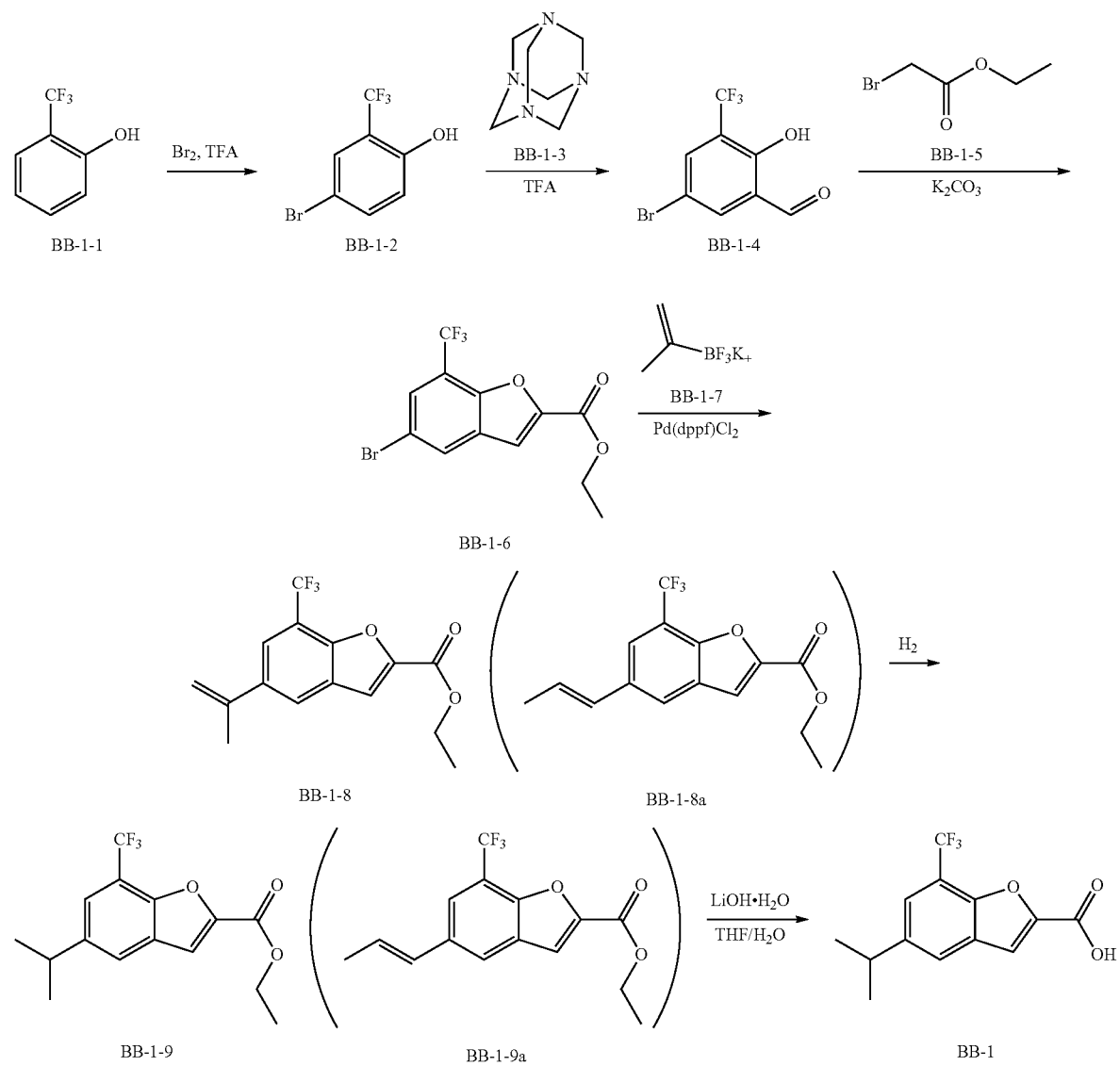

Step 1: Synthesis of Compound BB-1-2

Compound BB-1-1 (6.0 g, 37 mmol) was dissolved in TFA (30 mL), then liquid bromine (5.91 g, 37 mmol) was added dropwise slowly, the reactants were stirred at r.t. for 2 hours. After the reaction was complete, EA (200 mL) was added, the organic phases were washed with brine (50 mL×2), saturated sodium carbonate (50 mL×2), brine (50 mL), dried over sodium sulfate, concentrated to deliver the target compound BB-1-2 (gray solid, 8.9 g, yield: 100%). $^1$HNMR (400 MHz, CDCl$_3$): δ 7.63 (s, 1H), 7.52 (d, J=8.8 Hz, 1H), 6.88 (d, J=8.8 Hz, 1H), 6.09 (s, 1H).

Step 2: Synthesis of Compound BB-1-4

Compound BB-1-2 (1 g, 4.13 mmol) was dissolved in TFA (5 mL), then methenamine BB-1-3 (2.33 g, 16.6 mmol) was added. The reactants were heated to 90° C. in a stuffy can and stirred overnight. After cooling, water (20 mL) and 50% sulphuric acid (7 mL) were added, the mixture was further stirred for 1 hour, filtered, the solid was washed with water, dried to deliver the target compound BB-1-4 (gray solid, 0.60 g, yield 53.75%). $^1$HNMR (400 MHz, CDCl$_3$): δ 11.62 (s, 1H), 9.93 (s, 1H), 7.92 (s, 1H), 7.88 (s, 1H).

Step 3: Synthesis of Compound BB-1-6

Reactant BB-1-4 (0.60 g, 2.23 mmol) was dissolved in DMF (8 mL), then K$_2$CO$_3$ (0.925 g, 6.69 mmol), compound BB-1-5 (0.41 g, 2.45 mmol) were added. The reactants were heated to 100° C. and stirred for 2 hours. EA (50 mL) was added, the mixture was washed with brine (20 mL), dried, concentrated to deliver a crude product, which was purified by flash column chromatography (eluting agent, EA/PE=1/3) to deliver the target compound BB-1-6 (yellow solid, 0.35 g, yield 46.5%). MS (ESI) m/z: 337 [M+H]$^+$, 339 [M+H+2]$^+$.

Step 4: Synthesis of Compound BB-1-8 and BB-1-8a

Compound BB-1-6 (0.34 g, 1.01 mmol) was dissolved in isopropanol (5 mL), then potassium isopropenyltrifluoroborate BB-1-7 (0.194 g, 1.31 mmol), TEA (0.510 g, 5.04 mmol), 1,1'-[bis(diphenylphosphino)ferrocene]dichloropalladium (0.074 g, 0.101 mmol) were added. The reaction mixture was reacted for 3 hours under nitrogen gas atmosphere. After cooling, EA (100 mL) was added, the mixture was washed with brine (20 mL), dried over sodium sulfate, concentrated to deliver a crude product, which was purified by flash column chromatography (eluting agent, EA/PE=1/5) to deliver the target compound BB-1-8 and BB-1-8a (yellow oil, 0.295 g, yield 98%). MS (ESI) m/z: 299 [M+H]$^+$.

Step 5: Synthesis of Compound BB-1-9 and BB-1-9a

Compound BB-1-8 and BB-1-8a (0.295 g, 0.989 mmol) were dissolved in EA (15 mL), 10% Pd/C (0.03 g) was added, the reactants were stirred under hydrogen gas atmosphere at a pressure of 20 Psi for 4 hours at r.t. The reaction mixture was evaporated to dry to deliver the target compound BB-1-9 and BB-1-9a, which were used for the next step directly (gray solid, 0.295 g, yield 99%). MS (ESI) m/z: 301 [M+H]$^+$.

Step 6: Synthesis of Compound BB-1

Compound BB-1-9 (0.105 g, 0.35 mmol) was dissolved in THF/H$_2$O (3 mL, 2:1), lithium hydroxide hydrate (0.073 g, 1.75 mmol) was added. The reaction mixture was stirred at r.t. for 2 hours. After the reaction was complete, pH was adjusted to 1 with 2 M hydrochloric acid, then the mixture was extracted with EA (50 mL×2), dried over anhydrous sodium sulfate, filtered, concentrated to deliver the target compound BB-1 (gray solid, 0.093 g, yield 98%). MS (ESI) m/z: 273 [M+H]$^+$.

Reference 2: Fragment BB-2

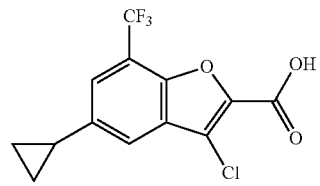

Synthetic Route:

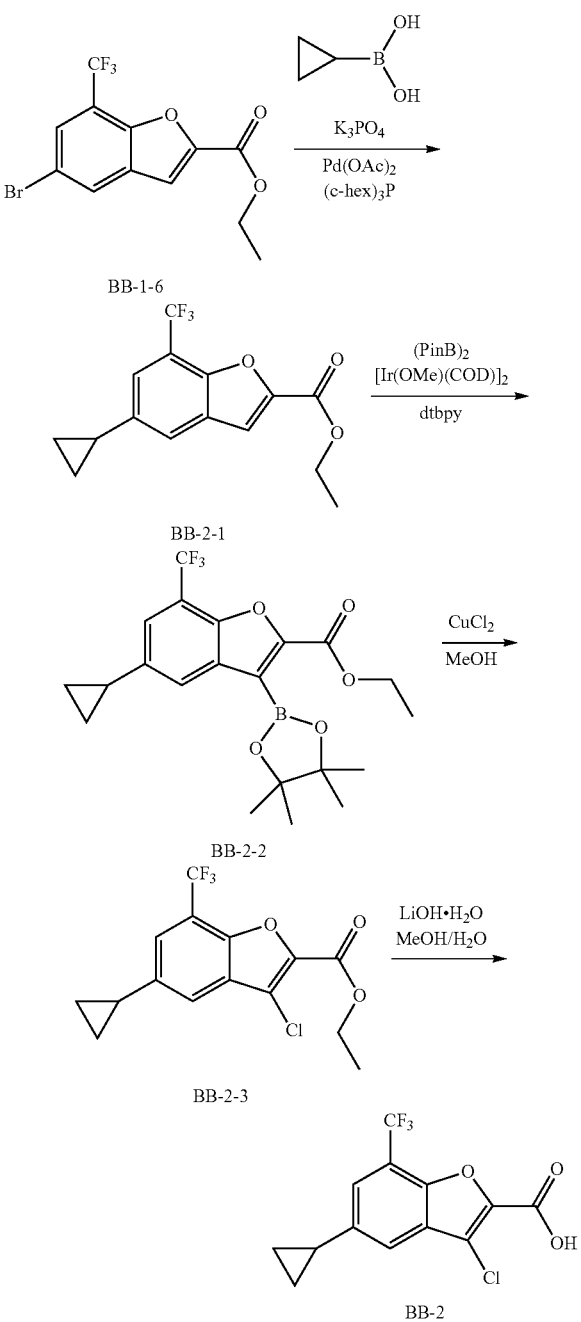

Step 1: Synthesis of Compound BB-2-1

Compound BB-1-6 (2 g, 5.93 mmol) was dissolved in toluene/H₂O (30 mL, 2:1), then cyclopropylboronic acid (1.02 g, 11.86 mmol), Pd(OAC)₂ (0.133 g, 0.593 mmol), tricyclohexyl phosphate (0.183 g, 0.652 mmol), K₃PO₄ (3.78 g, 17.79 mmol) were added sequentially. The reaction mixture was stirred at 100° C. for 3 hours. After cooling, EA (100 mL) was added, the organic phase was washed with brine (50 mL×2), dried over anhydrous sodium sulfate, filtered, concentrated to deliver a crude product, which was purified by flash column chromatography (eluting agent, EA/PE=1/10) to deliver the target compound BB-2-1 (yellow oil, 1.6 g, yield 90.4%). MS (ESI) m/z: 299 [M+H]⁺.

Step 2: Synthesis of Compound BB-2-2

Compound BB-2-1 (1.6 g, 5.36 mmol) was dissolved in n-hexane (30 mL), then bis(pinacolato)diboron (1.497 g, 5.896 mmol), di-μ-methoxobis(1,5-cyclooctadiene)diiridium(I) (0.216 g, 0.32 mmol), 4,4'-di-tert-butyl-2,2'-dipyridine (0.144 g, 0.536 mmol) were added sequentially. The reactants were refluxed for 2 hours under nitrogen gas atmosphere. The reaction mixture was evaporated to dry, then purified by flash column chromatography (eluting agent, EA/PE=1/10) to deliver the target compound BB-2-2 (white solid, 2.1 g, yield 92%). MS (ESI) m/z: 343 [M−82+H]⁺.

Step 3: Synthesis of Compound BB-2-3

Compound BB-2-2 (0.50 g, 1.18 mmol) was dissolved in methanol (8 mL), then CuCl₂ (0.317 g, 2.36 mmol) was added. The reaction mixture was heated to 50° C. and reacted for 16 h. After cooling, the reaction mixture was evaporated to dry, then purified by flash column chromatography (eluting agent, EA/PE=1/10) to deliver the target compound BB-2-3 (white solid, 0.310 g, yield 79%). MS (ESI) m/z: 333 [M+H]⁺.

Step 4: Synthesis of Compound BB-2

Compound BB-2-3 (0.31 g, 0.932 mmol) was dissolved in methanol/H₂O (6 mL, 2:1), then lithium hydroxide hydrate (0.156 g, 3.73 mmol) was added. After the reaction was complete, pH was adjusted to 1 with 2N hydrochloric acid, then the mixture was extracted with DCM, the combined organic phase was washed with brine, dried over anhydrous sodium sulfate, filtered, concentrated to deliver the target compound BB-2, which was used for the next step directly (white solid, 0.270 g, yield 95%). MS (ESI) m/z: 305 [M+H]⁺.

Reference 3: Fragment BB-3

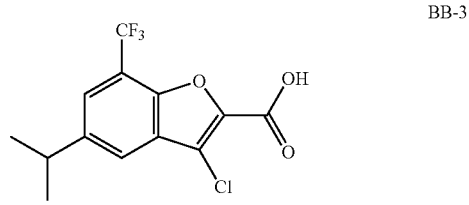 [SMILES: CC(C)c1cc(C(F)(F)F)c2oc(C(=O)O)c(Cl)c2c1]

BB-3

Synthetic Route:

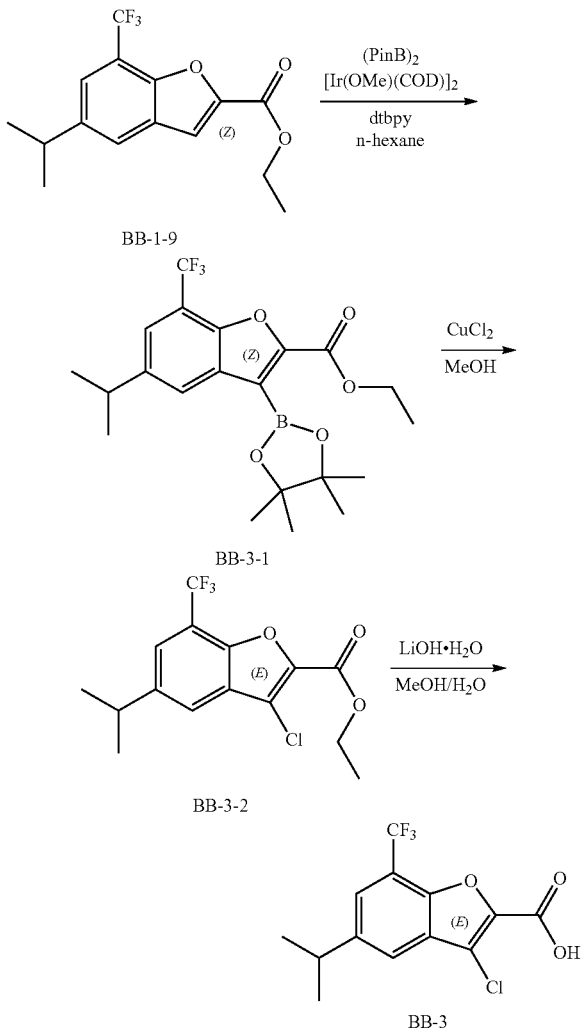

Step 1: Synthesis of Compound BB-3-1

Compound BB-1-9 (0.20 g, 0.666 mmol) was dissolved in n-hexane (3 mL), then bis(pinacolato)diboron (0.186 g, 0.763 mmol), di-μ-methoxobis(1,5-cyclooctadiene)diiridium(I) (0.028 g, 0.042 mmol), 4,4'-di-tert-butyl-2,2'-dipyridine (0.018 g, 0.067 mmol) were added sequentially, the reactants were refluxed for 16 hours under nitrogen gas atmosphere. After evaporated to dry, the mixture was purified by flash column chromatography (eluting agent, EA/PE=1/5) to deliver the target compound BB-3-1 (white solid, 0.20 g, yield 70%). MS (ESI) m/z: 345 [M−82+H]⁺.

Step 2: Synthesis of Compound BB-3-2

Compound BB-3-1 (0.20 g, 0.469 mmol) was dissolved in methanol (4 mL), then CuCl₂ (0.126 g, 0.938 mmol) was added, the reaction mixture was heated to 50° C. and reacted for 16 hours. After cooling, the reaction mixture was evaporated to dry, then purified by flash column chromatography (eluting agent, EA/PE=1/5) to deliver the target compound BB-3-2 (yellow solid, 0.140 g, yield 89%). MS (ESI) m/z: 335 [M+H]⁺.

Step 3: Synthesis of Compound BB-3

Compound BB-3-2 (0.130 g, 0.388 mmol) was dissolved in methanol/H₂O (5 mL, 2:1), then lithium hydroxide hydrate (0.081 g, 1.94 mmol) was added. The reaction mixture was stirred at r.t. for 2 hours. After the reaction was complete, pH was adjusted to 1 with 2N hydrochloric acid. And then the mixture was extracted with EA (50 mL×2), the combined organic phase was washed with brine (20 mL), dried over anhydrous sodium sulfate, filtered, concentrated to deliver the compound compound BB-3 (white solid, crude product, 0.119 g, yield 100%), which was used for the next step directly. MS (ESI) m/z: 307 [M+H]+.

Reference 3a: Fragment BB-3a

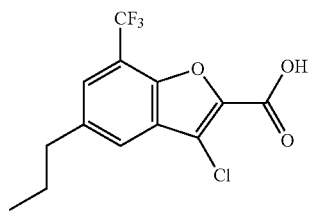

BB-3a

Reference 3a (fragment BB-3a) was synthesized according to the process for preparing fragment BB-3 in Reference 3, but the starting material was compound BB-1-9a. MS (ESI) m/z: 307 [M+H]+.

Reference 4: Fragment BB-4

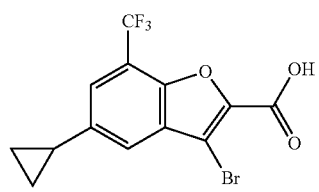

BB-4

Synthetic Route:

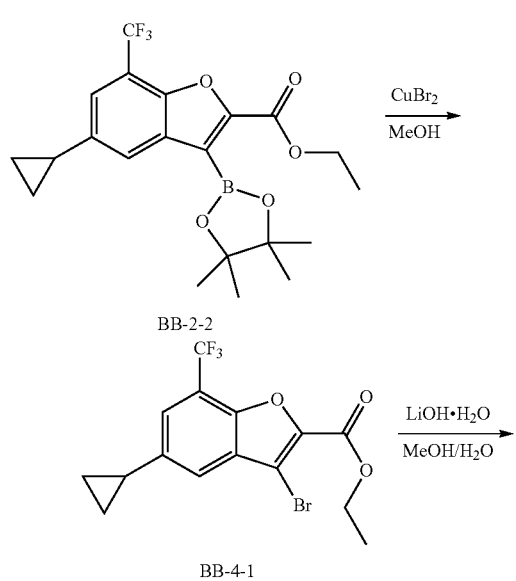

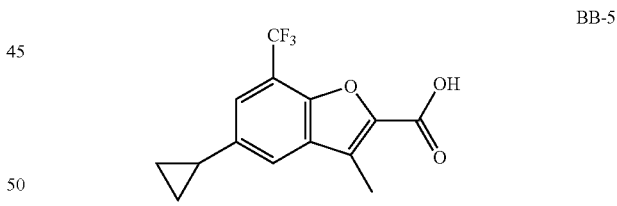

BB-4

Step 1: Synthesis of Compound BB-4-1

Compound BB-2-2 (0.30 g, 0.707 mmol) was dissolved in methanol (8 mL), then CuBr$_2$ (0.316 g, 1.41 mmol) was added, the reaction mixture was heated to 50° C. and reacted for 20 hours. After cooling, the reaction mixture was evaporated to dry to deliver a crude product, which was purified by flash column chromatography (eluting agent, EA/PE=1/10) to deliver the target compound BB-4-1 (gray solid, 0.22 g, yield 82%). MS (ESI) m/z: 377[M+H]+, 379[M+H+2]+.

Step 2: Synthesis of Compound BB-4

Compound BB-4-1 (0.120 g, 0.318 mmol) was added into methanol/H$_2$O (5 mL, 2:1), then lithium hydroxide monohydrate (0.089 g, 1.59 mmol) was added. After reacting for 2 hours at r.t., the reaction mixture was evaporated under reduced pressure, followed by adjusting pH to 1 with 2N hydrochloric acid, then the mixture was extracted with EA (25 mL×3), the organic phase was washed with saturated brine (20 mL), dried over anhydrous sodium sulfate, the solvent was removed under reduced pressure to deliver the target compound BB-4 (gray solid, 0.105 g, yield 95%). MS (ESI) m/z: 349 [M+H]+, 351 [M+H+2]+.

Reference 5: Fragment BB-5

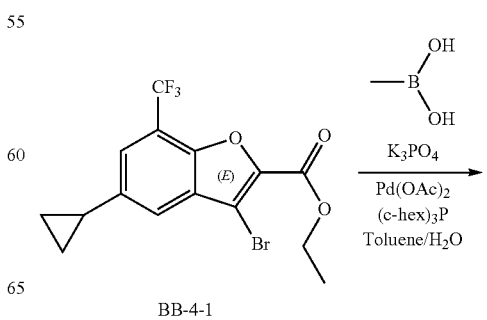

BB-5

Synthetic Route:

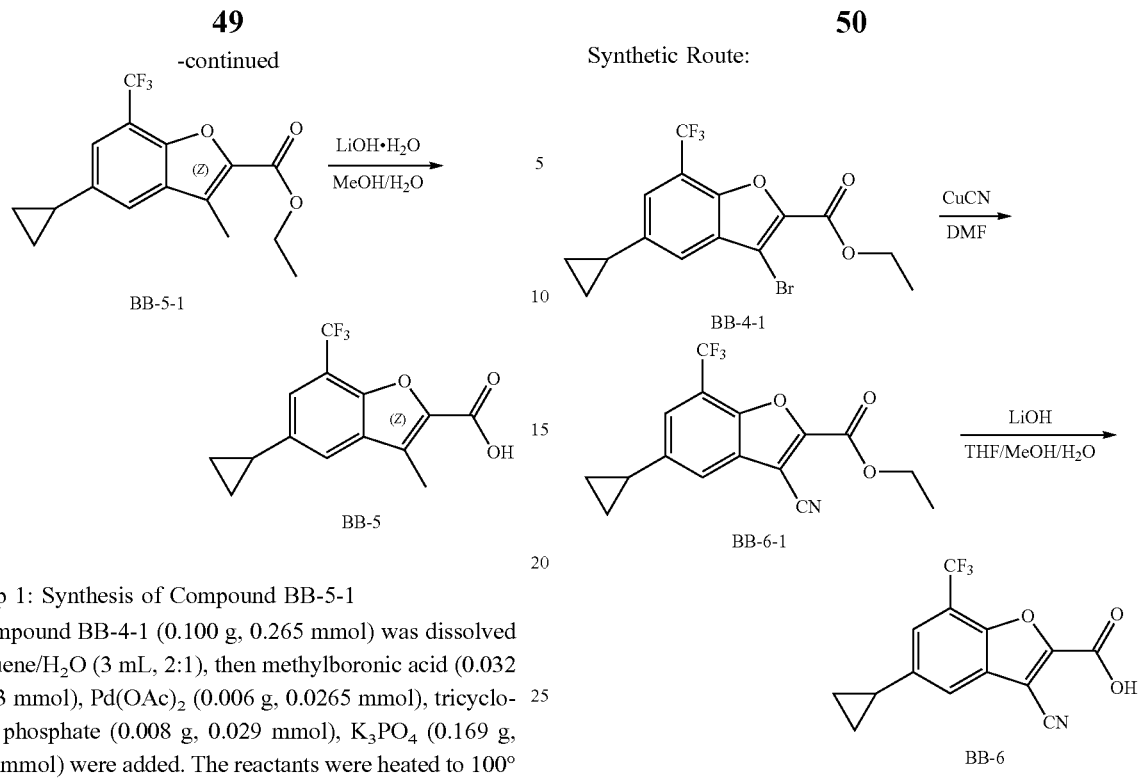

Step 1: Synthesis of Compound BB-5-1

Compound BB-4-1 (0.100 g, 0.265 mmol) was dissolved in toluene/H$_2$O (3 mL, 2:1), then methylboronic acid (0.032 g, 0.53 mmol), Pd(OAc)$_2$ (0.006 g, 0.0265 mmol), tricyclohexyl phosphate (0.008 g, 0.029 mmol), K$_3$PO$_4$ (0.169 g, 0.795 mmol) were added. The reactants were heated to 100° C. and stirred for 16 hours. The reaction mixture was cooled and EA (100 mL) was added, the organic phase was washed with brine (20 mL), dried over anhydrous sodium sulfate, filtered, and concentrated to deliver a crude product which was purified by thin silica gel plate (developing agent, EA/PE=1/6) to deliver the target compound BB-5-1 (gray solid, 0.075 g, yield 90.6%). MS (ESI) m/z: 313 [M+H]$^+$.

Step 2: Synthesis of Compound BB-5

Compound BB-5-1 (0.075 g, 0.24 mmol) was dissolved in methanol/H$_2$O (3 mL, 2:1), then lithium hydroxide hydrate (0.040 g, 0.96 mmol) was added. The reaction mixture was stirred at r.t. for 2 hours. After the reaction was complete, pH was adjusted to 1 with 2N hydrochloric acid, then the mixture was extracted with DCM (50 mL×2), the combined organic phase was washed with brine (20 mL), dried over anhydrous sodium sulfate, filtered, and concentrated to deliver the target compound BB-5 (gray solid, 0.067 g, yield 98%) which was used for the next step directly. MS (ESI) m/z: 285 [M+H]$^+$.

Reference 6: Fragment BB-6

Step 1: Synthesis of Compound BB-6-1

Compound BB-4-1 (0.160 g, 0.424 mmol) was dissolved in DMF (3 mL), then CuCN (0.152 g, 1.7 mmol) was added, the reaction mixture was reacted at 160° C. for 4 hours. After the mixture was cooling, EA (50 mL) was added, the organic phase was washed with brine (20 mL), dried over anhydrous sodium sulfate, filtered, and concentrated to deliver a crude product which was purified by thin silica gel plate (developing agent, EA/PE=1/3) to deliver the target compound BB-6-1 (gray solid, 0.040 g, yield 29%). MS (ESI) m/z: 324 [M+H]$^+$.

Step 2: Synthesis of Compound BB-6

Compound BB-6-1 (0.040 g, 0.124 mmol) was dissolved in THF/MeOH/H$_2$O (3 mL, 1:1:1), then lithium hydroxide hydrate (0.021 g, 0.495 mmol) was added. The reaction mixture was stirred at r.t. and reacted for 2 hours. After the reaction was complete, pH was adjusted to 1 with 6N hydrochloric acid, then the mixture was extracted with EA (50 mL×2), the combined organic phase was washed with brine (20 mL), dried over anhydrous sodium sulfate, filtered, and concentrated to deliver the target compound BB-6 (gray solid, 0.036 g, yield 98.6%) which was used for the next step directly. MS (ESI) m/z: 296 [M+H]$^+$.

Reference 7: Fragment BB-7

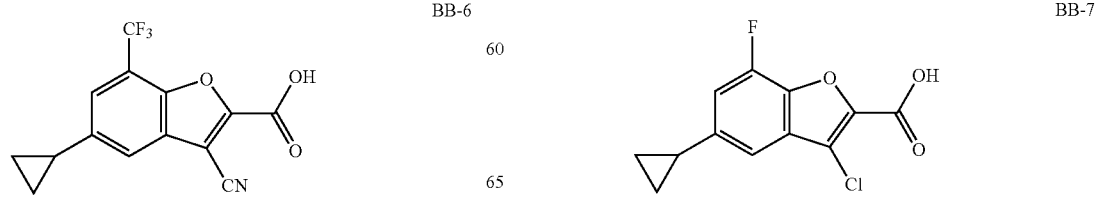

Synthetic Route:

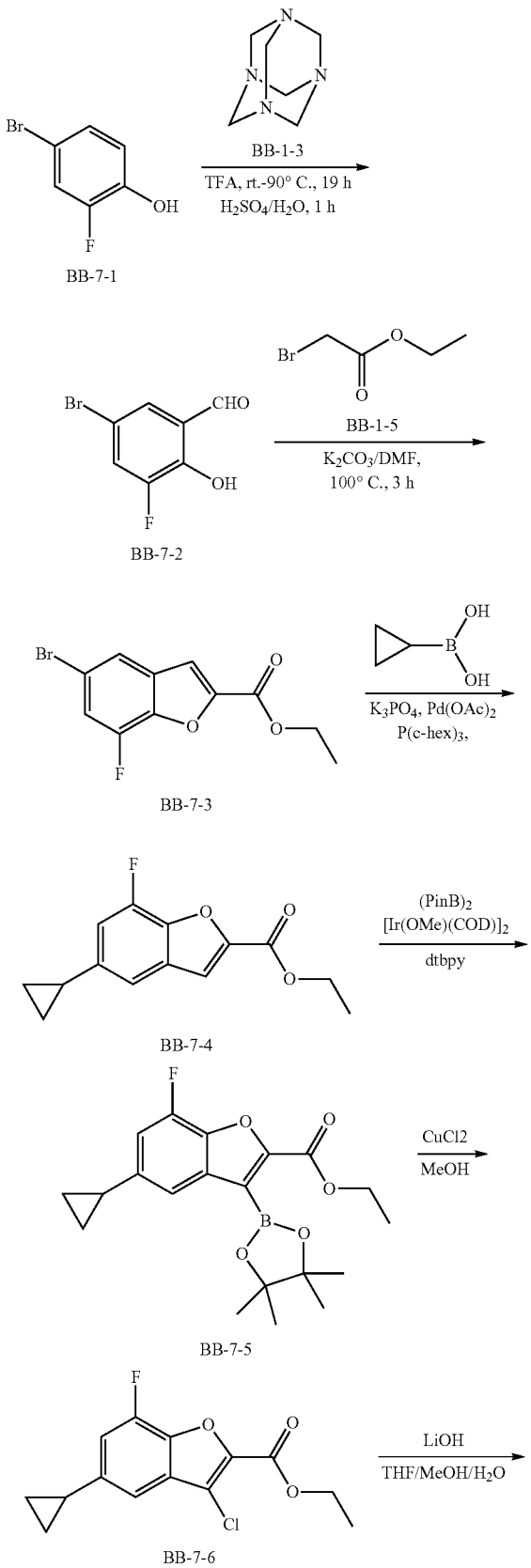

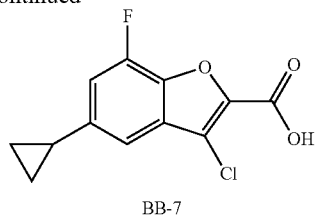

Step 1: Synthesis of Compound BB-7-2

Compound BB-7-1 (5 g, 26.18 mmol) was dissolved in TFA (5 mL), then under nitrogen gas atmosphere, compound BB-1-3 (7.34 g, 52.36 mmol) was added in portions. The reactants were stirred at r.t. for 20 minutes, then heated to 90° C. and reacted overnight. After cooling, H$_2$O (30 mL) and 50% sulphuric acid (15 mL) were added, the mixture was stirred for 2 hours, filtered, and dried to deliver the target compound BB-7-2 (brown solid, 3.5 g, yield 61%). $^1$H NMR (400 MHz, CDCl$_3$): δ 10.85 (br. s., 1H), 9.84-9.89 (m, 1H), 7.45-7.53 (m, 2H).

Step 2: Synthesis of Compound BB-7-3

Compound BB-7-2 (1 g, 4.57 mmol) was dissolved in DMF (12 mL), then K$_2$CO$_3$ (1.89 g, 13.7 mmol), ethyl bromoacetate (0.838 g, 5.02 mmol) were added. The reaction mixture was heated to 100° C. and reacted for 2 hours. After cooling, EA (100 mL) was added. The organic phase was washed with brine (20 mL×2), dried over anhydrous sodium sulfate, filtered, and concentrated to deliver a crude product which was purified by flash column chromatography (eluting agent, EA/PE=1/3) to deliver the target compound BB-7-3 (yellow solid, 0.400 g, yield 30%). $^1$H NMR (400 MHz, CDCl$_3$): δ 7.61 (s, 1H), 7.48 (d, J=3.01 Hz, 1H), 7.34 (dd, J=9.54, 1.51 Hz, 1H), 4.46 (q, J=7.03 Hz, 2H), 1.43 (t, J=7.03 Hz, 3H).

Step 3: Synthesis of Compound BB-7-4

Compound BB-7-3 (0.287 g, 1 mmol) was dissolved in toluene/H$_2$O (5 mL, 2:1), then cyclopropylboronic acid (0.172 g, 2 mmol), Pd(OAc)$_2$ (0.022 g, 0.1 mmol), tricyclohexyl phosphate (0.028 g, 0.1 mmol), K$_3$PO$_4$ (0.637 g, 3 mmol) were added. The reactants were heated to 100° C. and reacted for 4 hours. After cooling, EA (100 mL) was added, the organic phase was washed with brine (20 mL×2), dried over anhydrous sodium sulfate, filtered, and concentrated to deliver a crude product, which was purified by flash column chromatography (eluting agent, EA/PE=1/6) to deliver the target compound BB-7-4 (gray solid, 0.240 g, yield 96.7%). MS (ESI) m/z: 249 [M+H]$^+$.

Step 4: Synthesis of Compound BB-7-5

Compound BB-7-4 (0.080 g, 0.322 mmol) was dissolved in n-hexane (3 mL), then (PinB)$_2$ (0.106 g, 0.419 mmol), di-g-methoxobis(1,5-cyclooctadiene)diiridium(I) (0.015 g, 0.022 mmol), 4,4'-di-tert-2,2'-bipyridine (0.009 g, 0.032 mmol) were added sequentially, the reactants were refluxed under nitrogen gas atmosphere for 16 hours. The reaction mixture was evaporated to dry, then purified by thin silica gel plate (developing agent, EA/PE=1/3) to deliver the target compound BB-7-5 (white solid, 0.070 g, yield 58%). MS (ESI) m/z: 293 [M−82+H]$^+$.

Step 5: Synthesis of Compound BB-7-6

Compound BB-7-5 (0.070 g, 0.187 mmol) was dissolved in methanol (3 mL), then CuCl$_2$ (0.05 g, 0.374 mmol) was added, the reaction mixture was heated to 50° C. and reacted for 20 hours. After cooling, the reaction mixture was evaporated to dry, then EA (50 mL) was added, the organic phase was washed with brine (20 mL), dried over sodium sulfate, filtered, and concentrated to deliver the target compound BB-7-6 (gray solid, 0.052 g, yield 98%) which was used for the next step directly. MS (ESI) m/z: 283 [M+H]+.

Step 6: Synthesis of Compound BB-7

Compound BB-7-6 (0.052 g, 0.184 mmol) was dissolved in THF/MeOH/H$_2$O (4 mL, 2:1:1), then lithium hydroxide hydrate (0.039 g, 0.92 mmol) was added. The reaction mixture was stirred at r.t. for 2 hours. After the reaction was complete, pH was adjusted to 1 with 2N hydrochloric acid, then the mixture was extracted with EA (50 mL×2), the combined organic phase was washed with brine (20 mL), dried over anhydrous sodium sulfate, filtered, and concentrated to deliver the target compound BB-7 (gray solid, 0.045 g, yield 96%) which was used for the next step directly. MS (ESI) m/z: 255 [M+H]+.

Reference 8: Fragment BB-8

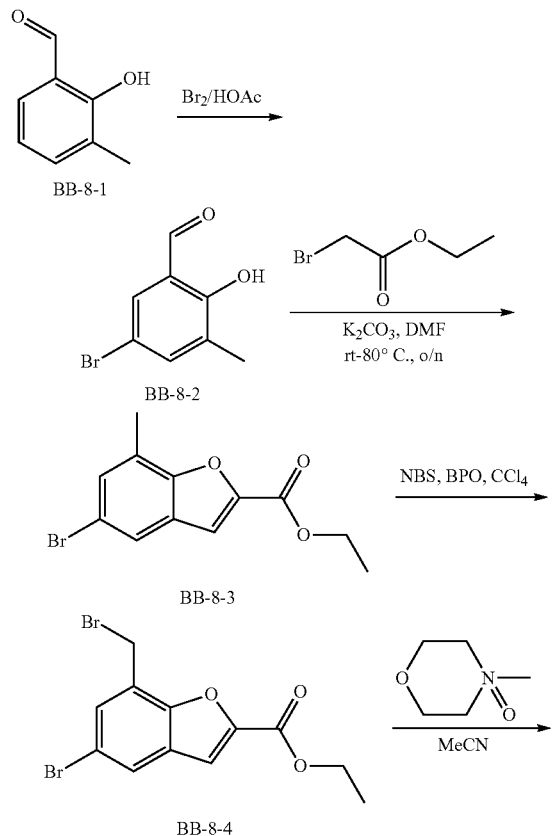

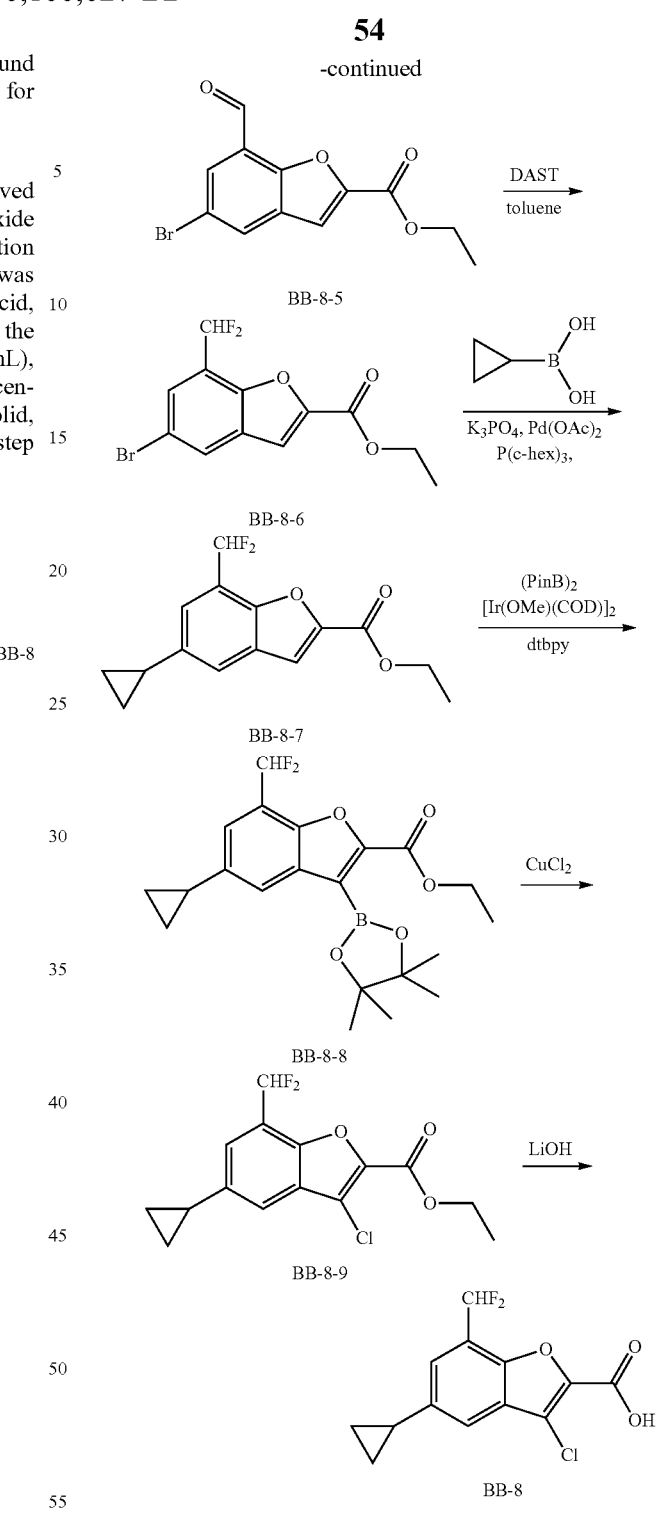

Step 1: Synthesis of Compound BB-8-2

Compound BB-8-1 (5 g, 36.72 mmol) was dissolved in HOAc (30 mL), the mixture was cooled to 0° C., then liquid bromine (6.75 g, 42.23 mmol) was added dropwise, the resulting mixture was reacted at 0° C. for 2 hours. After the reaction was complete, H$_2$O (100 mL) was added, the mixture was filtered, the solid was washed with H$_2$O, and dried to deliver the target compound BB-8-2 (yellow solid, 7.5 g, yield 95%). $^1$H NMR (400 MHz, CDCl$_3$): δ 11.18 (s, 1H), 9.81 (s, 1H), 7.51-7.47 (m, 2H), 2.25 (s, 3H).

Step 2: Synthesis of Compound BB-8-3

Compound BB-8-2 (5.4 g, 25.11 mmol) was dissolved in DMF (70 mL), then K$_2$CO$_3$ (6.94 g, 50.22 mmol), ethyl bromoacetate (5.03 g, 30.13 mmol) were added. The reaction mixture was reacted at r.t. for 1 hour, then heated to 80° C. and reacted for 16 hours. After cooling, EA (50 mL) was added, the organic phase was washed with brine (20 mL), dried over anhydrous sodium sulfate, filtered, and concentrated to deliver a crude product, which was purified by flash column chromatography (eluting agent, EA/PE=1/6) to deliver the target compound BB-8-3 (white solid, 4.2 g, yield 59%). MS (ESI) m/z: 283 [M+H]$^+$, 285[M+H+2]$^+$.

Step 3: Synthesis of Compound BB-8-4

Compound BB-8-3 (0.50 g, 1.77 mmol) was dissolved in CCl$_4$ (7 mL), then NBS (0.377 g, 2.12 mmol), benzoperoxide (0.043 g, 0.177 mmol) were added. The reaction mixture was reacted at 80° C. for 16 h. The reaction mixture was concentrated to deliver a crude product, which is purified by flash column chromatography (eluting agent, EA/PE=1/6) to deliver the target compound BB-8-4 (gray solid, 0.660 g, crude product). MS (ESI) m/z: 363 [M+H]$^+$, 361[M+H−2]$^+$, 365[M+H+2]$^+$.

Step 4: Synthesis of Compound BB-8-5

Compound BB-8-4 (0.30 g, 0.829 mmol) was dissolved in acetonitrile (10 mL), then N-methylmorpholine-N-oxide (0.970 g, 8.29 mmol) was added. The reaction mixture was stirred at r.t. for 4 hours, then evaporated to dry. EA (50 mL) was added, the organic phase was washed with brine (20 mL), dried over anhydrous sodium sulfate, filtered, and concentrated to deliver the crude product, which was purified by flash column chromatography (eluting agent, EA/PE=1/5) to deliver the target compound BB-8-5 (white solid, 0.180 g, 73.11%). MS (ESI) m/z: 297 [M+H]$^+$, 299[M+H+2]$^+$.

Step 5: Synthesis of Compound BB-8-6

Compound BB-8-5 (0.170 g, 0.572 mmol) was dissolved in toluene (2 mL), then diethylaminosulphur trifluoride (0.185 g, 1.15 mmol) was added, the reactants were stirred at 25° C. for 16 hours under nitrogen gas atmosphere. After the reaction was complete, EA (50 mL) was added, the organic phase was washed with brine (20 mL), dried over anhydrous sodium sulfate, filtered, and concentrated to deliver a crude product, which was purified by flash column chromatography (eluting agent, EA/PE=1/6) to deliver the target compound BB-8-6 (gray solid, 0.175 g, 95.84%). MS (ESI) m/z: 319 [M+H]$^+$, 321[M+H+2]$^+$.

Step 6: Synthesis of Compound BB-8-7

Compound BB-8-6 (0.170 g, 0.533 mmol) was dissolved in toluene (3 mL) and H$_2$O (1 mL), then tricyclohexyl phosphate (0.015 g, 0.053 mmol), cyclopropylboronic acid (0.10 g, 1.16 mmol), Pd(OAc)$_2$ (0.012 g, 0.053 mmol) were added, the reactants were heated to 110° C. and stirred for 5 hours under nitrogen gas atmosphere. After cooling, EA (50 mL) was added, the organic phase was washed with brine (20 mL), dried over anhydrous sodium sulfate, filtered, and concentrated to deliver a crude product, which was purified by flash column chromatography (eluting agent, EA/PE=1/5) to deliver the target compound BB-8-7 (yellow solid, 0.132 g, 88.40%). MS (ESI) m/z: 281 [M+H]$^+$.

Step 7: Synthesis of Compound BB-8-8

Compound BB-8-7 (0.132 g, 0.471 mmol) was dissolved in n-hexane (3 mL), then (PinB)$_2$ (0.145 g, 0.571 mmol), 4,4'-di-tert-2,2'-bipyridine (0.013 g, 0.048 mmol), di-g-methoxobis(1,5-cyclooctadiene)diiridium(I) (0.019 g, 0.029 mmol) were added sequentially, the reactants were refluxed under nitrogen gas atmosphere for 16 hours. The reaction mixture was evaporated to dry, purified by flash column chromatography (eluting agent, EA/PE=1/5) to deliver the target compound BB-8-8 (white solid, 0.10 g, 52.27%). MS (ESI) m/z: 325 [M−82+H]$^+$.

Step 8: Synthesis of Compound BB-8-9

Compound BB-8-8 (0.095 g, 0.234 mmol) was dissolved in methanol (4 mL), then CuCl$_2$ (0.063 g, 0.468 mmol) was added, the reaction mixture was heated to 50° C. and reacted for 16 hours. After cooling, the reaction mixture was evaporated to dry, then EA (50 mL) was added. The organic phase was washed with brine (20 mL), dried over sodium sulfate, filtered, and concentrated to deliver the target compound BB-8-9 (white solid, 0.073 g, 99.19%), which was used for the next step directly. MS (ESI) m/z: 315 [M+H]$^+$.

Step 9: Synthesis of Compound BB-8

Compound BB-8-9 (0.070 g, 0.222 mmol) was dissolved in methanol (2 mL) and H$_2$O (2 mL), then lithium hydroxide hydrate (0.050 g, 1.19 mmol) was added, the reaction mixture was stirred at r.t. for 3 hours. After the reaction was complete, pH was adjusted to 1 with 3N hydrochloric acid, then the mixture was extracted with EA (50 mL×2), the combined organic phase was washed with brine (20 mL), dried over anhydrous sodium sulfate, filtered, and concentrated to deliver the target compound BB-8 (white solid, 0.063 g, 98.81%), which was used for the next step directly. MS (ESI) m/z: 287 [M+H]$^+$.

Reference 9: Fragment BB-9

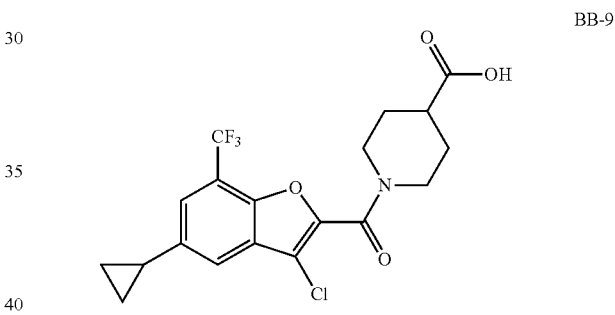

BB-9

Synthetic Route:

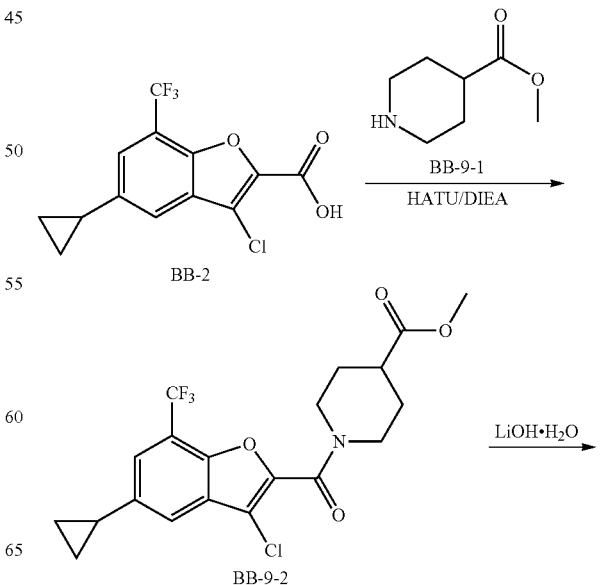

-continued

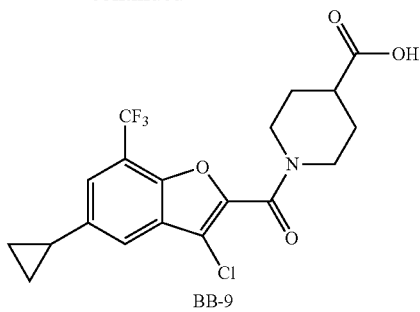

BB-9

Step 1: Synthesis of Compound BB-9-2

Compound BB-2 (0.30 g, 0.98 mmol), compound BB-9-1 (0.141 g, 0.98 mmol), HATU (0.449 g, 1.18 mmol) and DIPEA (0.382 g, 2.95 mmol) were dissolved in anhydrous DMF (3 mL), stirred at 20° C. for 6 hours, H$_2$O was added, the mixture was extracted with EA (20 mL×2). The combined organic phase was washed with saturated brine (20 mL), dried over anhydrous sodium sulfate, and the solvent was removed under reduced pressure to deliver compound BB-9-2 (yellow oil, 0.460 g, yield 100%), which was used for the next step directly without purification. MS (ESI) m/z: 430.2 [M+H]$^+$.

Step 2: Synthesis of Compound BB-9

Compound BB-9-2 (0.460 g, 1.07 mmol) was dissolved in THF:methanol:H$_2$O=2:2:1 (10 mL), lithium hydroxide monohydrate (0.135 g, 3.21 mmol) was added. The reaction mixture was stirred at 18° C. for 2 hours, the solvent was removed under reduced pressure, the residue was dissolved in H$_2$O again, pH was adjusted to about 2-3 with 2N aqueous hydrochloric acid solution, the solid was collected to deliver the compound BB-9 (white solid, 0.380 g, yield 85.4%) which was used for the next step directly without purification. MS (ESI) m/z: 416 [M+H]$^+$.

Reference 9a: Fragment BB-9a

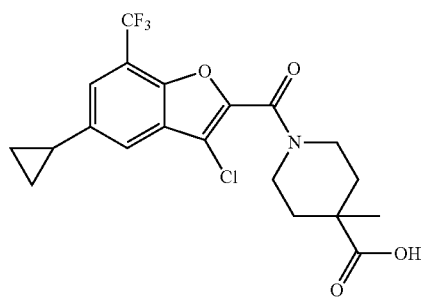

BB-9a

Synthetic Route:

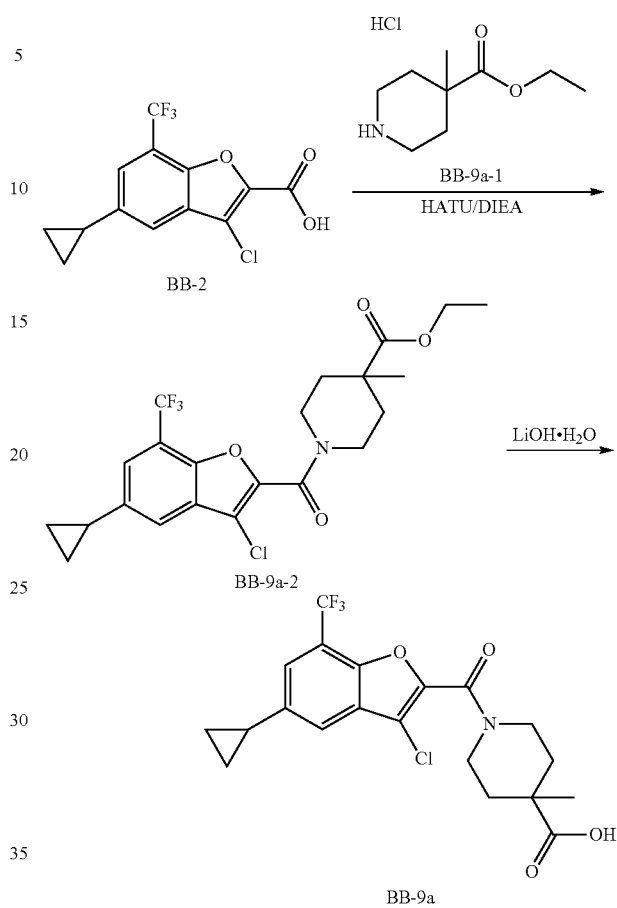

Step 1: Synthesis of Compound BB-9a-2

Compound BB-2 (0.147 g, 0.483 mmol), compound BB-9a-1 (0.100 g, 0.483 mmol) were dissolved in DMF (1 mL), DIPEA (0.187 g, 1.45 mmol) and HATU (0.275 g, 0.724 mmol) were added. The reaction mixture was stirred at 18° C. for 2 hours, H$_2$O (3 mL) was added, the mixture was extracted with EA (20 mL×3). The organic phases were combined, washed with H$_2$O (20 mL×2) and saturated brine (20 mL), dried over anhydrous sodium sulfate, filtered, and concentrated to deliver compound BB-9a-2 (yellow solid, 0.220 g, yield 99.58%). MS (ESI) m/z: 458 [M+H]$^+$.

Step 2: Synthesis of Compound BB-9a

Compound BB-9a-2 (0.220 g, 0.480 mmol) was dissolved in methanol (5 mL), lithium hydroxide monohydrate (0.101 g, 2.40 mmol) and H$_2$O (1 mL) were added. The reaction mixture was stirred at 25° C. for 16 hours, then the solvent was removed under reduced pressure, the residue was dissolved in H$_2$O again, pH was adjusted to 3 with conc. hydrochloric acid. The mixture was filtered, the cake was dissolved in DCM (20 mL), dried over anhydrous sodium sulfate, filtered, and concentrated to deliver compound BB-9a (yellow solid, 0.150 g, yield 72.63%). MS (ESI) m/z: 430 [M+H]$^+$.

Reference 10: Fragment BB-10

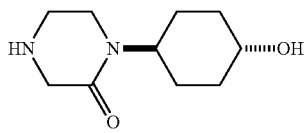

Synthetic Route:

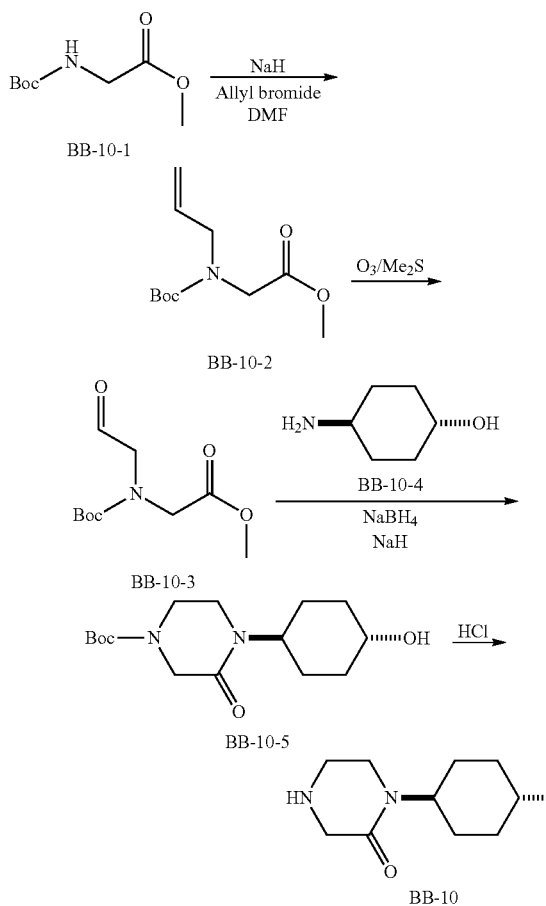

Step 1: Synthesis of Compound BB-10-2

Compound BB-10-1 (10.0 g, 52.85 mmol) was dissolved in DMF (120 mL), allyl bromide (7.67 g, 63.42 mmol) was added, and then NaH (3.17 g, 79.28 mmol, 60%) was added in portions at 0° C., the reaction mixture was stirred at 0° C. for 2 hours. After the reaction was complete, it was quenched with $H_2O$. The mixture was extracted with EA (50 mL×2), the organic phase was washed with brine (20 mL), dried over anhydrous sodium sulfate, filtered, and concentrated to deliver a crude product which was purified by flash column chromatography (eluting agent, EA/PE=1/6) to deliver the target compound BB-10-2 (gray solid, 9.3 g, yield 76.7%). MS (ESI) m/z: 230 [M+H]+.

Step 2: Synthesis of Compound BB-10-3

Compound BB-10-2 (9 g, 39.25 mmol) was dissolved in methanol (200 mL), cooled to −78° C., $O_3$ was introduced until the reaction mixture became blue, then $N_2$ was introduced until the reaction mixture became colorless, $Me_2S$ (15 mL, 203 mmol) was then added, the mixture was reacted at r.t. overnight. After the reaction was complete, the mixture was concentrated, EA (150 mL) was added, the organic phase was washed with brine (50 mL×2), dried over anhydrous sodium sulfate, filtered, and concentrated to deliver the target compound BB-10-3 (yellow oil, 9.1 g, yield 100%). MS (ESI) m/z: 232 [M+H]+.

Step 3: Synthesis of Compound BB-10-5

Compound BB-10-3 (6.35 g, 27.46 mmol) was dissolved in methanol (100 mL), then BB-10-4 (5.0 g, 32.95 mmol), DIPEA (4.26 g, 32.95 mmol), $Na_2SO_4$ (20 g) were added, the reaction mixture was stirred at r.t. for 1 hour, then $NaBH_4$ (1.25 g, 32.95 mmol) was added, the reaction mixture was stirred at r.t. for 2 hours. Then NaH (2.2 g, 54.92 mmol, 60%) was added in portions, the reaction mixture was stirred at r.t. for 1 hour. The reaction mixture was concentrated, EA (200 mL) was added, the organic phase was washed with brine (50 mL×2), dried over anhydrous sodium sulfate, filtered, and concentrated to deliver a crude product which was then recrystallized (EA/PE=1/5) to deliver the target compound BB-10-5 (yellow solid, 5.58 g, yield 67%). MS (ESI) m/z: 299 [M+H]+.

Step 4: Synthesis of Compound BB-10

Compound BB-10-5 (5.5 g, 18.43 mmol) was dissolved in DCM (20 mL), then hydrochloric acid/dioxane (50 mL, 4 N) was added. The reaction mixture was stirred at r.t. for 3 hours. After the reaction was complete, the mixture was concentrated to deliver the target compound BB-10 (yellow solid, 4.4 g, yield 100%). MS (ESI) m/z: 199 [M+H]+.

Reference 11: Fragment BB-11

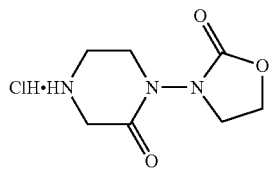

Synthetic Route:

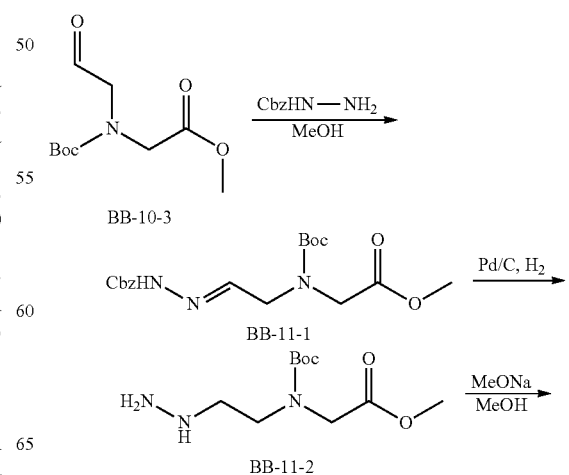

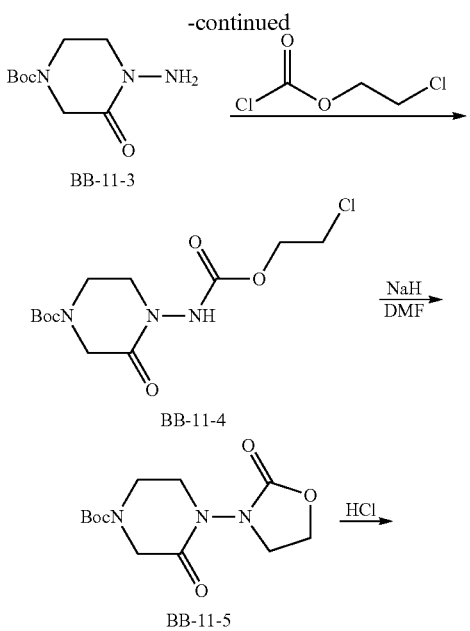

Step 1: Synthesis of Compound BB-11-1

Compound BB-10-3 (0.450 g, 1.95 mmol) was dissolved in methanol (5 mL), then benzyl carbazate (0.356 g, 2.14 mmol), Na$_2$SO$_4$ (0.50 g) were added, the reactants were stirred at r.t. for 2 hours. The reaction mixture was filtered, the filtrate was concentrated to deliver the target compound BB-11-1 (gray solid, 0.740 g, yield 100%). MS (ESI) m/z: 402 [M+Na]$^+$.

Step 2: Synthesis of Compound BB-11-2

Compound BB-11-1 (0.22 g, 0.58 mmol) was dissolved in methanol (10 mL), then Pd(OH)$_2$/C (0.020 g) was added, the reactants were stirred at r.t. for 3 hours under hydrogen gas atmosphere (15 Psi). The reaction mixture was filtered, the filtrate was concentrated to deliver the target compound BB-11-2 (gray solid, 0.110 g, yield 76.7%).

Step 3: Synthesis of Compound BB-11-3

Compound BB-11-2 (0.110 g, 0.445 mmol) was dissolved in methanol (3 mL), then MeONa (0.048 g, 0.889 mmol) was added, the reactants were stirred at r.t. for 2 hours. After the reaction was complete, it was quenched by adding H$_2$O dropwise, the mixture was extracted with EA (50 mL×2), the organic phase was washed with brine (20 mL), dried over anhydrous sodium sulfate, filtered, and concentrated to deliver the target compound BB-11-3 (yellow oil, 0.090 g, yield 94%). MS (ESI) m/z: 160 [M-$^t$Bu+H]$^+$.

Step 4: Synthesis of Compound BB-11-4

Compound BB-11-3 (0.090 g, 0.418 mmol) was dissolved in DCM (3 mL), then 2-chloroethyl chloroformate (0.072 g, 0.502 mmol), DIPEA (0.162 g, 1.25 mmol) were added, the reactants were stirred at 0° C. for 3 hours. After the reaction was complete, DCM (100 mL) was added, the organic phase was washed with brine (20 mL), dried over anhydrous sodium sulfate, filtered, and concentrated to deliver the target compound BB-11-4 (yellow solid, 0.110 g, yield 74.3%). MS (ESI) m/z: 322 [M+H]$^+$.

Step 5: Synthesis of Compound BB-11-5

Compound BB-11-4 (0.100 g, 0.31 mmol) was dissolved in DMF (3 mL), then NaH (0.025 g, 0.62 mmol) was added, the reactants were stirred at r.t. for 2 hours. After the reaction was complete, it was quenched by adding H$_2$O dropwise, the mixture was extracted with EA (50 mL×2), the organic phase was washed with brine (20 mL), dried over anhydrous sodium sulfate, filtered, and concentrated to deliver the target compound BB-11-5 (yellow oil, 0.080 g, yield 90.2%). MS (ESI) m/z: 308 [M+Na]$^+$.

Step 6: Synthesis of Compound BB-11

Compound BB-11-5 (0.080 g, 0.28 mmol) was dissolved in DCM (2 mL), then hydrochloric acid/dioxane (3 mL, 4 N) was added, the reactants were stirred at r.t. for 2 hours. The reaction mixture was concentrated to deliver the target compound BB-11 which was used for the next step directly (gray solid, 0.064 g, yield 100%). MS (ESI) m/z: 186 [M+H]$^+$.

Reference 12: Fragment BB-12

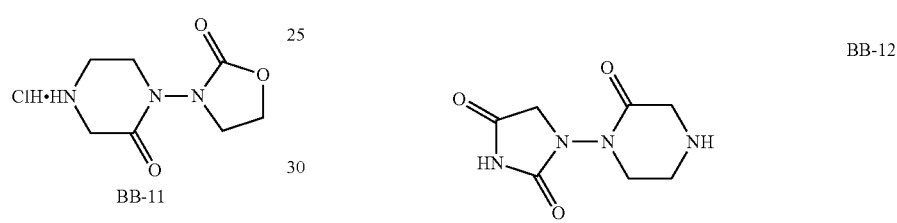

Synthetic Route:

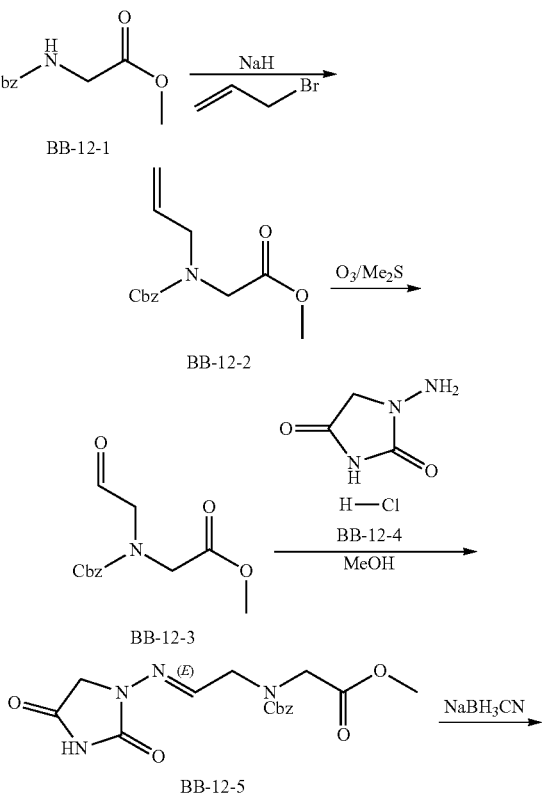

-continued

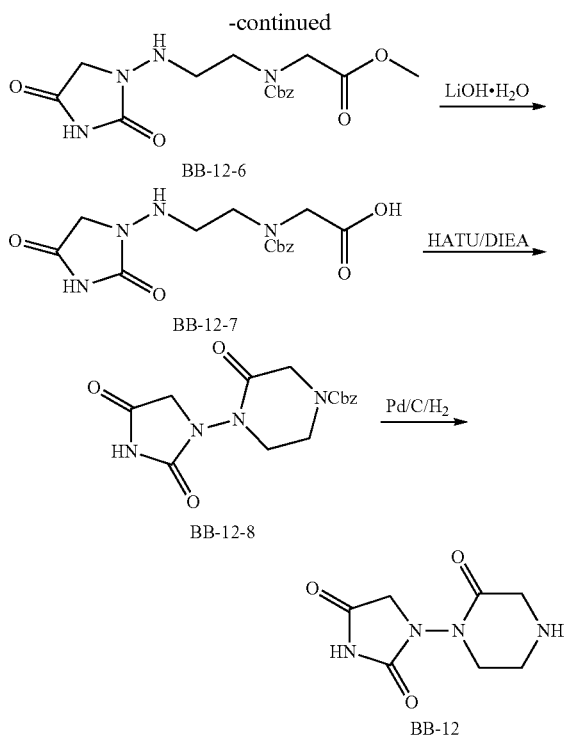

BB-12-6

BB-12-7

BB-12-8

BB-12

Step 1: Synthesis of Compound BB-12-2

Compound BB-12-1 (15.0 g, 67.20 mmol) was dissolved in DMF (170 mL), allyl bromide (9.76 g, 80.64 mmol) was added, and then at 0° C., NaH (3.23 g, 80.64 mmol, 60%) was added in portions, the reaction mixture was stirred at 0° C. for 2 hours. After the reaction was complete, it was quenched by adding $H_2O$, the mixture was extracted with EA (150 mL×2), the organic phase was washed with brine (50 mL), dried over anhydrous sodium sulfate, filtered, and concentrated to deliver the crude product which was purified by flash column chromatography (eluting agent, EA/PE=1/6) to deliver the target compound BB-12-2 (gray solid, 12.0 g, yield 67.83%). MS (ESI) m/z: 264 [M+H]+.

Step 2: Synthesis of Compound BB-12-3

Compound BB-12-2 (12 g, 45.58 mmol) was dissolved in methanol (250 mL), cooled to −78° C., $O_3$ was introduced until the reaction mixture became blue, then $N_2$ was introduced until the reaction mixture became colorless, $Me_2S$ (15 mL, 203 mmol) was then added, the reaction mixture was stirred overnight. After the reaction was complete, the mixture was concentrated, EA (250 mL) was added, the organic phase was washed with brine (50 mL×2), dried over anhydrous sodium sulfate, filtered, and concentrated to deliver the target compound BB-12-3 (yellow oil, 12 g, yield 99.26%). MS (ESI) m/z: 266 [M+H]+.

Step 3: Synthesis of Compound BB-12-5

Compound BB-12-4 (supplier: TCI, 0.1 g, 0.66 mmol) and compound BB-12-3 (0.175 g, 0.66 mmol) were dissolved in anhydrous methanol (10 mL), the reactants were stirred at r.t. overnight, then the solvent was removed under reduced pressure to deliver compound BB-12-5 (yellow oil, 0.239 g, yield 100%) which was used for the next step directly without purification. MS (ESI) m/z: 363.0 [M+H]+.

Step 4: Synthesis of Compound BB-12-6

Compound BB-12-5 (0.239 g, 0.66 mmol) was dissolved in HOAc: $H_2O$=1:1 (3 mL), then $NaBH_3CN$ (0.041 g, 0.66 mmol) was added. The reaction mixture was stirred at r.t. for 3 hours, pH was adjusted to 6-7 with 1N aqueous NaOH solution, and then the mixture was extracted with EA (20 mL×3). The combined organic phase was washed with saturated brine (20 mL), dried over anhydrous sodium sulfate, and the solvent was removed under reduced pressure to deliver compound BB-12-6 (slight yellow oil, 0.240 g, yield 100%) which was used for the next step directly without purification. MS (ESI) m/z: 365.1 [M+H]+.

Step 5: Synthesis of Compound BB-12-7

Compound BB-12-6 (0.190 g, 0.52 mmol) was dissolved in THF:methanol:$H_2O$=2:2:1 (5 mL), lithium hydroxide monohydrate (0.109 g, 2.61 mmol) was added. The reaction mixture was stirred at r.t. for 2 hours, the solvent was removed under reduced pressure, the residue was dissolved in $H_2O$ again, pH was adjusted to about 2-3 with 2N aqueous hydrochloric acid solution, the mixture was extracted with DCM:methanol=10:1 (10 mL×3). The combined organic phase was washed with saturated brine (20 mL), dried over anhydrous sodium sulfate, the solvent was removed under reduced pressure to deliver compound BB-12-7 (yellow oil, 0.120 g, yield 65.7%) which was used for the next step directly without purification.

Step 6: Synthesis of Compound BB-12-8

Compound BB-12-7 (0.183 g, 0.52 mmol), HATU (0.238 g, 0.63 mmol) and DIPEA (0.338 g, 2.61 mmol) were dissolved in dry DMF (3 mL). The reaction mixture was stirred at r.t. overnight, purified by preparative chromatography (column: Agela DuraShell C18 150*25*5 m, eluting agent: MeCN+0.075% TFA, $H_2O$+0.075% TFA) to deliver the target compound BB-12-8 (slight yellow oil, 0.040 g, yield 23%). $^1$H NMR (400 MHz, $CD_3OD$): δ 7.42-7.35 (m, 5H), 5.19 (s, 2H), 4.28-3.72 (m, 8H).

Step 7: Synthesis of Compound BB-12

Compound BB-12-8 (0.040 g, 0.12 mmol) was dissolved in dry methanol (5 mL), Pd/C (0.010 g, 10%) was added, under hydrogen gas atmosphere (15 Psi), the reaction mixture was stirred at r.t. for 2 hours, filtered, the filtrate was evaporated under reduced pressure to deliver compound BB-12 (white solid, 0.030 g, yield 100%) which was used for the next step directly without purification.

Reference 13: Fragment BB-13

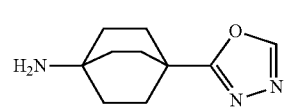

BB-13

Synthetic Route:

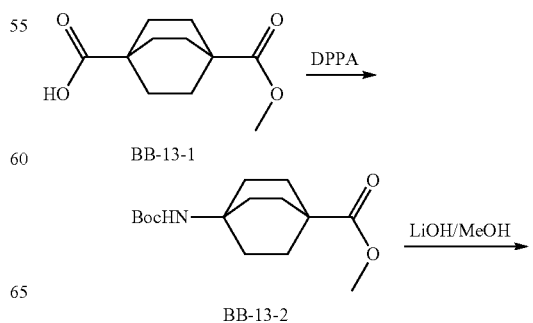

BB-13-1

BB-13-2

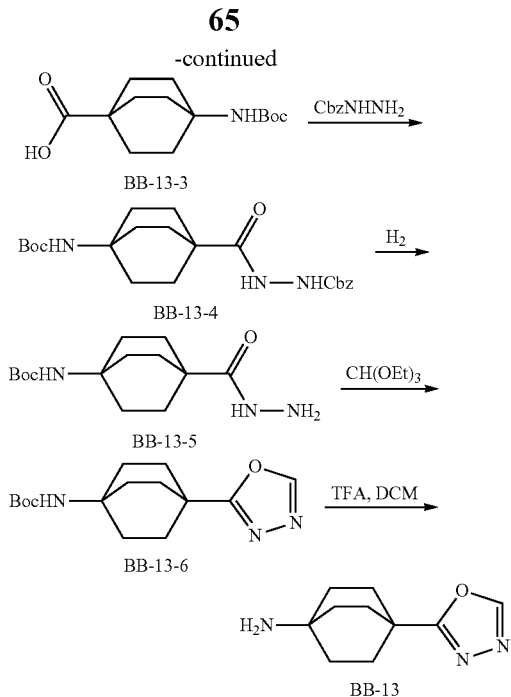

Step 1: Synthesis of Compound BB-13-2

Compound BB-13-1 (1.00 g, 4.71 mol) was dissolved in tert-BuOH (15 mL), then TEA (0.572 g, 5.65 mol), di-tert-butyl dicarbonate (3.70 g, 17.0 mmol) were added, then DPPA (1.56 g, 5.65 mmol) was added dropwise slowly. The reactants were stirred at 28° C. for 5 hours, then heated to reflux for 16 hours. After the reaction was complete, the solvent was evaporated, the residue was dissolved in MTBE (50 mL), washed with saturated NaHCO₃ solution (20 mL), the aqueous phase was extracted with MTBE (50 mL×2), the combined organic phase was washed with saturated brine (20 mL), dried, filtered, and concentrated to deliver the crude product, which was purified by flash column chromatography (eluting agent, EA/PE=1/6) to deliver the target compound BB-13-2 (white solid, 0.67 g, yield 50%). $^{1}$HNMR (400 MHz, CDCl$_{3}$): δ 3.65 (s, 3H), 1.89 (s, 12H), 1.41 (s, 9H).

Step 2: Synthesis of Compound BB-13-3

Compound BB-13-2 (0.056 g, 0.2 mmol) was dissolved in methanol (2.0 mL), then lithium hydroxide (2N, 2 mL) was added, pH of the reactants was adjusted to 4-5 with 1N hydrochloric acid, the mixture was extracted with EA (20 mL×3), washed with H$_2$O, dried over sodium sulfate, and evaporated to deliver the target compound BB-13-3 (white solid, 0.040 g, yield 80%). MS (ESI) m/z: 214 [M+H−56]$^{+}$.

Step 3: Synthesis of Compound BB-13-4

The reactant BB-13-3 (2.00 g, 7.43 mmol) was dissolved in DMF (20 mL), then benzyl carbazate (1.23 g, 7.43 mmol), DIPEA (2.88 g, 22.3 mmol), HATU (4.24 g, 11.1 mmol) were added. The reactants were stirred at 26° C. for 16 hours. H$_2$O (40 mL) was added, filtered, the cake was dissolved in DCM (50 mL), dried, filtered, and concentrated to deliver the target compound BB-13-4 (white solid, 2.5 g, yield 81%). $^{1}$HNMR (400 MHz, CDCl$_{3}$): δ 7.55 (m, 5H), 5.16 (s, 2H), 1.69 (s, 12H), 1.43 (s, 9H).

Step 4: Synthesis of Compound BB-13-5

Compound BB-13-4 (1.00 g, 2.40 mmol) was dissolved in methanol (20 mL), then wet Pd/C (0.2 g) was added. The reaction mixture was stirred at 26° C. for 16 hours under nitrogen gas atmosphere (15 Psi). The reaction mixture was filtered with celite, washed with methanol (50 mL), the filtrate was concentrated to deliver the target compound BB-13-5 (gray solid, 0.665 g, yield 98%). $^{1}$H NMR (400 MHz, CDCl$_{3}$): δ 4.37 (br, 1H), 1.90-1.80 (m, 12H), 1.42 (s, 9H).

Step 5: Synthesis of Compound BB-13-6

Compound BB-13-5 (0.665 g, 2.35 mmol) was dissolved in triethyl orthoformate (5 mL), p-TsOH (0.040 g, 0.235 mmol) was added, the reactants were stirred at 90° C. for 2 hours. The reaction mixture was concentrated to deliver the crude product which was purified by flash column chromatography (eluting agent, EA/PE=1/2) to deliver the target compound BB-13-6 (white solid, 0.560 g, yield 81%). $^{1}$H NMR (400 MHz, CDCl$_{3}$): δ 8.31 (s, 1H), 4.40 (br, 1H), 2.10-1.96 (m, 12H), 1.44 (s, 9H).

Step 6: Synthesis of Compound BB-13

Compound BB-13-6 (0.560 g, 1.91 mmol) was dissolved in DCM (20 mL), TFA (4 mL) was added. The reaction mixture was stirred at 26° C. for 2 hours. After the reaction was complete, the mixture was washed with H$_2$O (30 mL), pH of the aqueous phase was adjusted to 9 with Na$_2$CO$_3$, then the mixture was extracted with DCM (20 mL×5), the combined organic phase was dried over anhydrous sodium sulfate, filtered, and concentrated to deliver the target compound BB-13 (white solid, 0.200 g, yield 54%). $^{1}$H NMR (400 MHz, CDCl$_{3}$): δ 8.31 (s, 1H), 2.08-2.04 (br, 6H), 1.71-1.68 (m, 6H).

Reference 14: Fragment BB-14

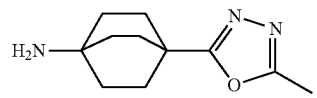

Synthetic Route:

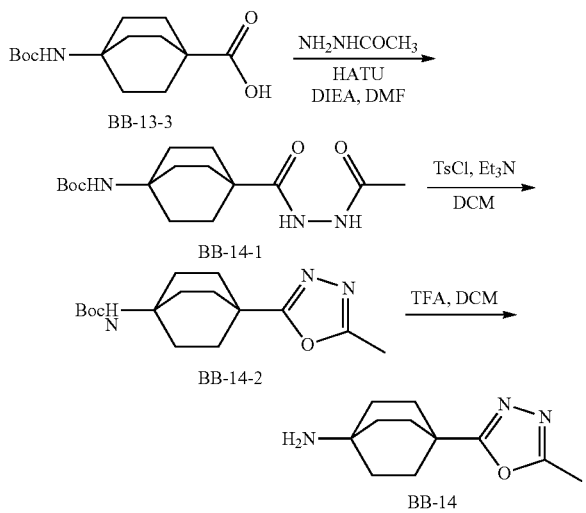

Step 1: Synthesis of Compound BB-14-1

Compound BB-13-3 (1.65 g, 6.13 mmol) was dissolved in DMF (20 mL), then acethydrazide (0.499 g, 6.74 mmol), DIPEA (2.37 g, 18.38 mmol), HATU (3.03 g, 7.96 mmol) were added, the reaction mixture was stirred at r.t. for 3 hours. After the reaction was complete, H$_2$O was added, then the mixture was extracted with EA (50 mL×3), the organic phase was washed with brine (20 mL), dried over anhydrous sodium sulfate, filtered, and concentrated to deliver the crude product which was purified by flash column chromatography (eluting agent, EA/PE=4/1) to deliver the target compound BB-14-1 (white solid, 1.6 g, yield 80%). MS (ESI) m/z: 326 [M+H]$^+$.

Step 2: Synthesis of Compound BB-14-2

Compound BB-14-1 (0.500 g, 1.54 mmol) was dissolved in DCM (8 mL), then TEA (0.311 g, 3.07 mmol), p-TsCl (0.469 g, 2.46 mmol) were added, the reaction mixture was stirred at r.t. for 4 hours. After the reaction was complete, DCM (100 mL) was added, the organic phase was washed with brine (20 mL), dried over anhydrous sodium sulfate, filtered, and concentrated to deliver the crude product, which was purified by flash column chromatography (eluting agent, EA/PE=1/1) to deliver the target compound BB-14-2 (white solid, 0.330 g, yield 70%). MS (ESI) m/z: 308 [M+H]$^+$.

Step 3: Synthesis of Compound BB-14

Compound BB-14-2 (0.320 g, 1.04 mmol) was dissolved in DCM (4 mL), then TFA (1 mL) was added, the reaction mixture was stirred at r.t. for 2 hours. After the reaction was complete, DCM (100 mL) was added, the organic phase was washed with saturated aqueous Na$_2$CO$_3$ solution, brine (20 mL), dried over anhydrous sodium sulfate, filtered, and concentrated to deliver the target compound BB-14 (white solid, 0.205 g, yield 95%). MS (ESI) m/z: 208 [M+H]$^+$.

Reference 15: Fragment BB-15

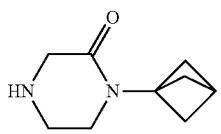

Synthetic Route:

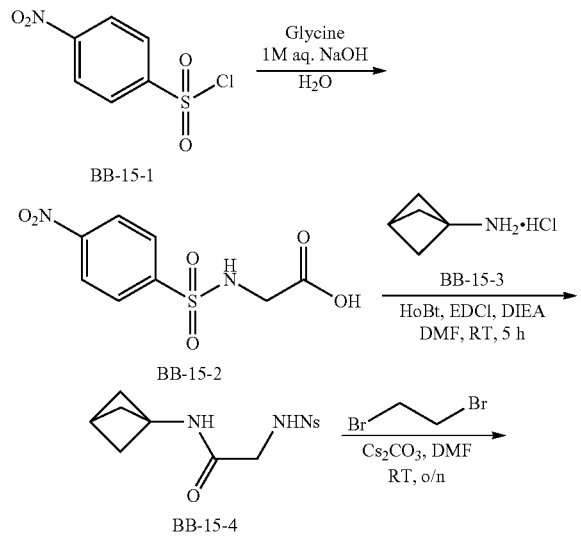

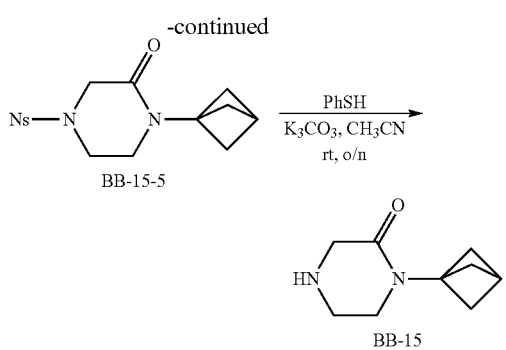

Step 1: Synthesis of Compound BB-15-2

Glycine (1.51 g, 20.1 mmol) was suspended in H$_2$O (5 mL), aqueous NaOH solution (1 M, 10 mL) was added dropwise, compound BB-15-1 (6.20 g, 28.0 mmol) was added, NaOH (1M, 20 mL) was added dropwise in portions, pH was kept greater than 9. After the addition, the reactants were stirred at r.t. for further 30 minutes. The reaction mixture was filtered, the filtrate was adjusted to be acidic with aqueous hydrochloric acid solution (5 M), and the precipitated solid was filtered out to deliver the target compound BB-15-2 (yellow solid, 2.4 g, yield 33%). $^1$H NMR (400 MHz, CDCl$_3$): δ 8.31 (d, J=8.8 Hz, 2H), 8.03 (d, J=8.8 Hz, 2H), 3.78 (s, 2H).

Step 2: Synthesis of Compound BB-15-4

Compound BB-15-3 (supplier: Aroma Circle Corp., 0.050 g, 0.417 mmol) was added into 1.5 mL DMF, then compound BB-15-2 (0.108 g, 0.417 mmol), HOBt (0.062 g, 0.459 mmol), DIPEA (0.161 g, 1.25 mmol), EDC HCl (0.088 g, 0.459 mmol) were added. After stirring at r.t. for 5 hours, the organic phase was poured into H$_2$O, extracted with EA (25 mL), the organic phase was washed with saturated brine (20 mL), dried over anhydrous sodium sulfate, the solvent was removed under reduced pressure, the resulting residue was purified by flash column chromatography (eluting agent, EA/PE=1/3) to deliver the target compound BB-15-4 (yellow solid, 0.075 g, yield 55.6%). MS (ESI) m/z: 326 [M+H]$^+$.

Step 3: Synthesis of Compound BB-15-5

Compound BB-15-4 (0.100 g, 0.308 mmol) was added into 3 mL DMF, then dibromoethane (0.348 g, 1.85 mmol), CsCO$_3$ (0.401 g, 1.23 mmol) were added. After stirring at r.t. for 16 hours, the reaction was quenched with H$_2$O, dried over anhydrous sodium sulfate, the mixture was evaporated under reduced pressure to deliver the target compound BB-15-5 (yellow solid, 0.080 g, yield 80%). MS (ESI) m/z: 352 [M+H]$^+$.

Step 4: Synthesis of Compound BB-15

Compound BB-15-5 (0.080 g, 0.228 mmol) was added into 2 mL MeCN, then PhSH (0.075 g, 0.684 mmol) was added. After stirring at r.t. for 16 hours under nitrogen gas atmosphere, the organic phase was poured into DCM, filtered, the mixture was evaporated under reduced pressure to deliver the target compound BB-15 (yellow oil, 0.025 g, yield 65.8%). MS (ESI) m/z: 167 [M+H]$^+$.

Reference 16: Fragment BB-16

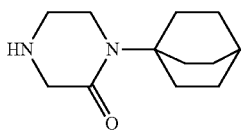

Synthetic Route:

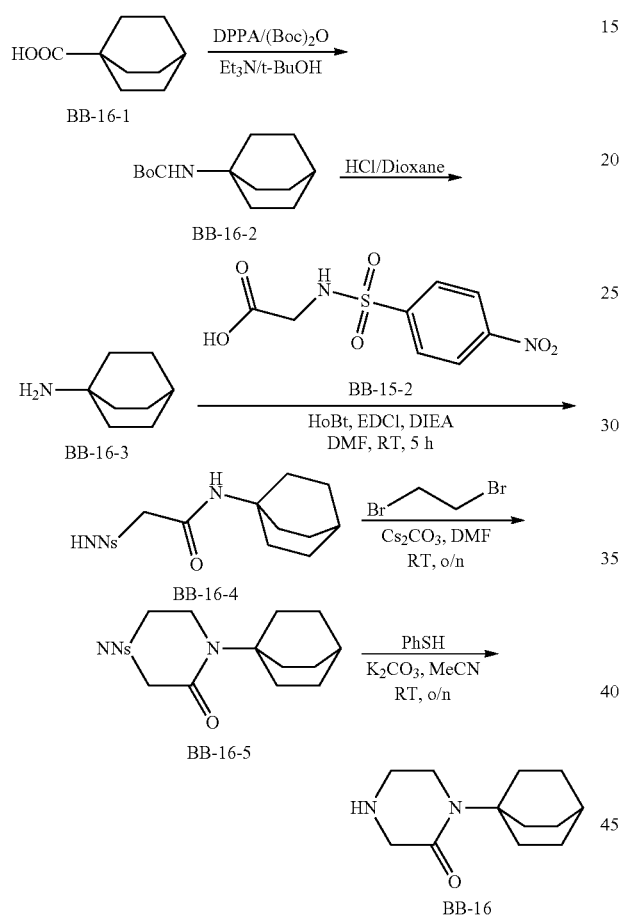

Step 1: Synthesis of Compound BB-16-2

Compound BB-16-1 (supplier: Shanghai SHUYA, 0.50 g, 3.24 mmol), di-tert-butyl dicarbonate (2.5 g, 11.67 mmol) and TEA (0.393 g, 3.89 mmol) were dissolved in tert-butanol (20 mL), DPPA (1.07 g, 3.89 mmol) was added slowly under nitrogen gas atmosphere, then reaction mixture was stirred at r.t. for about 8 hours, followed by heating to reflux for 16 hours, the solvent was removed under reduced pressure, the residue was extracted with MTBE (150 mL×3), dried over anhydrous sodium sulfate, the mixture was evaporated under reduced pressure, the resulting residue was purified by flash preparative chromatography (eluting agent: PE/EA=30:1) to deliver the target compound BB-16-2 (white solid, 0.30 g, yield 41%), which was used for the next step directly. $^1$H NMR (400 MHz, CDCl$_3$): δ 4.27-4.13 (br, 1H), 1.77-1.63 (m, 6H), 1.62-1.51 (m, 6H), 1.50-1.45 (m, 1H), 1.35 (s, 9H).

Step 2: Synthesis of Compound BB-16-3

Compound BB-16-2 (0.300 g, 1.33 mmol) was added into 5 mL DCM, then hydrochloric acid/dioxane (5 mL) was added. After stirring at r.t. for 16 hours, the mixture was evaporated under reduced pressure to deliver the target compound BB-16-3 (white solid, 0.200 g, yield 100%). MS (ESI) m/z: 126 [M+H]$^+$.

Step 3: Synthesis of Compound BB-16-4

Compound BB-16-3 (0.200 g, 1.242 mmol) was added into 5 mL DMF, then compound BB-15-2 (0.324 g, 1.242 mmol), HOBt (0.184 g, 1.366 mmol), EDC HCl (0.262 g, 1.366 mmol), DIPEA (0.480 g, 3.72 mmol) were added. After stirring at r.t. for 5 hours, the organic phase was poured into H$_2$O, the mixture was extracted with EA (50 mL×2), the organic phase was washed with saturated brine (20 mL), dried over anhydrous sodium sulfate, the solvent was removed under reduced pressure, the resulting residue was purified by flash column chromatography (eluting agent, EA/PE=1/3) to deliver the target compound BB-16-4 (yellow oil, 0.200 g, yield 43.8%). MS (ESI) m/z: 368 [M+H]$^+$.

Step 4: Synthesis of Compound BB-16-5

Compound BB-16-4 (0.150 g, 0.408 mmol) was added into 5 mL DMF, then compound 1,2-dibromoethane (0.462 g, 2.451 mmol), CsCO$_3$ (0.531 g, 1.632 mmol) were added. After stirring at 60° C. for 16 hours, the reaction was quenched with H$_2$O, the mixture was dried over anhydrous sodium sulfate, evaporated under reduced pressure to deliver the target compound BB-16-5 (yellow solid, 0.100 g, yield 80%). MS (ESI) m/z: 394 [M+H]$^+$.

Step 5: Synthesis of Compound BB-16

Compound BB-16-5 (0.100 g, 0.487 mmol) was added into 5 mL MeCN, then PhSH (0.429 g, 3.9 mmol), K$_2$CO$_3$ (0.269 g, 1.95 mmol) were added. After stirring at r.t. for 16 hours under nitrogen gas atmosphere, the organic phase was poured into DCM, filtered, the mixture was evaporated under reduced pressure to deliver the target compound BB-16 (yellow oil, 0.025 g, yield 24.6%). MS (ESI) m/z: 209 [M+H]$^+$.

Reference 17: Fragment BB-17

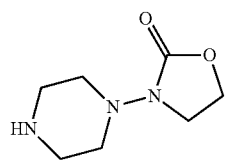

Synthetic Route:

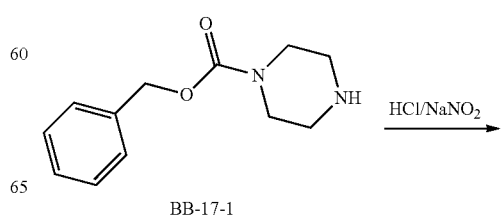

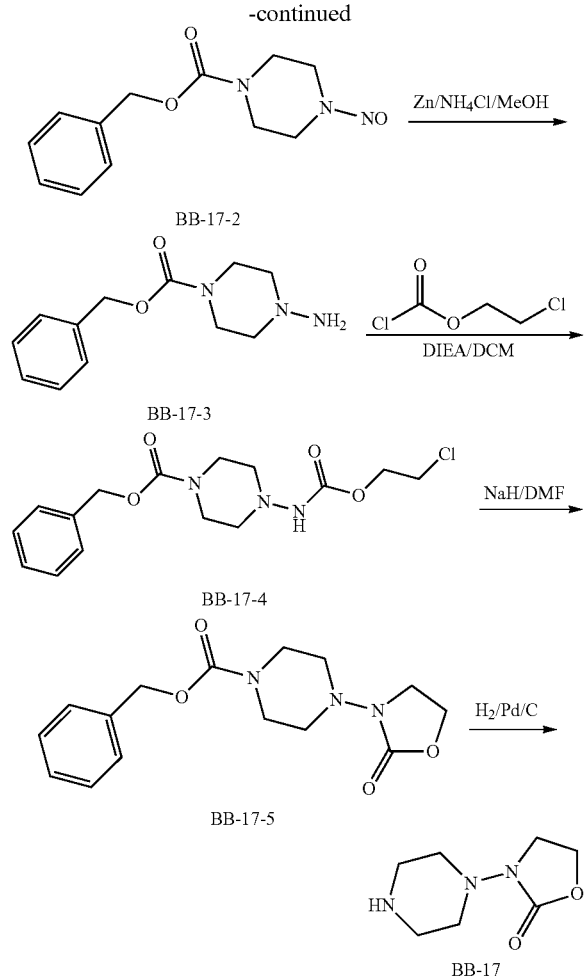

Step 1: Synthesis of Compound BB-17-2

Compound BB-17-1 (7.0 g, 31.78 mmol) was dissolved in dilute hydrochloric acid (6M, 150 mL) and the mixture was stirred to be uniform, NaNO$_2$ solution (4N, 30 mL) was added dropwise slowly under nitrogen gas atmosphere, then the mixture was stirred at r.t. for about 1 hour, 100 mL H$_2$O was added, the mixture was extracted with EA (100 mL×3). The combined organic phase was washed with saturated brine (20 mL), dried over anhydrous sodium sulfate, the solvent was removed under reduced pressure to deliver the target compound BB-17-2 (7.5 g, yield 66%), which was used for the next step directly without purification. MS (ESI) m/z: 250 [M+H]$^+$.

Step 2: Synthesis of Compound BB-17-3

Compound BB-17-2 (4.0 g, 16 mmol), zinc powder (6.2 g, 96 mmol) and NH$_4$Cl (10 g, 192 mmol) were dissolved in methanol (80 mL), the mixture was stirred at r.t. for 10 minutes, then heated to 45° C. and stirred for 2 hours, filtered under reduced pressure, the cake was washed with methanol, the filtrate was concentrated to dry under reduced pressure, DCM was added into the residue and the mixture was stirred for 1 hour, the filtrate was concentrated to dry under reduced pressure to deliver the target compound BB-17-3 (3.5 g crude product), which was used for the next step directly without purification. MS (ESI) m/z: 236 [M+H]$^+$.

Step 3: Synthesis of Compound BB-17-4

Compound BB-17-3 (3.5 g crude product) and DIPEA (3.81 g, 29.6 mmol) were dissolved in DCM (100 mL), under an ice-bath, 2-chloroethyl chloroformate (2.55 g, 18 mmol) was added dropwise slowly under nitrogen gas atmosphere, then the reaction mixture was stirred at r.t. for about 2 hours, followed by diluting with H$_2$O (80 mL), the mixture was extracted with DCM (100 mL) (60 mL×3). The combined organic phase was washed with saturated brine (20 mL), dried over anhydrous sodium sulfate, and evaporated under reduced pressure to deliver the compound BB-17-4 (5.0 g crude product), which was used for the next step directly without purification. MS (ESI) m/z: 342 [M+H]$^+$.

Step 4: Synthesis of Compound BB-17-5

Compound BB-17-4 (5.0 g crude product) was dissolved in DMF (100 mL), under an ice-water bath, NaH (60%, 2.0 g) was added under nitrogen gas atmosphere, then the mixture was stirred at r.t. for about 2 hours, the reaction was quenched by adding H$_2$O (100 mL), the mixture was extracted with EA (300 mL), the organic phase was washed with saturated brine (30 mL×5), dried over anhydrous sodium sulfate, and evaporated under reduced pressure, the residue was purified by flash preparative chromatography (eluting agent: PE/EA=1:10) to deliver the target compound BB-17-5 (2.4 g). MS (ESI) m/z: 306 [M+H]$^+$.

Step 4: Synthesis of Compound BB-17

Compound BB-17-5 (2.4 g 7.86 mmol) was dissolved in methanol (80 mL), then Pd/C (0.400 g) was added, the reaction mixture was stirred at r.t. overnight under hydrogen gas atmosphere (15 Psi), and then Pd/C was filtered off, the filtrate was concentrated to dry under reduced pressure to deliver the target compound BB-17 (1.2 g, yield 89%), which was used for the next step directly. $^1$H NMR (400 MHz, CDCl$_3$): δ 4.30 (t, J=7.8 Hz, 2H), 3.62 (t, J=7.8 Hz, 2H), 3.03-2.87 (m, 8H).

Reference 18: Fragment BB-18

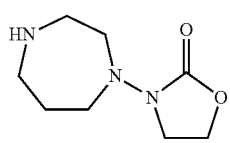

Synthetic Route:

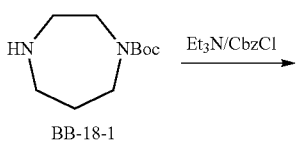

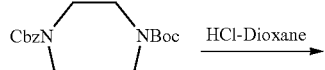

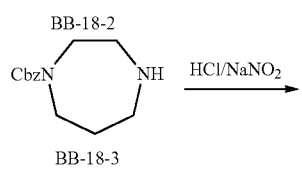

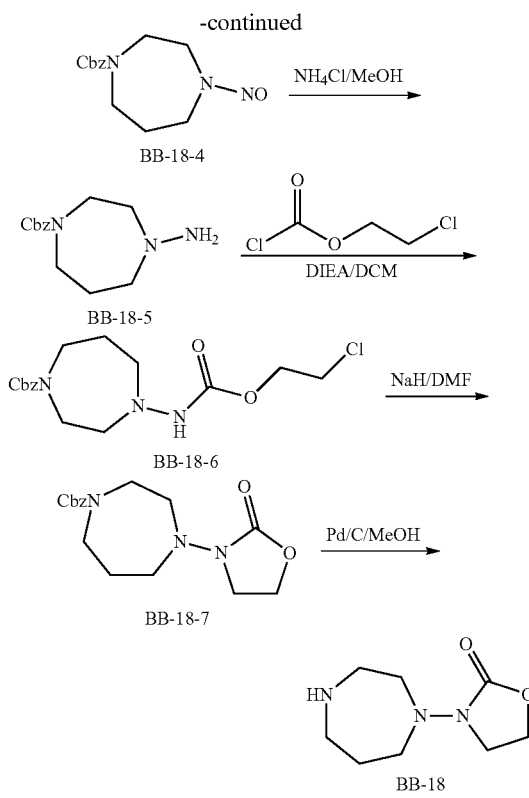

Step 1: Synthesis of Compound BB-18-2

Compound BB-18-1 (2.0 g, 10 mmol) and TEA (2.02 g, 20 mmol) was dissolved in DCM (40 mL), under an ice-water bath, benzyl chloroformate (2.0 g, 11 mmol) was added slowly under nitrogen gas atmosphere, then the mixture was stirred at r.t. for 24 hours, dilute hydrochloric acid (1N, 30 mL) was added, the mixture was extracted with EA (80 mL×3). The combined organic phase was washed with saturated brine (20 mL), dried over anhydrous sodium sulfate, the solvent was removed under reduced pressure to deliver the target compound BB-18-2 (2.6 g crude product), which was used for the next step directly without purification. MS (ESI) m/z: 279 [M+H−56]$^+$.

Step 2: Synthesis of Compound BB-18-3

Compound BB-18-2 (2.6 g crude product) was dissolved in HCl/dioxane (4M, 25 mL) and the mixture was stirred to be uniform, then the reaction mixture was stirred at r.t. for 2 hours, then concentrated to deliver the target compound BB-18-3 (1.8 g crude product), which was used directly for the next step without purification. MS (ESI) m/z: 235 [M+H]$^+$.

Step 3: Synthesis of Compound BB-18-4

Compound BB-18-3 (1.8 g crude product) was dissolved in dilute hydrochloric acid (6M, 40 mL) and the mixture was stirred to be uniform, NaNO$_2$ solution (2N, 17 mL) was added dropwise slowly under nitrogen gas atmosphere, then the reaction mixture was stirred at r.t. for 1 hour, 50 mL H$_2$O was added, the mixture was extracted with EA (60 mL×3). The organic phases were combined and washed with saturated brine (20 mL), dried over anhydrous sodium sulfate, and concentrated to remove the solvent thereby delivering the target compound BB-18-4 (2 g crude product), which was used for the next step directly without purification. MS (ESI) m/z: 264 [M+H]$^+$.

Step 4: Synthesis of Compound BB-18-5

Compound BB-18-4 (2 g crude product), zinc powder (2.73 g, 42 mmol) and NH$_4$Cl (4.45 g, 84 mmol) were dissolved in methanol (50 mL), the mixture was stirred at r.t. for 10 minutes, then heated to 45° C. and stirred for 2 hours, the mixture was filtered under reduced pressure, the cake was washed with methanol, the filtrate was concentrated to dry under reduced pressure, DCM (100 mL) was added into the residue, and the mixture was stirred for 1 hour, the insolubles were filtered off, the filtrate was concentrated to dry under reduced pressure to deliver the target compound BB-18-5 (1.8 g crude product), which was used for the next step without purification. MS (ESI) m/z: 250 [M+H]$^+$.

Step 5: Synthesis of Compound BB-18-6

Compound BB-18-5 (1.8 g crude product) and DIPEA (1.85 g, 14.4 mmol) were dissolved in DCM (40 mL), under an ice-water bath, compound 2-chloroethyl chloroformate (1.36 g, 9.6 mmol) was added dropwise slowly under nitrogen gas atmosphere, then the mixture was stirred at r.t. for 2 hours, diluted by H$_2$O (50 mL), extracted with DCM (50 mL×3). The organic phases were combined and washed with saturated brine (20 mL), dried over anhydrous sodium sulfate, and concentrated to remove the solvent thereby delivering the target compound BB-18-6 (2.5 g crude product), which was used for the next step directly without purification. MS (ESI) m/z: 356 [M+H]$^+$.

Step 6: Synthesis of Compound BB-18-7

Compound BB-18-6 (0.710 g crude product) was dissolved in DMF (15 mL), under an ice-water bath, NaH (60%, 0.320 g) was added under nitrogen gas atmosphere, then the mixture was stirred at r.t. for about 2 hours, then quenched by adding H$_2$O (50 mL), the mixture was extracted with EA (200 mL), the organic phase was washed with saturated brine (20 mL×5), dried over anhydrous sodium sulfate, evaporated under reduced pressure, the resulting residue was purified by flash preparative chromatography (eluting agent: PE/EA=1:10) to deliver the target compound BB-18-7 (0.300 g, yield 47%). MS (ESI) m/z: 320 [M+H]$^+$.

Step 7: Synthesis of Compound BB-18

Compound BB-18-7 (0.300 g, 0.94 mmol) was dissolved in methanol (5 mL), then Pd/C (0.020 g) was added, the mixture was stirred at r.t. overnight under hydrogen gas atmosphere (15 Psi), Pd/C was filtered off, the filtrate was concentrated to dry under reduced pressure to deliver the target compound BB-18 (0.170 g, yield 97.7%), which was used for the next step directly.

Reference 19: Fragment BB-19

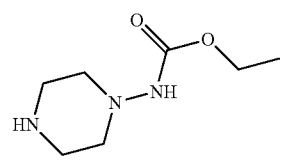

Synthetic Route:

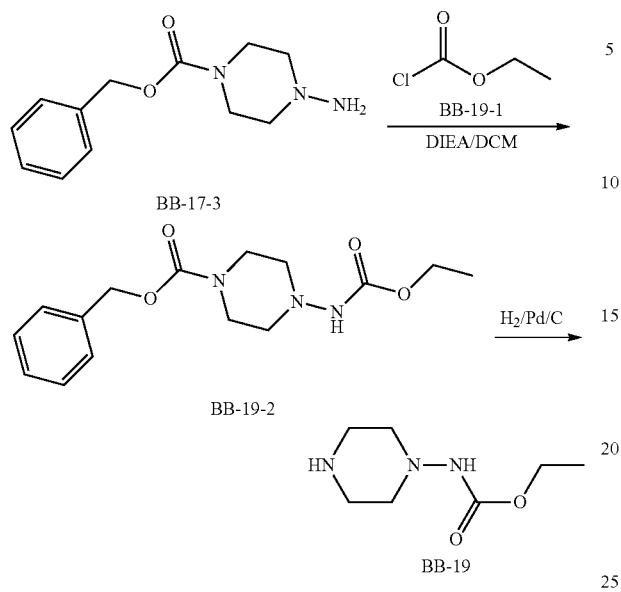

Step 1: Synthesis of Compound BB-19-2

Compound BB-17-3 (1.0 g, 4.2 mmol) and TEA (0.860 g, 8.5 mmol) were dissolved in DCM (20 mL), compound BB-19-1 (0.680 g, 6.3 mmol) was added dropwise slowly at −10° C. under nitrogen gas atmosphere, then the mixture was stirred at r.t. for 2 hours, diluted by adding H$_2$O (50 mL), extracted with DCM (50 mL×3). The organic phases were combined and washed with saturated brine (20 mL), dried over anhydrous sodium sulfate, and concentrated to remove the solvent thereby delivering the compound BB-19-2 (1.3 g crude product), which was used for the next step directly without purification. MS (ESI) m/z: 308 [M+H]$^+$.

Step 2: Synthesis of Compound BB-19

Compound BB-19-2 (0.100 g, 0.32 mmol) was dissolved in methanol (10 mL), then Pd/C (0.020 g) was added, the mixture was stirred at r.t. overnight under the protection of hydrogen gas balloon (15 Psi), Pd/C was filtered off, the filtrate was concentrated to dry under reduced pressure to deliver the target compound BB-19 (0.056 g, yield 99.4%) which was used for the next step directly. MS (ESI) m/z: 174 [M+H]$^+$.

Reference 20: Fragment BB-20

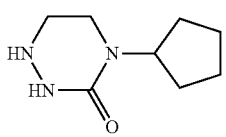

Synthetic Route:

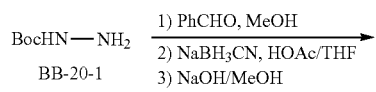

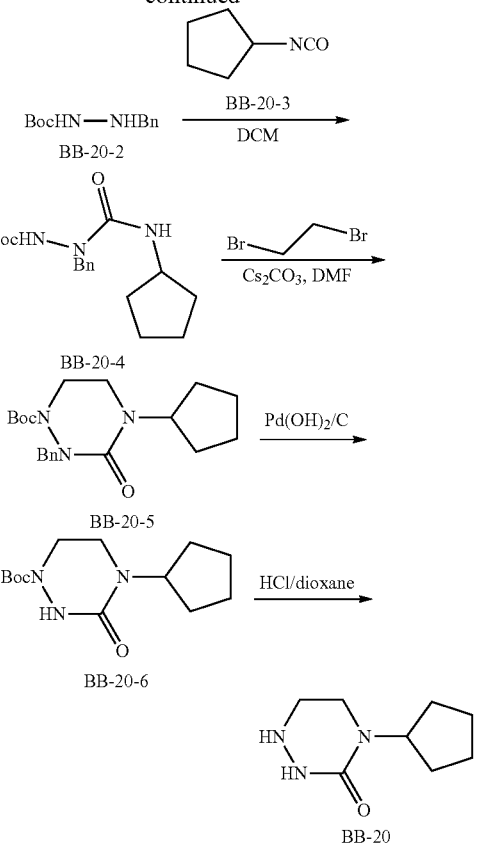

Step 1: Synthesis of Compound BB-20-2

Compound BB-20-1 (1 g, 7.6 mmol) was dissolved in THF (10 mL), benzaldehyde (0.77 mL, 7.6 mmol) was added. The reaction mixture was stirred at r.t. for 4 hours, then concentrated. The resulting solid (1.3 g, 7.6 mmol) was then dissolved in THF (15 mL) again, AcOH (9 mL) and NaBH$_3$CN (1.05 g, 16.7 mmol) were added, the reaction mixture was stirred at r.t. overnight. pH was adjusted to 9-10 with 1M aqueous NaOH solution, the mixture was extracted with EA (50 mL×3). The organic phase was washed with brine, dried over anhydrous sodium sulfate, filtered, and concentrated to deliver 1.5 g solid. Then the resulting solid (1.5 g, 7.6 mmol) was dissolved in methanol (10 mL) again, 1M aqueous NaOH solution (10 mL) was added. The reaction was stirred at r.t. for 2 hours, concentrated, and extracted with DCM (50 mL×3). The organic phase was washed with brine, dried over anhydrous sodium sulfate, filtered, and concentrated to deliver the crude product BB-20-2 (white solid, 1.37 g, 81.45%) which was used for the next step directly. $^1$H NMR (400 MHz, CDCl$_3$): δ 7.28-7.33 (m, 4H), 4.02 (s, 2H), 1.45 (s, 9H). MS (ESI) m/z: 167.0 [M+H−56]$^+$.

Step 2: Synthesis of Compound BB-20-4

Compound BB-20-3 (0.833 g, 7.5 mmol) was dissolved in DCM (20 mL), compound BB-20-2 (1.1 g, 5 mmol) was added. The reaction mixture was stirred at r.t. for 2 hours, then quenched by adding H$_2$O, extracted with DCM (100 mL×3). The organic phases were combined, washed with brine, dried over anhydrous sodium sulfate, filtered, and concentrated, the crude product was purified by preparative HPLC (column: Phenomenex Gemini C18 250*50 mm*5 μm, eluting agent: MeCN+0.05% NH$_3$.H$_2$O, H$_2$O+0.05%

NH₃.H₂O) to deliver BB-20-4 (yellow solid, 0.730 g, yield 49%). ¹H NMR (400 MHz, DMSO-d₆): δ 7.24-7.29 (m, 5H), 6.10 (br, s, 5H), 3.92 (s, 2H), 1.73-1.77 (m, 8H), 1.45 (s, 9H). MS (ESI) m/z: 304.0 [M+H]⁺.

Step 3: Synthesis of Compound BB-20-5

Compound BB-20-4 (0.600 g, 1.80 mmol) and 1,2-dibromoethane (0.507 g, 2.70 mmol) were dissolved in DMF (10 mL), CsCO₃ (1.76 g, 5.40 mmol) was added. The reaction mixture was stirred at r.t. for 10 minutes under nitrogen gas atmosphere, then heated to 40° C., stirred for 48 hours. The reaction mixture was cooled to r.t., and poured into 50 mL H₂O. The aqueous phase was extracted with EA (100 mL×3). The organic phases were combined, washed with brine, dried over anhydrous sodium sulfate, filtered, and concentrated. The crude product was purified by flash silica gel column (eluting agent: EA/PE=1/1) to deliver BB-20-5 (yellow oil, 0.140 g, yield 22%). MS (ESI) m/z: 382.2 [M+Na]⁺.

Step 4: Synthesis of Compound BB-20-6

Compound BB-20-5 (0.200 g, 0.556 mmol) was dissolved in methanol (20 mL), Pd(OH)₂/C (20%, 0.020 g) was added under argon gas atmosphere. The reaction mixture was swept by hydrogen gas for 3 times, followed by adjusting the pressure of hydrogen gas (50 psi) at 50° C., the reaction mixture was stirred for 48 hours, then filtered, and concentrated to deliver the crude product BB-20-6 (gray solid, 0.180 g, crude product), which was used for the next step directly. MS (ESI) m/z: 270 [M+H]⁺.

Step 5: Synthesis of Compound BB-20

Compound BB-20-6 (0.180 g, crude product) was dissolved in HCl/dioxane (3 mL, 4M), the reaction mixture was stirred at r.t. for 1 hour, then concentrated to deliver the crude product of compound BB-20 hydrochloride (yellow solid, 0.140 g, 100%), which was used for the next step directly. MS (ESI) m/z: 170 [M+H]⁺.

Reference 21: Fragment BB-21

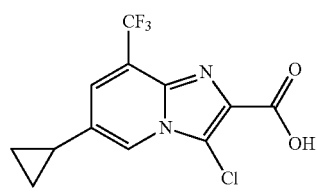

BB-21

Synthetic Route:

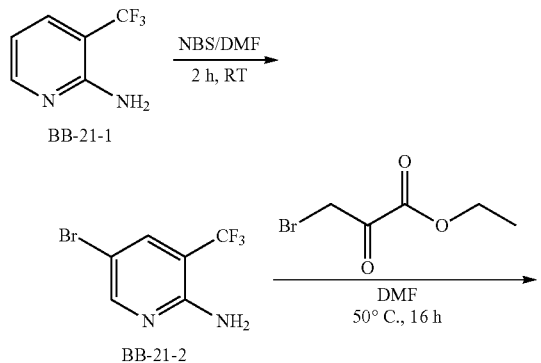

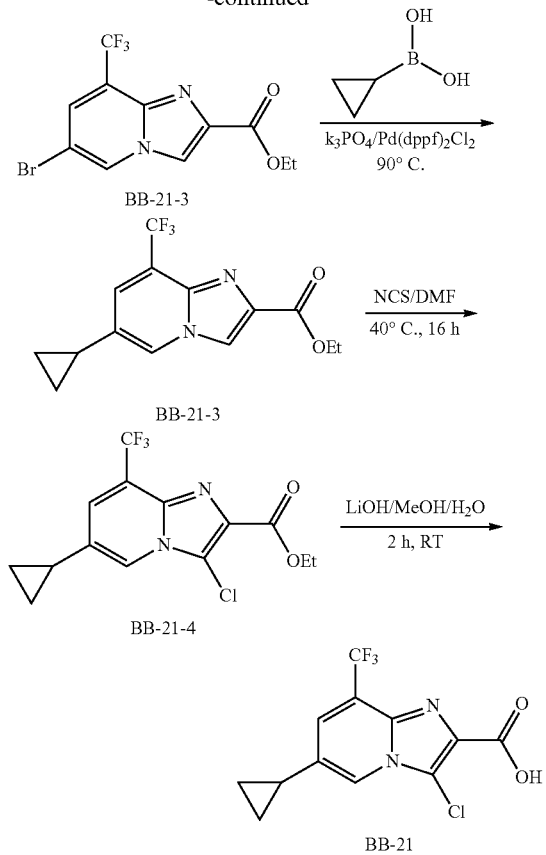

Step 1: Synthesis of Compound BB-21-2

Compound BB-21-1 (42.0 g, 259 mmol) was dissolved in DMF (400 mL), then NBS (46.1 g, 259 mmol) was added. The reactants were stirred at 20° C. for 2 hours. The reaction mixture was poured into a mixture of 5% NaHSO₃ and H₂O (10:1) while stirring, the precipitate was filtered out, washed with H₂O, dissolved in DCM (500 mL), dried over sodium sulfate, filtered, and concentrated to deliver the target compound BB-20-2 (yellow solid, 51.0 g, yield 89.7%). ¹HNMR (400 MHz, CDCl₃): δ 8.27 (s, 1H), 7.80 (s, 1H), 5.02 (br, 2H). MS (ESI) m/z: 241 [M+H]⁺, 243 [M+H+2]⁺.

Step 2: Synthesis of Compound BB-21-3

Compound BB-21-2 (51.0 g, 212 mmol) was dissolved in DMF (500 mL), then ethyl bromopyruvate (82.5 g, 423 mmol) was added. The reactants were stirred at 50° C. for 16 hours. The reaction mixture was cooled to r.t., poured into a mixture of ice and water (1 L) and stirred for 20 minutes, the precipitate was filtered out, the cake was dissolved in EA (500 mL), dried over sodium sulfate, filtered, and concentrated to deliver the target compound BB-21-3 (yellow solid, 71.0 g, yield 99.5%). ¹H NMR (400 MHz, CDCl₃): δ 8.49 (s, 1H), 8.25 (s, 1H), 7.69 (s, 1H), 4.47 (q, J=6.8 Hz, 2H), 1.43 (t, J=6.8 Hz, 3H). MS (ESI) m/z: 337 [M+H]⁺, 339 [M+H+2]⁺.

Step 3: Synthesis of Compound BB-21-4

Compound BB-21-3 (55.0 g, 163 mmol) and cyclopropylboronic acid (15.4 g, 179 mmol) were dissolved in dioxane (500 mL), then K₃PO₄ (103.9 g, 489 mmol) and 1,1'-bis(diphenylphosphino)ferrocene-palladium(II) dichloride dichloromethane complex (2.70 g, 3.26 mmol) were added under nitrogen gas atmosphere. The reactants were stirred at 90° C. for 16 hours. The reaction mixture was cooled to r.t., filtered with celite, the filtrate was concentrated to deliver the crude product, which was purified by flash column chromatography (eluting agent: EA/PE=1/4) to deliver the target compound BB-21-4 (yellow solid, 24.0 g, yield 49.3%). $^1$H NMR (400 MHz, CDCl$_3$): δ 8.18 (s, 1H), 8.06 (s, 1H), 7.38 (s, 1H), 4.46 (q, J=7.2 Hz, 2H), 1.98 (m, 1H), 1.43 (t, J=7.2 Hz, 3H), 1.07 (m, 2H), 0.76 (m, 2H). MS (ESI) m/z: 299 [M+H]$^+$.

Step 4: Synthesis of Compound BB-21-5

Compound BB-21-4 (28.0 g, 93.9 mmol) was dissolved in DMF (250 mL), NCS (12.5 g, 93.9 mmol) was added. The reactants were stirred at 40° C. for 16 hours. The reaction mixture was cooled to r.t., and poured into H$_2$O (500 mL), stirred for 20 minutes, the precipitate was filtered out, dried to deliver the target compound BB-21-5 (white solid, 31.0 g, yield 99.3%). MS (ESI) m/z: 333 [M+H]+.

Step 5: Synthesis of Compound BB-21-6

Compound BB-21-5 (31.0 g, 93.2 mmol) was dissolved in methanol (400 mL), compound lithium hydroxide monohydrate (19.6 g, 466 mmol) and H$_2$O (100 mL) were added. The reactants were stirred at 20° C. for 2 hours. The reaction mixture was concentrated, pH of the residue was adjusted below 3 with conc. hydrochloric acid, the mixture was extracted with EA (400 mL×3). The combined organic phase was washed with saturated brine (200 mL), dried over sodium sulfate, filtered, and concentrated to deliver the target compound BB-21-6 (white solid, 27.3 g, yield 89.6%). $^1$HNMR (400 MHz, CDCl$_3$): δ 8.05 (s, 1H), 7.42 (s, 1H), 2.02 (m, 1H), 1.08 (m, 2H), 0.76 (m, 2H). MS (ESI) m/z: 305 [M+H]$^+$.

Reference 22: Fragment BB-22

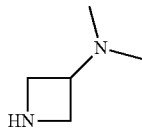

BB-22

Synthetic Route:

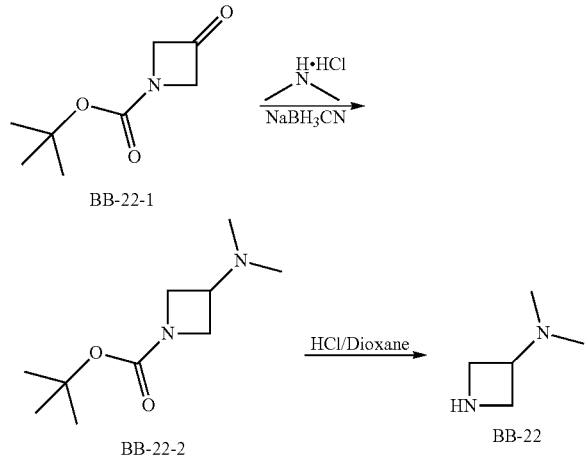

Step 1: Synthesis of Compound BB-22-2

Compound BB-22-1 (0.1 g, 0.584 mmol) was dissolved in DCM (1 mL), dimethylamine hydrochloride (0.072 g, 0.876 mmol) was added. The reaction mixture was stirred at r.t. for 2 hours, NaBH$_3$CN (0.055 g, 0.876 mmol) was added, then the mixture was stirred at r.t. overnight. After the reaction was complete, the reaction mixture was poured into 20 mL H$_2$O, extracted with DCM/methanol (10/1) (30 mL×3). The organic phases were combined, washed with saturated brine (20 mL×2), dried over anhydrous sodium sulfate, filtered, and concentrated to deliver the crude product of the target compound BB-22-2 (yellow oil, 0.12 g). $^1$H NMR (400 MHz, CDCl$_3$): δ 4.10-4.21 (m, 2H), 3.87-3.95 (m, 2H), 3.81 (d, J=4.41 Hz, 1H), 2.16 (s, 6H), 1.43-1.44 (m, 9H).

Step 2: Synthesis of Compound BB-22

Compound BB-22-2 (0.11 g, 0.549 mmol) was dissolved in DCM (2 mL), HCl/dioxane solution (1 mL, 4M) was added, the reaction mixture was stirred at r.t. for 3 hours. After the reaction was complete, the mixture was concentrated to deliver the target compound BB-22 hydrochloride (yellow solid, 0.075 g, crude product), which was used for the next step directly without purification.

Reference 23: Fragment BB-23

Synthetic Route:

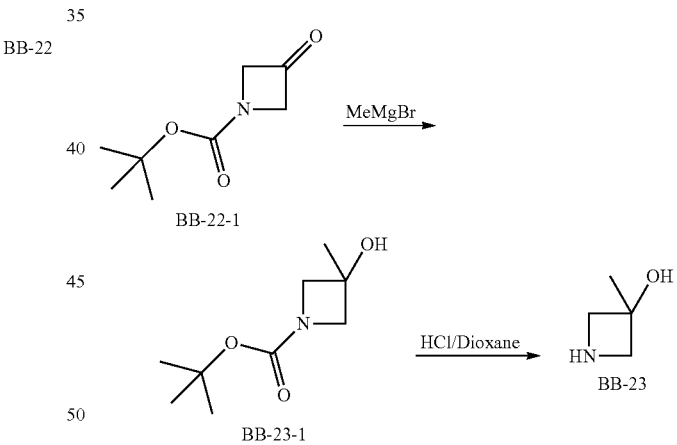

Step 1: Synthesis of Compound BB-23-1

Compound BB-22-1 (0.4 g, 2.34 mmol) was dissolved in anhydrous THF (5 mL), the reaction mixture was cooled to 0° C., and methyl magnesium bromide in THF solution (3M, 1.00 mL) was added dropwise under nitrogen gas atmosphere. Then the reaction mixture was warmed to r.t., stirred for 1 hour, 1M aqueous NH$_4$Cl solution (10 mL) was added. The reaction mixture was extracted with EA (30 mL×3), the organic phases were combined and washed with saturated brine (20 mL×2), dried over anhydrous sodium sulfate, filtered, and concentrated to deliver the crude product of the target compound BB-23-1 (yellow solid, 0.47 g). $^1$H NMR (400 MHz, CDCl$_3$): δ 4.07-4.17 (m, 1H), 3.79-3.88 (m, 4H), 1.51 (s, 3H), 1.43 (s, 9H).

Step 2: Synthesis of Compound BB-23

Compound BB-23-1 (0.15 g, 0.80 mmol) was dissolved in DCM (2 mL), HCl/dioxane solution (1 mL, 4M) was added, and the reaction mixture was stirred at r.t. for 3 hours. After the reaction was complete, the mixture was concentrated to deliver the target compound BB-23 hydrochloride (yellow solid, 0.099 g, crude product), which was used for the next step directly without purification.

Reference 24: Fragment BB-24

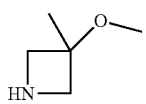

Synthetic Route:

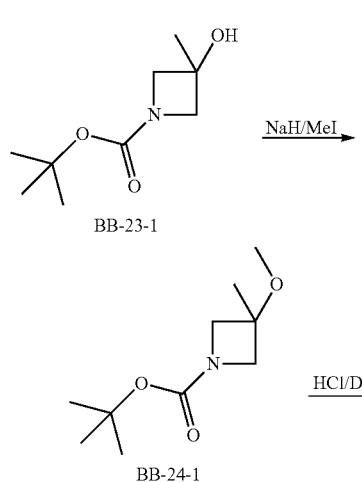

Step 1: Synthesis of Compound BB-24-1

Compound BB-23-1 (0.2 g, 1.07 mmol) was dissolved in anhydrous THF (5 mL), NaH (0.17 g, 4.30 mmol, 60%) was added at r.t. The reaction mixture was stirred for 10 mins, MeI (1.14 g, 8.03 mmol) was added, and the reaction mixture was stirred at r.t. overnight. After the reaction was complete, it was quenched by adding 20 mL H$_2$O, the mixture was extracted with EA (50 mL×3), the organic phases were combined and washed with saturated brine (20 mL×2), dried over anhydrous sodium sulfate, filtered, and concentrated to deliver the crude product of the target compound BB-23-1 (yellow oil, 0.26 g). $^1$H NMR (400 MHz, CDCl$_3$): δ 3.90 (d, J=9.04 Hz, 2H), 3.66 (d, J=9.04 Hz, 2H), 3.19-3.29 (m, 3H), 1.45 (s, 3H), 1.44 (s, 9H).

Step 2: Synthesis of Compound BB-24

Compound BB-23-1 (0.14 g, 0.70 mmol) was dissolved in DCM (2 mL), HCl/dioxane solution (1 mL, 4M) was added, the reaction mixture was stirred at r.t. for 3 hours. After the reaction was complete, the mixture was concentrated to deliver the target compound BB-24 hydrochloride (white solid, 0.095 g), the crude was used for the next step directly without purification.

Reference 25: Fragment BB-25

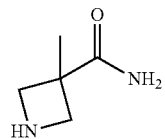

Synthetic Route:

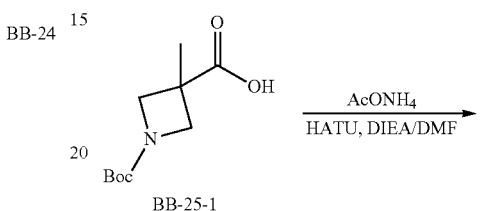

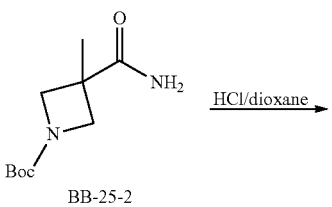

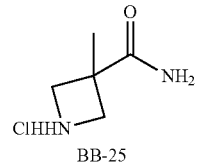

Step 1: Synthesis of Compound BB-25-2

Compound BB-25-1 (0.1 g, 0.46 mmol) and NH$_4$OAc (0.035 g, 0.046 mmol) were dissolved in DMF (2 mL), then HATU (0.265 g, 0.697 mmol) and DIPEA (0.18 g, 1.39 mmol) were added, the reactants were stirred at r.t. for 16 hours. After the reaction was complete, EA was added, the organic phase was washed with aqueous NaHCO$_3$ solution and saturated brine, dried over anhydrous sodium sulfate, filtered, and the filtrate was concentrated to remove the solvent thereby delivering the target compound BB-25-2 (white solid, 0.05 g, crude product), the crude was used for the next step directly without purification. MS (ESI) m/z: 237 [M+Na]$^+$.

Step 2: Synthesis of Compound BB-25-3

Compound BB-25-2 (0.05 g, crude product) was dissolved in THF (1.5 mL), then HCl/dioxane solution (1.5 mL, 4M) was added, the reactants were stirred at r.t. for 1.5 hours, then the mixture was concentrated under reduced pressure to remove the solvent thereby delivering the target compound BB-25 (white solid, 0.025 g, crude product).

Reference 26: Fragment BB-26

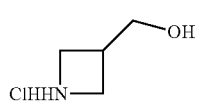

Synthetic Route:

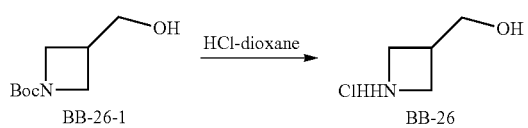

Step 1: Synthesis of Compound BB-26

Compound BB-26-1 (0.100 g, 0.534 mmol) was dissolved in DCM (2 mL), then HCl/dioxane solution (1 mL, 4M) was added. The reaction mixture was stirred at 20° C. for 2 hours. The reaction mixture was concentrated to deliver the target compound BB-26 (white solid, 0.060 g, yield 90.91%).

Reference 27: Fragment BB-27

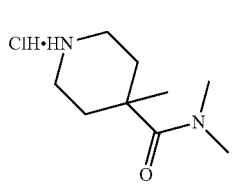

Synthetic Route:

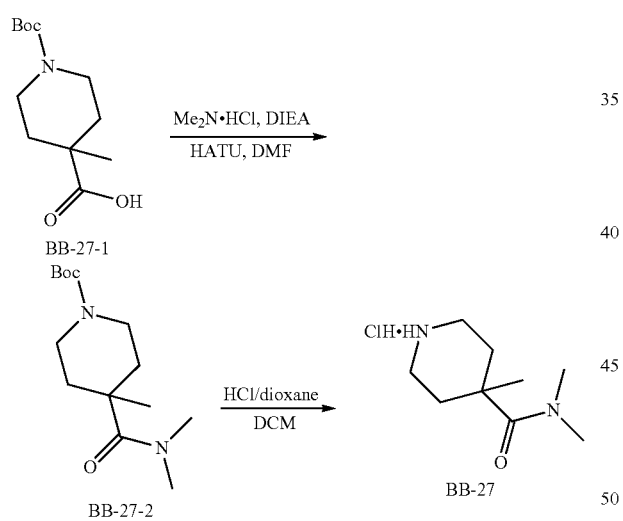

Step 1: Synthesis of Compound BB-27-2

Compound BB-27-1 (0.10 g, 0.411 mmol) was dissolved in DMF (3 mL), then dimethyl amine hydrochloride (0.070 g, 0.858 mmol), DIPEA (0.210 g, 1.62 mmol), HATU (0.184 g, 0.484 mmol) were added, the reactants were stirred at r.t. for 2 hours. After the reaction was complete, EA was added, the organic phase was washed with saturated brine (20 mL), dried over anhydrous sodium sulfate, filtered, and the filtrate was concentrated under reduced pressure to remove the solvent thereby delivering the target compound BB-27-2 (light yellow oil, 0.111 g, yield 99.89%). MS (ESI) m/z: 293 [M+Na]⁺.

Step 2: Synthesis of Compound BB-27-3

Compound BB-27-2 (0.111 g, 0.411 mmol) was dissolved in DCM (3 mL), then HCl/dioxane solution (3 mL, 4M, 12.00 mmol) was added, the reactants were stirred at r.t. for 2 hours. After the reaction was complete, the mixture was concentrated to deliver the target compound BB-27 directly, which was used for the next step (yellow solid, 0.085 g, crude product).

Reference 28: Fragment BB-28

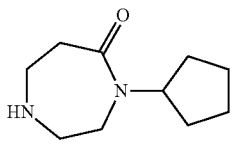

Synthetic Route:

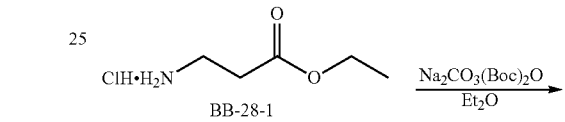

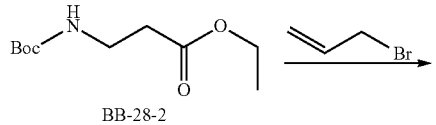

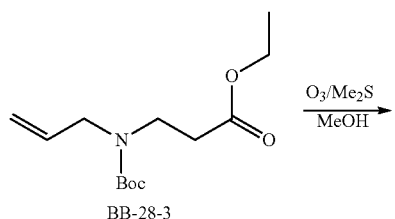

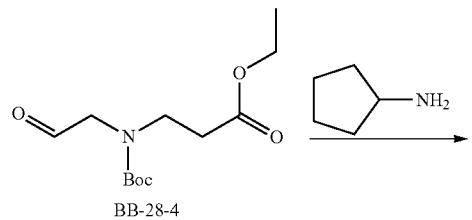

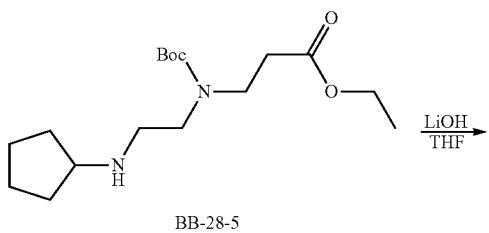

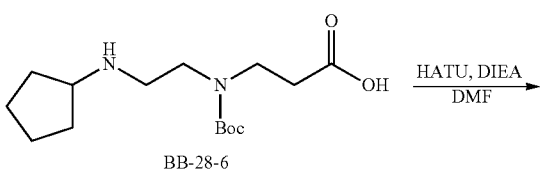

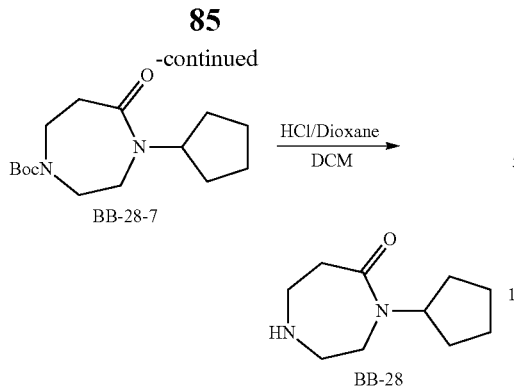

Step 1: Synthesis of Compound BB-28-2

Compound BB-28-1 (10 g, 85.36 mmol), di-tert-butyl dicarbonate (18.6 g, 85.36 mmol) were dissolved in $Et_2O$ (100 mL), then $Na_2CO_3$ (18.1 g, 170.73 mmol) was formulated to a saturated solution and added into the reaction mixture, the reactants were stirred at 25° C. overnight. After the reaction was complete, the solid was removed by filtration, the filtrate was concentrated to deliver the target compound BB-28-2 (yellow solid, 14 g, crude product). MS (ESI) m/z: 240[M+Na]$^+$.

Step 2: Synthesis of Compound BB-28-3

Compound BB-28-1 (6 g, 27.6 mmol) and allyl bromide (4 g, 33.1 mmol) were dissolved in DMF (60 mL), then NaH (1.7 g, 41.4 mmol, 60%) was added in portions at 0° C., the reaction mixture was stirred at 0° C. for 3 hours. After the reaction was complete, the reaction was quenched by adding $H_2O$, the mixture was extracted with EA, the organic phase was washed with brine, dried over anhydrous sodium sulfate, filtered, and concentrated to deliver the crude product which was purified by flash column chromatography (eluting agent: EA/PE=1/10) to deliver the target compound BB-28-3 (yellow oil, 2 g, crude product). MS (ESI) m/z: 158[M-Boc+H]$^+$.

Step 3: Synthesis of Compound BB-28-4

Compound BB-28-3 (2 g, 7.8 mmol) was dissolved in methanol (20 mL), the mixture was cooled to -78° C., $O_3$ was introduced until the reaction mixture became blue, then $N_2$ was introduced until the reaction mixture became colorless, $Me_2S$ (12.4 g, 38.8 mmol) was then added, reacted at 25° C. overnight. After the reaction was complete, the mixture was concentrated, EA was added, the organic phase was washed with brine, dried over anhydrous sodium sulfate, filtered, and concentrated to deliver the target compound BB-28-4 (yellow oil, 1.8 g, crude product). MS (ESI) m/z: 160[M-Boc+H]$^+$.

Step 4: Synthesis of Compound BB-28-5

Compound BB-28-4 (0.5 g, 1.93 mmol), cyclopentyl amine (0.197 g, 2.31 mmol), DIPEA (0.29 g, 1.93 mmol) and anhydrous $Na_2SO_4$ (0.197 g, 2.31 mmol) were dissolved in dry methanol (5 mL), the reactants were stirred at r.t. for 2 hours, $NaBH_4$ (0.088 g, 2.31 mmol) was added slowly, then the mixture was stirred at r.t. for 2 hours. The reaction was quenched with aqueous $NH_4Cl$ solution, the mixture was extracted with EA, washed with $H_2O$, dried over anhydrous sodium sulfate, and concentrated to deliver the crude product which was purified by flash column chromatography (eluting agent: methanol/DCM=1/10) to deliver the target compound BB-28-5 (yellow oil, 0.25 g, crude product). MS (ESI) m/z: 329[M+H]$^+$.

Step 5: Synthesis of Compound BB-28-6

Compound BB-28-5 (0.1 g, 0.3 mmol) was dissolved in THF (0.5 mL), then aqueous LiOH solution (1 mL, 2M) was added. The reaction mixture was stirred at 30° C. for 4 hours, then concentrated under reduced pressure to remove THF, followed by frozen drying to deliver compound BB-28-6 (yellow oil, 0.09 g, crude product), which was used for the next step directly without purification. MS (ESI) m/z: 301 [M+H]$^+$.

Step 6: Synthesis of Compound BB-28-7

Compound BB-12-7 (0.09 g, 0.3 mmol), HATU (0.172 g, 0.45 mmol) and DIPEA (0.116 g, 0.9 mmol) were dissolved in dry DMF (2 mL). The reaction mixture was stirred at 20° C. for 4 hours, after the reaction was complete, the reaction mixture was poured into EA. The mixture was washed with brine, dried over sodium sulfate, and concentrated to deliver the crude product, which was isolated and purified by thin silica gel plate (developing agent: EA/PE=1/3) to deliver the compound BB-28-6 (yellow oil, 0.05 g, 55%). MS (ESI) m/z: 227 [M−56+H]$^+$.

Step 7: Synthesis of Compound BB-28

Compound BB-28-7 (0.05 g, 0.18 mmol) was dissolved in DCM (1 mL), HCl/dioxane solution (1 mL, 4M) was added, the reaction mixture was stirred at 20° C. for 1.5 hours, then concentrated under reduced pressure to deliver compound BB-28 (white solid, 0.030 g, crude product), which was used for the next step directly without purification. MS (ESI) m/z: 183[M+H]$^+$.

Reference 29: Fragment BB-29

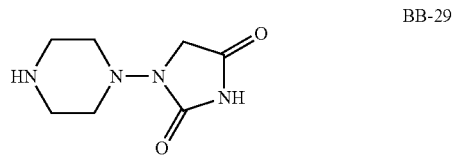 [SMILES: O=C1CN(N2CCNCC2)C(=O)N1]

Synthetic Route:

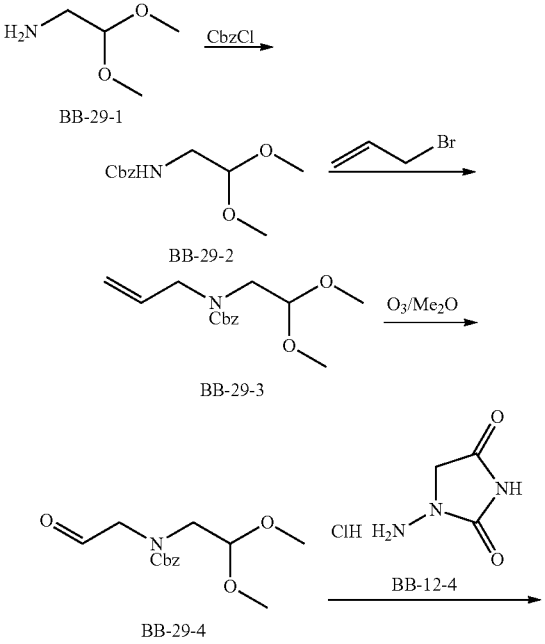

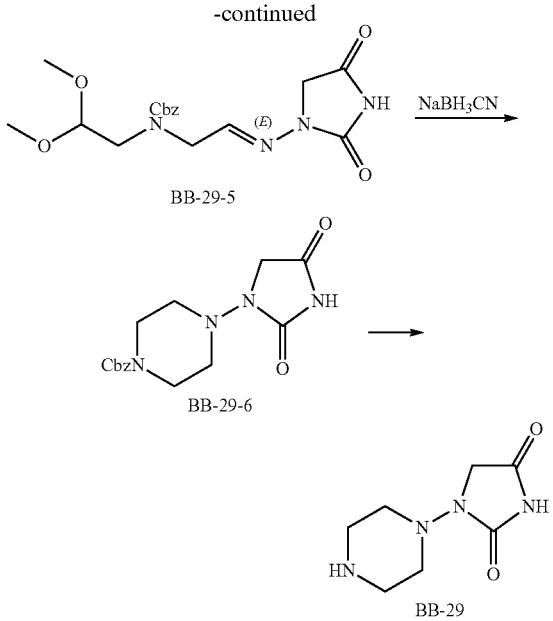

Step 1: Synthesis of Compound BB-29-2

Compound BB-29-1 (4.56 g, 43.37 mmol) was dissolved in toluene (24 mL), NaOH (2.19 g, 54.65 mmol) was dissolved in H$_2$O (12 mL), then aqueous NaOH solution was added into the mixture slowly. Benzyl chloroformate (6.96 g, 40.77 mmol) was added dropwise slowly into the reaction mixture, the temperature of the reaction solution was kept at 10-20° C. After the addition, the reactants were stirred at r.t. for 16 hours. After the reaction was complete, the organic phase was separated, washed with brine (50 mL×2), dried over sodium sulfate, filtered, and concentrated to deliver the target compound BB-29-2 (yellow oil, 11 g, crude product), which was used for the next step directly. $^1$H NMR (400 MHz, CDCl$_3$): δ 7.38-7.27 (m, 5H), 5.1 (s, 2H), 4.38 (t, J=5.4 Hz, 1H), 3.38 (s, 6H), 3.35-3.32 (m, 2H).

Step 2: Synthesis of Compound BB-29-3

Compound BB-29-2 (5.62 g, 23.49 mmol), KOH (2.64 g, 46.98 mmol) and BTMA (0.088 g, 0.474 mmol) were suspended in toluene (20 mL), then a solution of 3-allyl bromide (5.68 g, 46.98 mmol) in toluene (6 mL) was slowly added, the temperature of the reactants was kept at 20-30° C. The reactants were stirred at r.t. for 16 hours, then at 30° C. for 24 hours. After the reaction was complete, 20 mL H$_2$O was added, the organic phase was separated, dried over anhydrous sodium sulfate, filtered, and concentrated under reduced pressure to deliver the target compound BB-29-3 (yellow oil, 5.20 g, crude product). $^1$H NMR (400 MHz, CDCl$_3$): δ 7.35-7.29 (m, 5H), 5.79-5.73 (m, 1H), 5.17-5.14 (m, 3H), 4.53-4.07 (m, 1H), 4.00-3.96 (m, 2H), 3.40-3.31 (m, 8H).

Step 3: Synthesis of Compound BB-29-4

The reactant BB-29-3 (2.00 g, 7.16 mmol) was dissolved in methanol/DCM (3:1, 40 mL), the mixture was cooled to −78° C., O$_2$ was introduced for 5 minutes, then O$_3$ was introduced until the solution became continuous blue, then O$_2$ was introduced until the solution became colorless. Me$_2$S (0.344 g, 7.16 mmol) was added into the reaction mixture, and the mixture was slowly warmed to r.t., then stirred at r.t. for 16 hours. The reaction mixture was concentrated under reduced pressure to deliver the compound BB-29-4 (yellow oil, 2.70 g, crude product), which was used for the next step directly. $^1$H NMR (400 MHz, CDCl$_3$): δ 7.37-7.28 (m, 5H), 5.18-5.12 (m, 2H), 4.45-4.34 (m, 1H), 3.47-3.45 (m, 2H), 3.42-3.40 (m, 2H), 3.39-3.30 (m, 3H), 3.09 (s, 1H).

Step 4: Synthesis of Compound BB-29-5

Compound BB-29-4 (0.500 g, 1.32 mmol) was dissolved in methanol (5 mL), then compound BB-12-4 (TCI, 0.199 g, 1.32 mmol) was added, the reaction mixture was stirred at r.t. for 16 hours. The reaction mixture was concentrated under reduced pressure to deliver the compound BB-29-5 (orange oil, 0.550 g, crude product), which was used for the next step directly.

Step 5: Synthesis of Compound BB-29-6

Compound BB-29-5 (0.450 g, 1.19 mmol) was suspended in formic acid (5 mL), NaBH$_3$CN (0.150 g, 2.38 mmol) was added slowly, the reactants were stirred at r.t. for 20 hours under nitrogen gas atmosphere. The reaction mixture was concentrated under reduced pressure, the residue was isolated and purified by HPLC (column: Phenomenex Gemini C18 150*25 mm*5 μm, eluting agent: MeCN, H$_2$O) to deliver the target compound BB-29-6 (yellow oil, 0.040 g, yield 10%). MS (ESI) m/z: 301 [M+H]$^+$.

Step 6: Synthesis of Compound BB-29

Compound BB-29-6 (0.050 g, 0.157 mmol) was dissolved in methanol (5 mL), then Pd/C (0.010 g) was added, the reactants were stirred at r.t. for 1 hour under hydrogen gas atmosphere (15 Psi). The reaction mixture was filtered, the filtrate was concentrated under reduced pressure to deliver the target compound BB-29 (yellow oil, 0.030 g, crude product). MS (ESI) m/z: 185 [M+H]$^+$.

Reference 30: Fragment BB-30 and BB-30a

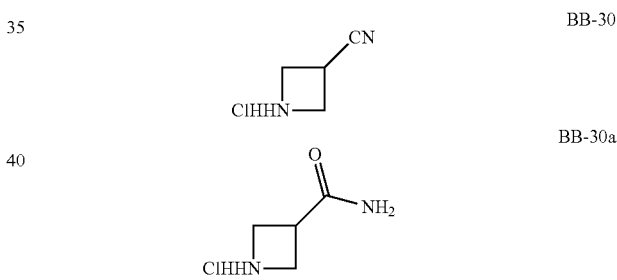

Synthetic Route:

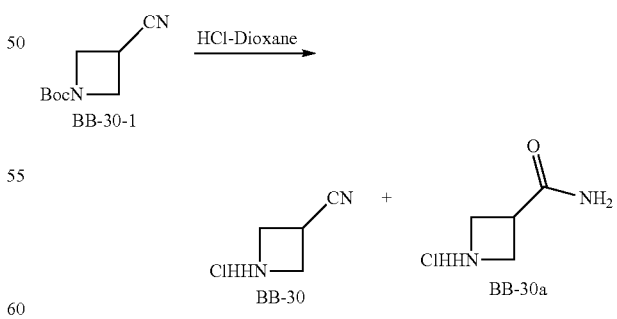

Step 1: Synthesis of Compound BB-30 and BB-30a

Compound BB-30-1 (0.200 g, 1.10 mmol) was dissolved in DCM (2 mL), then HCl/dioxane solution (1 mL, 4M) was added. The reaction mixture was stirred at 20° C. for 2 hours. The reaction mixture was concentrated to deliver the target compound BB-30 and BB-30a (white solid, 0.130 g, yield 99%), which were not isolated and used for the next step directly. MS (ESI) m/z: 83 [M+H]⁺. MS (ESI) m/z: 101 [M+H]⁺.

Reference 31: Fragment BB-31

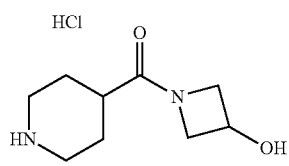

Synthetic Route:

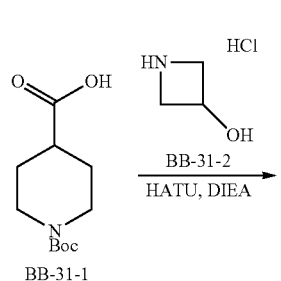

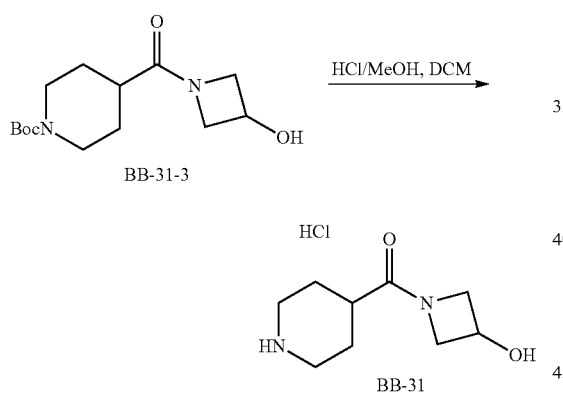

Reference 32: Fragment BB-32

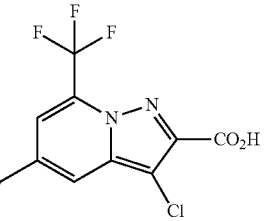

Synthetic Route:

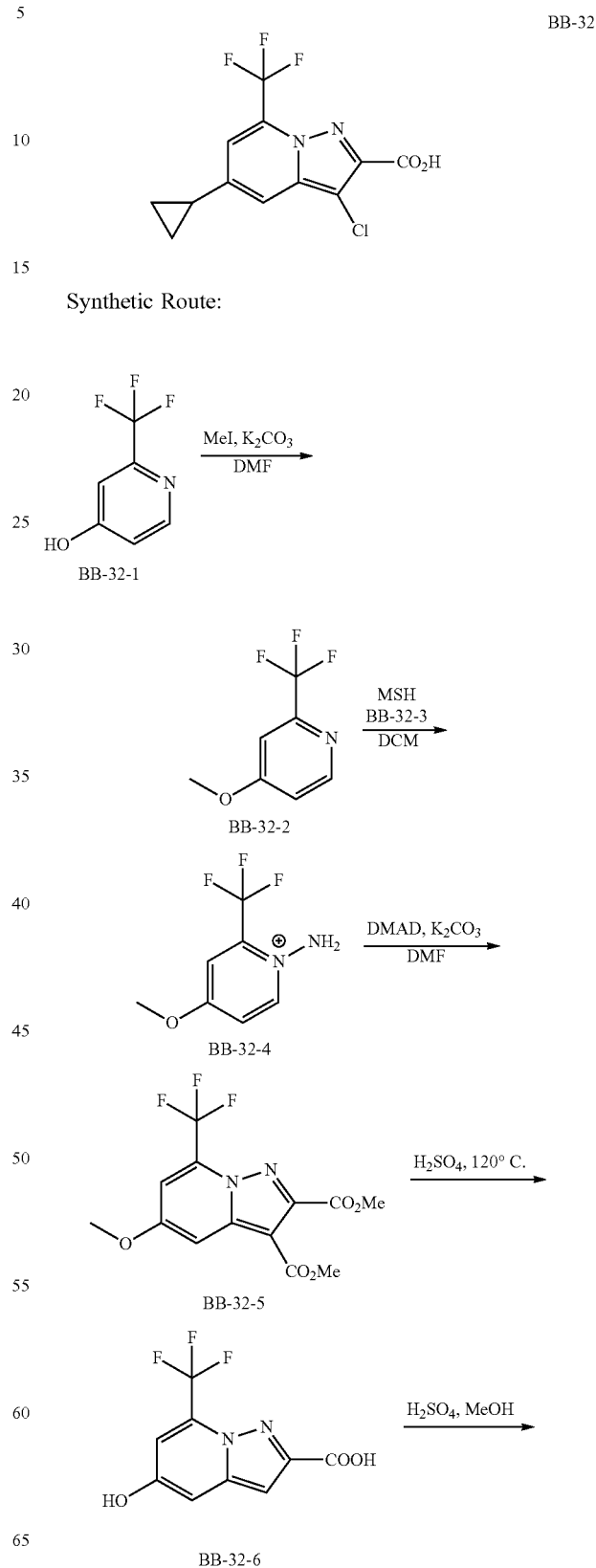

Step 1: Synthesis of Compound BB-31-3

Compound BB-31-1 (0.5 g, 2.18 mmol) and BB-31-2 (0.239 g, 2.18 mmol) were dissolved in DMF (5 mL), then DIPEA (0.845 g, 6.54 mmol) and HATU (1.24 g, 3.27 mmol) were added. The reactants were stirred at 20° C. for 3 hours. H₂O (10 mL) was added, the mixture was extracted with EA (20 mL×3). The combined organic phase was washed with H₂O (20 mL×2), brine (20 mL), dried over sodium sulfate. The mixture was filtered and concentrated to deliver the target compound BB-31-3 (yellow oil, 0.6 g, yield 97%). MS (ESI) m/z: 307 [M+Na]⁺.

Step 2: Synthesis of Compound BB-31

Compound BB-31-3 (0.1 g, 0.352 mmol) was dissolved in DCM (2 mL), then HCl/MeOH solution (1 mL, 4M) was added. The reaction mixture was stirred at 20° C. for 1 hour. The reaction mixture was concentrated to deliver the target compound BB-31 (white oil, 0.077 g, yield 99%). MS (ESI) m/z: 185 [M+H]⁺.

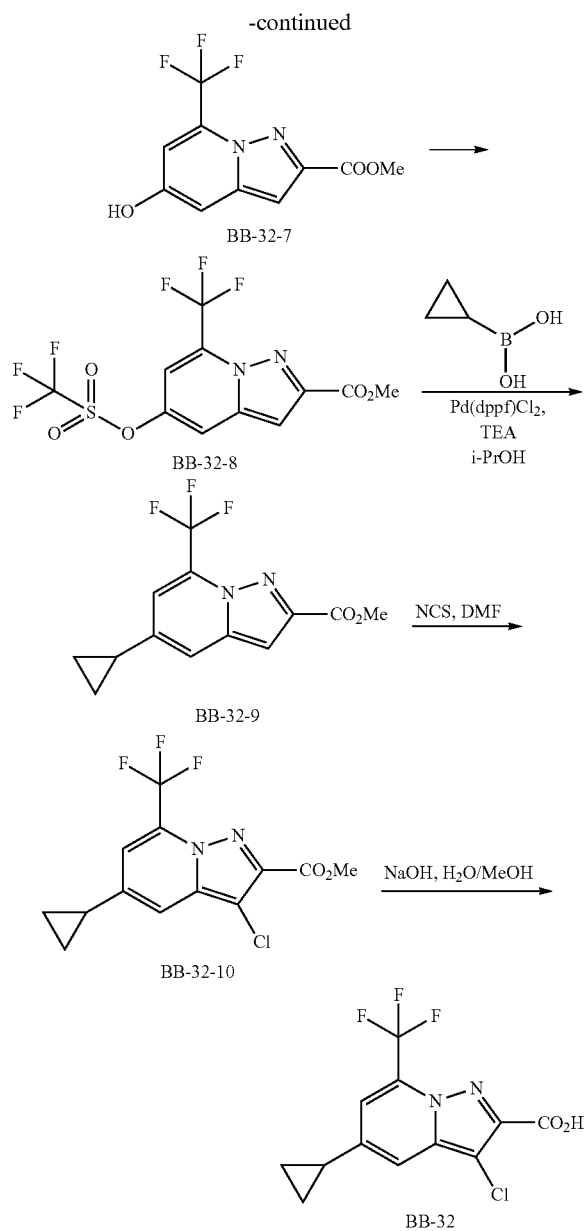

Step 1: Synthesis of Compound BB-32-2

Compound BB-32-1 (22 g, 134.9 mmol) and anhydrous K$_2$CO$_3$ (23 g, 161.9 mmol) were dissolved in anhydrous DMF (250 mL), then MeI (19 mL, 296.8 mmol) was added slowly. The reaction mixture was heated to 65° C. for 2 hours. Then the reaction mixture was diluted with H$_2$O, extracted with PE/DCM 9:1 (3×200 mL). The organic phases were combined, washed with H$_2$O (50 mL), saturated brine (50 mL), dried over anhydrous sodium sulfate, and concentrated to deliver the target compound BB-32-2 (yellow oil, 20 g, crude product), which was used for the next step directly. $^1$H NMR (400 MHz, CDCl$_3$): δ 8.50 (d, 1H), 7.30 (s, 1H), 6.90 (d, 1H). MS (ESI) m/z: 178.1 [M+H]$^+$.

Step 2: Synthesis of Compound BB-32-4

Ethyl O-methylsulphonylacetohydroxamate (50 g, 175.4 mmol) was dissolved in dioxane (48 mL, 561.3 mmol), the reaction mixture was cooled to 0° C. under nitrogen gas atmosphere. Then HClO$_4$ (22 mL, 368.3 mmol) was added dropwise over 30 minutes, the reaction mixture was stirred at r.t. for 2 hours, 100 mL mixture of ice and water was added. The reaction mixture was extracted with DCM (3×200 mL), the organic phases were combined, washed with saturated brine (50 mL), dried over anhydrous K$_2$CO$_3$ solid, and concentrated at 30° C. to deliver 200 mL solution of compound BB-32-3 in DCM. MS (ESI) m/z: 216.1[M+H]$^+$. The compound BB-32-2 (20 g, 112.9 mmol) and the solution of compound BB-32-3 in DCM were mixed. The reaction mixture was stirred at r.t. for 15 hours, and concentrated to deliver the crude product, which was then dissolved in 200 mL MTBE and stirred for 10 minutes and the mixture was filtered to deliver compound BB-32-4 (light yellow solid, 15 g, yield 69%).

Step 3: Synthesis of Compound BB-32-5

Compound BB-32-4 (25 g, 129 mmol) and anhydrous K$_2$CO$_3$ (37.6 g, 272 mmol) were dissolved in DMF (250 mL), DMAD (28.9 mL, 229.3 mmol) was added dropwise slowly at 0° C. The reaction mixture was stirred at r.t. for 48 hours, then poured into 300 mL H$_2$O, a large amount of solid was precipitated and filtered, the cake was preserved. The filtrate was extracted with PE/EA (3×300 mL), the organic phases were combined, washed with H$_2$O (50 mL), saturated brine (50 mL), dried over anhydrous sodium sulfate, and concentrated. The resulting crude product together with the cake obtained were purified by flash column instrument (eluting agent: DCM/PE=1/1) to deliver the target compound BB-32-5 (yellow solid, 4.8 g, yield 10%). $^1$H NMR (400 MHz, CDCl$_3$): δ 7.60 (s, 1H), 7.13 (s, 1H), 3.98-4.00 (s, 6H), 3.90-3.94 (s, 3H). MS (ESI) m/z: 333.0 [M+H]$^+$.

Step 4: Synthesis of Compound BB-32-6

Compound BB-32-5 (4.8 g, 14.5 mmol) was dissolved in a mixed solution of conc. sulphuric acid (25 mL, 450 mmol) and H$_2$O (10 mL), the reaction mixture was heated to 120° C. and stirred for 16 hours. The reaction mixture was poured into 200 mL ice-water, a large amount of solid was precipitated and filtered. The filtrate was extracted with EA (100 mL×4). The organic phases were combined, dried over anhydrous sodium sulfate directly, and concentrated to remove the solvent. The residue together with the cake obtained were dried to deliver the target compound BB-32-6 (yellow solid, 4.2 g, crude product), which was used for the next step directly without purification. MS (ESI) m/z: 247.0 [M+H]$^+$.

Step 5: Synthesis of Compound BB-32-7

Compound BB-32-6 (4.2 g, 17 mmol) was dissolved in methanol (50 mL), conc. sulphuric acid (5 mL) was added dropwise slowly, and the reaction was refluxed at 90° C. for 2 hours. The reaction mixture was concentrated, the residue was diluted with H$_2$O (50 mL), then extracted with EA (3×50 mL). The organic phases were combined, dried over anhydrous sodium sulfate, and concentrated. The resulting solid was isolated and purified by fast chromatography column (eluting agent: methanol/DCM=1/10) to deliver the target compound BB-32-7 (yellow solid, 2.7 g, yield 61%). MS (ESI) m/z: 261.0 [M+H]$^+$.

Step 6: Synthesis of Compound BB-32-8

Compound BB-32-7 (1.2 g, 4.6 mmol) was dissolved in DCM (15 mL), DIPEA (1.19 g, 9.2 mmol) and N-(trifluoromethyl)benzenesulphonamide (3.2 g, 8.98 mmol) were added sequentially at r.t. The reaction mixture was stirred at r.t. for 3 hours, then N-(trifluoromethyl)benzenesulphonamide (1 g, 2.8 mmol) was further added, and concentrated to remove the solvent. The resulting solid was isolated and purified by fast chromatography column (eluting agent: PE/DCM=10/1) to deliver the target compound BB-32-8 (yellow solid, 1.2 g, yield 67%). $^1$H NMR (400 MHz, CDCl$_3$): δ 7.76 (s, 1H), 7.35 (s, 1H), 7.26-7.28 (m, 1H).

Step 7: Synthesis of Compound BB-32-9

Compound BB-32-8 (0.5 g, 1.27 mmol) was dissolved in dioxane (5 mL), cyclopropylboronic acid (0.219 g, 2.54 mmol), K$_3$PO$_4$ (0.812 g, 3.82 mmol) and 1,1'-bis(di-tert-butylphosphino)ferrocene-palladium(II) dichloride dichloromethane complex (0.05 g, 0.06 mmol) were added sequentially. The reaction mixture was stirred at 90° C. and refluxed for 3 hours under nitrogen gas atmosphere, then cooled to r.t., filtered to remove the insolubles. The filtrate was poured into a mixture of EA (50 mL) and H$_2$O (20 mL) and stationarily partitioned, the organic phase was dried over anhydrous sodium sulfate, and concentrated. The resulting solid was isolated and purified by preparative chromatography plate (developing agent: PE/EA=5/1) to deliver the target compound BB-32-9 (yellow oil, 0.041 g, yield 11%). MS (ESI) m/z: 285.0 [M+H]$^+$.

Step 8: Synthesis of Compound BB-32-10

Compound BB-32-9 (0.04 g, 0.14 mmol) was dissolved in DMF (0.5 mL), NCS (0.028 g, 0.21 mmol) was added. The reaction was stirred at 60° C. for 1 hour, then diluted with H$_2$O, extracted with PE/DCM (3×20 mL). The organic phases were combined, washed with saturated brine, dried over anhydrous sodium sulfate, and concentrated. The resulting solid was isolated and purified by preparative chromatography plate (eluting agent: PE/EA=10/1) to deliver the target compound BB-32-10 (yellow oil, 0.046 g, yield 100%). MS (ESI) m/z: 319.0 [M+H]$^+$.

Step 9: Synthesis of Compound BB-32

Compound BB-32-10 (0.046 g, 0.15 mmol) was dissolved in a mixed solution of methanol (2 mL) and H$_2$O (0.4 mL), lithium hydroxide monohydrate (0.037 g, 0.75 mmol) was added. The reaction mixture was stirred at r.t. overnight, concentrated to remove methanol, then pH of the reaction mixture was adjusted to 1 with 1M dilute hydrochloric acid, the mixture was extracted with DCM (3×20 mL). The organic phases were combined, dried over anhydrous sodium sulfate, and concentrated to deliver the crude product of the target compound BB-32 (gray solid, 0.028 g, yield 62%), which was used for the next step directly without purification. MS (ESI) m/z: 305.0 [M+H]$^+$.

References 33 to 41: Fragment BB-33 to 41

The reference examples in the below table were synthesized according to the steps 1-5 in reference 20 (fragment BB-20).

| Examples | Structure | MS m/z | Fragment |
|---|---|---|---|
| 33 | | 144 [M + H]$^+$ | BB-33 |
| 34 | | 172 [M + H]$^+$ | BB-34 |
| 35 | | 166 [M + H]$^+$ | BB-35 |
| 36 | 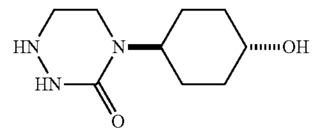 | 200 [M + H]$^+$ | BB-36 |
| 37 | 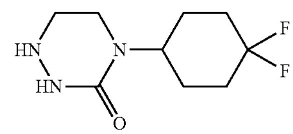 [SMILES: O=C1NNCCN1C1CCC(F)(F)CC1] | 220 [M + H]$^+$ | BB-37 |
| 38 | 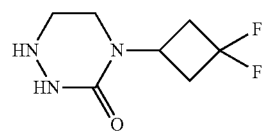 [SMILES: O=C1NNCCN1C1CC(F)(F)C1] | 192 [M + H]$^+$ | BB-38 |
| 39 | 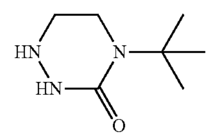 | 158 [M + H]$^+$ | BB-39 |
| 40 | 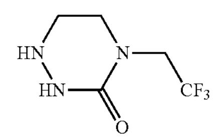 [SMILES: O=C1NNCCN1CC(F)(F)F] | 184 [M + H]$^+$ | BB-40 |
| 41 | 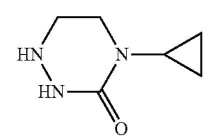 | 142 [M + H]$^+$ | BB-41 |

Embodiment 1: Compound YD_0346

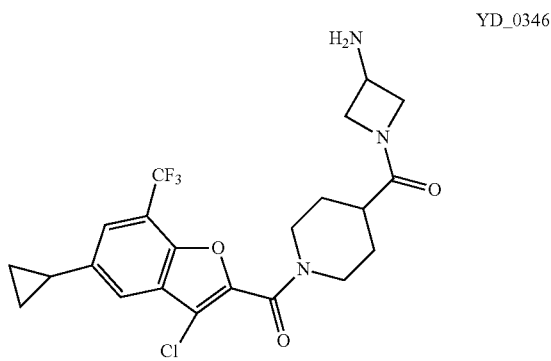 [SMILES: NC1CN(C(=O)C2CCN(C(=O)c3oc4c(C(F)(F)F)cc(C5CC5)cc4c3Cl)CC2)C1]

YD_0346

Synthetic Route:

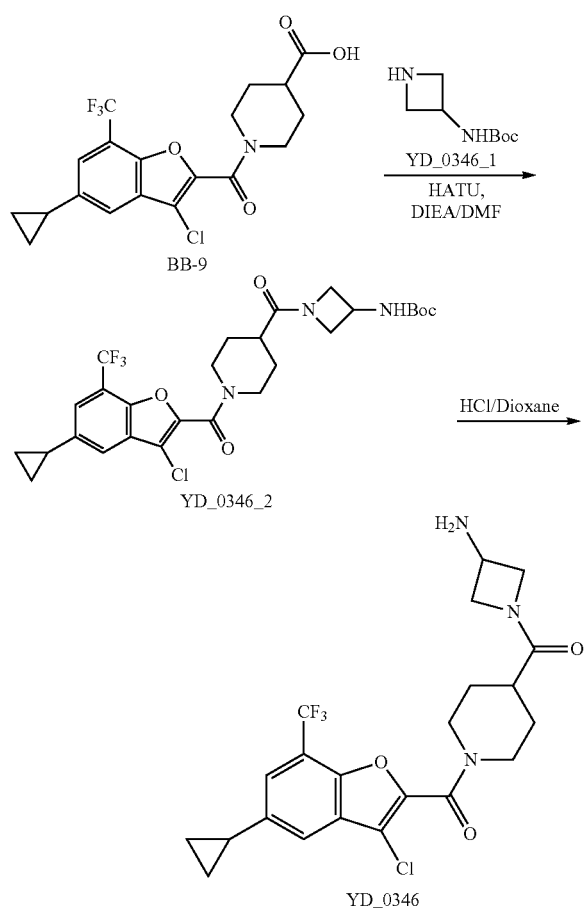

Step 1: Synthesis of Compound YD_0346_2

Compound BB-9 (0.035 g, 0.084 mmol) and compound YD_0346_1 (0.019 g, 0.093 mmol) were dissolved in DMF (2 mL), then HATU (0.048 g, 0.126 mmol) and DIPEA (0.032 g, 0.253 mmol) were added, the reaction mixture was stirred at r.t. for 3 hours. After the reaction was complete, EA was added, the organic phase was washed with $H_2O$ and saturated brine, dried over anhydrous sodium sulfate, filtered. The filtrate was concentrated under reduced pressure to remove the solvent thereby delivering the crude product, the crude was isolated and purified by thin silica gel plate (developing agent: EA/PE=1/2) to deliver the target compound YD_0346_2 (white solid, 0.040 g, yield 83%). MS (ESI) m/z: 570[M+H]$^+$, 541 [M−56+H]$^+$.

Step 2: Synthesis of Compound YD_0346

Compound YD_0346_2 was dissolved in THF (1 mL), then HCl/1,4-dioxane (4M, 2 mL) was added, the reaction mixture was stirred at 20° C. for 2 hours. Then the mixture was concentrated under reduced pressure to remove the solvent, the residue was isolated and purified by preparative HPLC (column: Gemini 150*25 mm*5 m, eluting agent: MeCN+0.075% HCl, $H_2O$+0.075% HCl), followed by frozen drying to deliver the target compound YD_0346 (white solid, 0.0155 g, yield 43.6%). $^1$H NMR (400 MHz, MeOD) =7.68-7.60 (m, 1H), 7.60-7.54 (m, 1H), 4.74-4.54 (m, 2H), 4.33 (d, J=8.0 Hz, 2H), 4.23-4.12 (m, 1H), 4.00 (d, J=4.0 Hz, 2H), 3.86-3.78 (m, 1H), 3.76-3.68 (m, 1H), 3.64-3.35 (m, 1H), 3.20-2.99 (m, 1H), 2.80-2.61 (m, 1H), 2.25-2.14 (m, 1H), 2.06-1.66 (m, 4H), 1.19-1.07 (m, 2H), 0.89-0.77 (m, 2H). MS (ESI) m/z: 470 [M+H]$^+$.

The embodiments in the table below were synthesized according to the steps 1-2 in embodiment 1 (compound YD_0346)

| Embodiment | Structure | Fragment 1 | | Fragment 2 | MS m/z | Compound |
|---|---|---|---|---|---|---|
| 2 | (structure) | (structure) | BB-9 | ClH·HN— | 443 [M + H]⁺ | YD_0273 |
| 3 | (structure) | (structure) | BB-9 | HN(iPr)Me | 471 [M + H]⁺ | YD_0302 |
| 4 | (structure) | (structure) | BB-9 | HO-azetidine | 471 [M + H]⁺ | YD_0303 |

| Embodiment | Structure | Fragment 1 | | Fragment 2 | MS m/z | Compound |
|---|---|---|---|---|---|---|
| 5 | 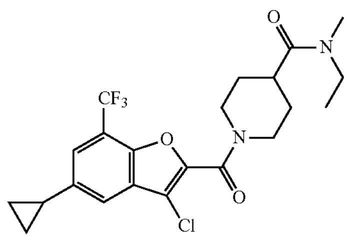 [SMILES: CCN(C)C(=O)C1CCN(C(=O)c2oc3c(C(F)(F)F)cc(C4CC4)cc3c2Cl)CC1] | | BB-9 | HN-Et (N-methyl ethylamine) | 457 [M + H]⁺ | YD_0304 |
| 6 | 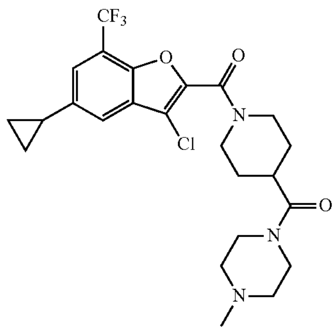 [SMILES: CN1CCN(C(=O)C2CCN(C(=O)c3oc4c(C(F)(F)F)cc(C5CC5)cc4c3Cl)CC2)CC1] | | BB-9 | 1-methylpiperazine | 498 [M + H]⁺ | YD_0305 |
| 7 | 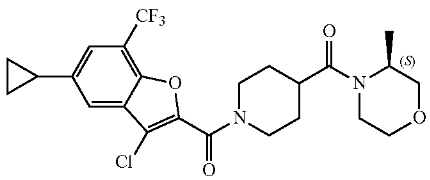 | | BB-9 | (S)-3-methylmorpholine | 499 [M + H]⁺ | YD_0311 |

| Embodiment | Structure | Fragment 1 | Fragment 2 | MS m/z | Compound |
|---|---|---|---|---|---|
| 8 | 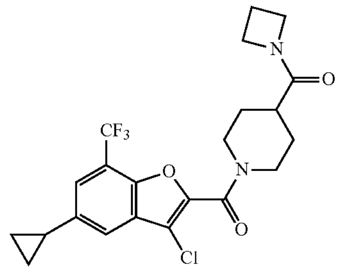 [SMILES: O=C(c1oc2c(C(F)(F)F)cc(C3CC3)cc2c1Cl)N1CCC(C(=O)N2CCC2)CC1] |  BB-9 |  | 455 [M + H]⁺ | YD_0313 |
| 9 | 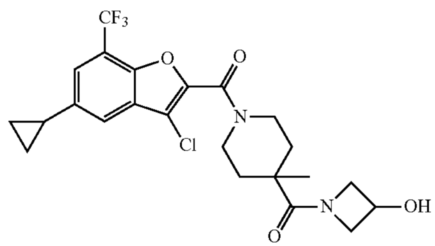 [SMILES: CC1(C(=O)N2CC(O)C2)CCN(C(=O)c2oc3c(C(F)(F)F)cc(C4CC4)cc3c2Cl)CC1] | 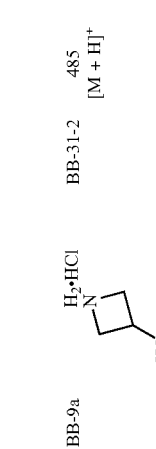 BB-9a |  BB-31-2 | 485 [M + H]⁺ | YD_0318 |
| 10 | 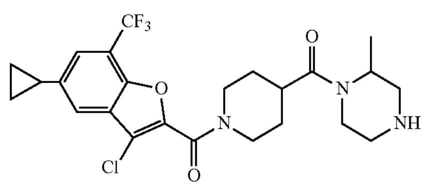 [SMILES: CC1CNCCN1C(=O)C1CCN(C(=O)c2oc3c(C(F)(F)F)cc(C4CC4)cc3c2Cl)CC1] |  BB-9 | 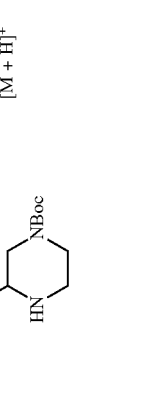 | 498 [M + H]⁺ | YD_0322 |
| 11 | 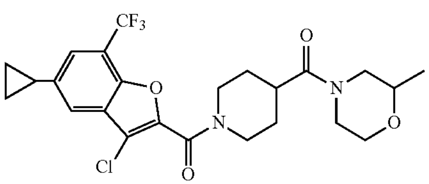 [SMILES: CC1CN(C(=O)C2CCN(C(=O)c3oc4c(C(F)(F)F)cc(C5CC5)cc4c3Cl)CC2)CCO1] | BB-9 | | 499 [M + H]⁺ | YD_0323 |

| Embodiment | Structure | Fragment 1 | | Fragment 2 | MS m/z | Compound |
|---|---|---|---|---|---|---|
| 12 | 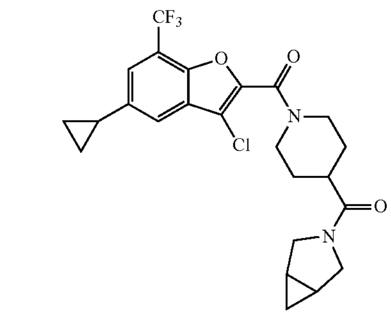 [SMILES: O=C(c1oc2c(C(F)(F)F)cc(C3CC3)cc2c1Cl)N1CCC(C(=O)N2CC3CC3C2)CC1] | | BB-9 | | 481 [M + H]⁺ | YD_0324 |
| 13 | 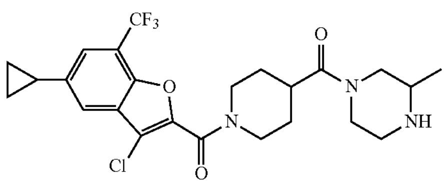 [SMILES: CC1CN(C(=O)C2CCN(C(=O)c3oc4c(C(F)(F)F)cc(C5CC5)cc4c3Cl)CC2)CCN1] | | BB-9 | | 498 [M + H]⁺ | YD_0326 |
| 14 | 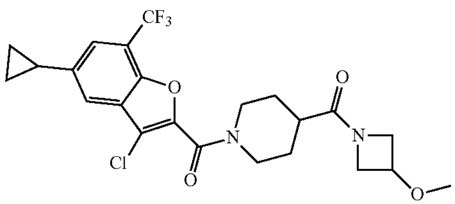 [SMILES: COC1CN(C(=O)C2CCN(C(=O)c3oc4c(C(F)(F)F)cc(C5CC5)cc4c3Cl)CC2)C1] | | BB-9 | | 485 [M + H]⁺ | YD_0340 |
| 15 | 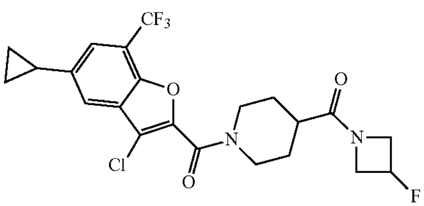 [SMILES: O=C(c1oc2c(C(F)(F)F)cc(C3CC3)cc2c1Cl)N1CCC(C(=O)N2CC(F)C2)CC1] | | BB-9 | | 473 [M + H]⁺ | YD_0342 |

-continued

| Embodiment | Structure | Fragment 1 | | Fragment 2 | | MS m/z | Compound |
|---|---|---|---|---|---|---|---|
| 16 | 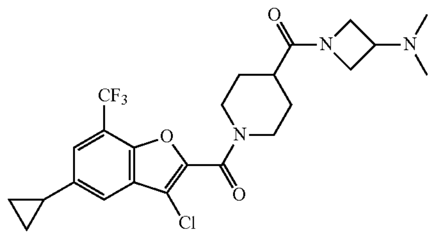 [SMILES: CN(C)C1CN(C(=O)C2CCN(C(=O)c3oc4c(C(F)(F)F)cc(C5CC5)cc4c3Cl)CC2)C1] | BB-9 | | BB-22 | | 498 [M + H]⁺ | YD_0343 |
| 17 | 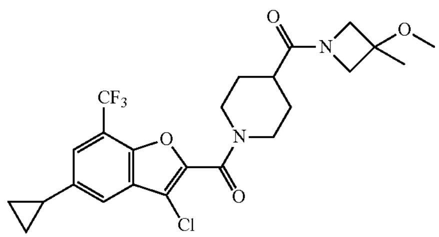 [SMILES: COC1(C)CN(C(=O)C2CCN(C(=O)c3oc4c(C(F)(F)F)cc(C5CC5)cc4c3Cl)CC2)C1] | BB-9 | | BB-24 | | 499 [M + H]⁺ | YD_0344 |
| 18 | 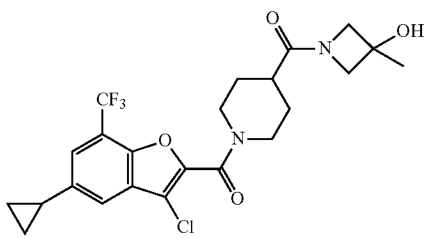 [SMILES: CC1(O)CN(C(=O)C2CCN(C(=O)c3oc4c(C(F)(F)F)cc(C5CC5)cc4c3Cl)CC2)C1] | BB-9 | | BB-23 | | 485 [M + H]⁺ | YD_0345 |

| Embodiment | Structure | Fragment 1 | Fragment 2 | MS m/z | Compound |
|---|---|---|---|---|---|
| 19 | 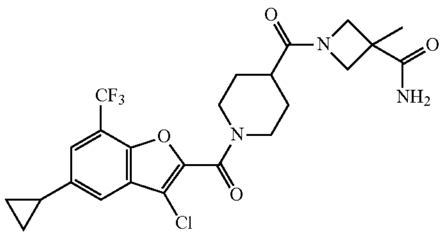 [SMILES: CC1(C(N)=O)CN(C(=O)C2CCN(C(=O)c3oc4c(C(F)(F)F)cc(C5CC5)cc4c3Cl)CC2)C1] | BB-9 | BB-25 | 512 [M + H]⁺ | YD_0348 |
| 20 | 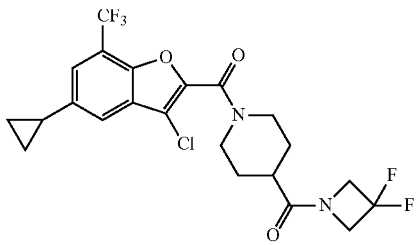 [SMILES: O=C(c1oc2c(C(F)(F)F)cc(C3CC3)cc2c1Cl)N1CCC(C(=O)N2CC(F)(F)C2)CC1] | BB-9 | | 491 [M + H]⁺ | YD_0349 |
| 21 | 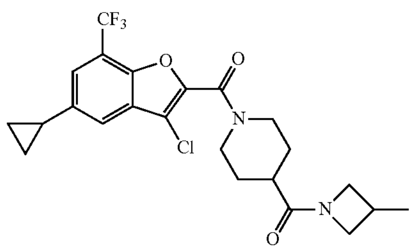 [SMILES: CC1CN(C(=O)C2CCN(C(=O)c3oc4c(C(F)(F)F)cc(C5CC5)cc4c3Cl)CC2)C1] | BB-9 | | 469 [M + H]⁺ | YD_0350 |

| Embodiment | Structure | Fragment 1 | Fragment 2 | MS m/z | Compound |
|---|---|---|---|---|---|
| 22 | (3-chloro-7-CF3-5-cyclopropyl-benzofuran-2-yl)carbonyl-piperidine-4-carbonyl-azetidine-3-CN | piperidine-4-carboxylic acid attached to (3-chloro-7-CF3-5-cyclopropyl-benzofuran-2-yl)carbonyl (BB-9) | azetidine-3-CN (BB-30) | 480 [M + H]+ | YD_0352 |
| 23 | (3-chloro-7-CF3-5-cyclopropyl-benzofuran-2-yl)carbonyl-piperidine-4-carbonyl-azetidine-3-CONH2 | piperidine-4-carboxylic acid attached to (3-chloro-7-CF3-5-cyclopropyl-benzofuran-2-yl)carbonyl (BB-9) | azetidine-3-CONH2 (BB-30a) | 498 [M + H]+ | YD_0353 |
| 24 | (3-chloro-7-CF3-5-cyclopropyl-benzofuran-2-yl)carbonyl-piperidine-4-carbonyl-azetidine-3-CH2OH | piperidine-4-carboxylic acid attached to (3-chloro-7-CF3-5-cyclopropyl-benzofuran-2-yl)carbonyl (BB-9) | azetidine-3-CH2OH (BB-26) | 485 [M + H]+ | YD_0355 |

Embodiment 25: YD_0327

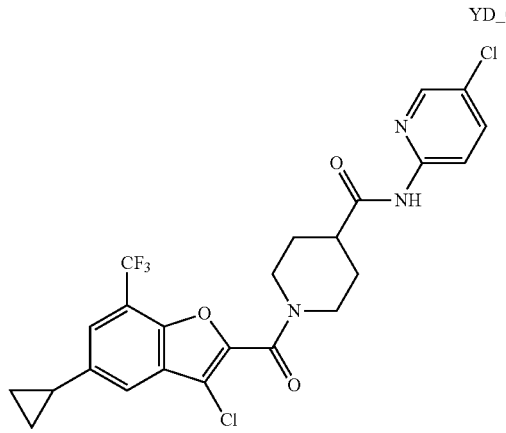

Synthetic Route:

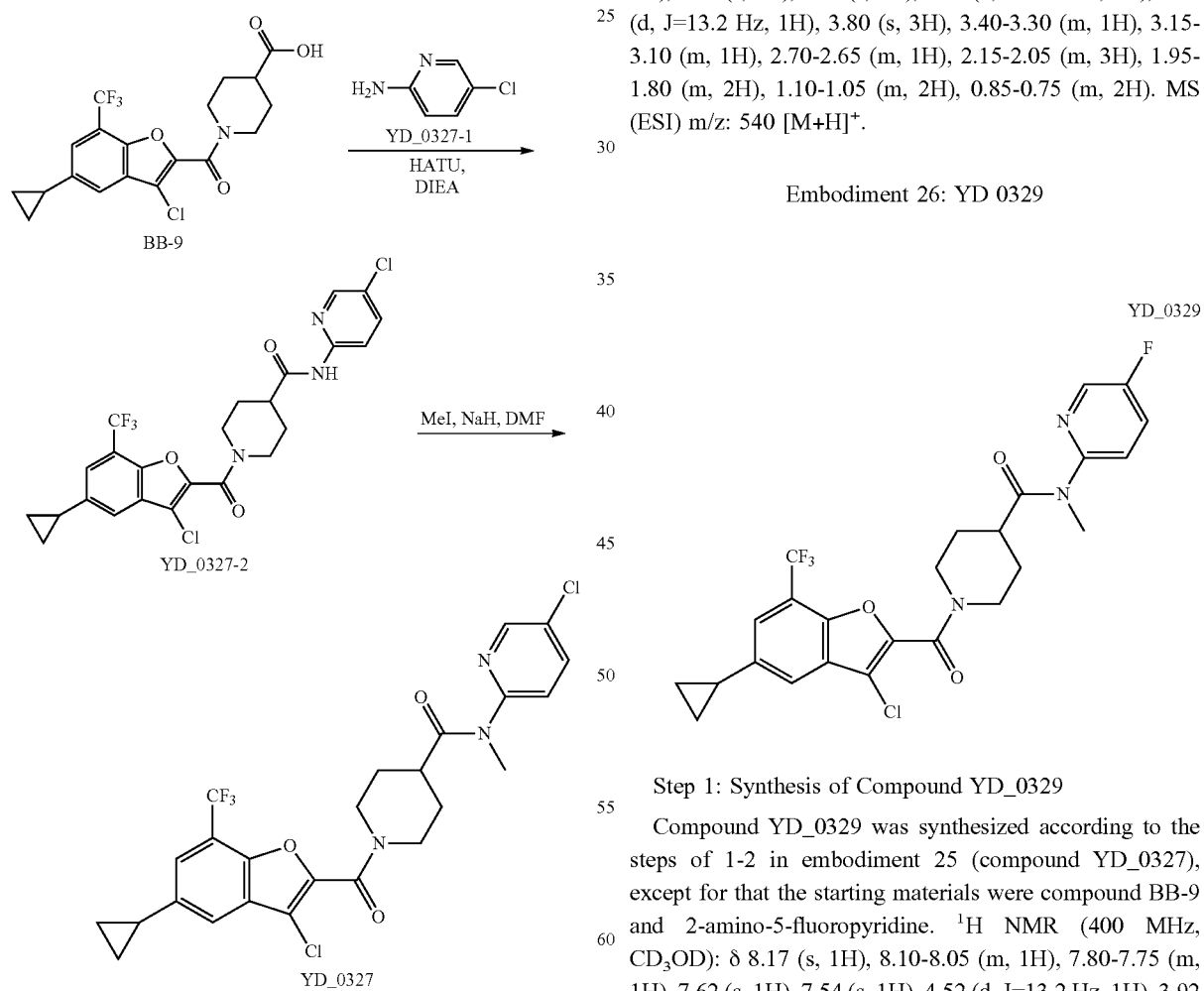

Step 1: Synthesis of Compound YD_0327-2

Compound BB-9 (0.100 g, 0.241 mmol), compound YD_0327-1 (0.046 g, 0.361 mmol) were dissolved in DMF (1 mL), DIPEA (0.093 g, 0.722 mmol) and HATU (0.137 g, 0.361 mmol) were added, the reaction mixture was stirred at 25° C. for 5 hours, $H_2O$ (2 mL) was added. The solid was filtered out and collected, the cake was purified by thin-layer chromatography plate (developing agent, EA/PE=1/2) to deliver compound YD_0327-2 (yellow solid, 0.040 g, yield 31.60%). MS (ESI) m/z: 527 $[M+H]^+$.

Step 2: Synthesis of Compound YD_0327

Compound YD_0327-2 (0.040 g, 0.076 mmol) was dissolved in DMF (1 mL), NaH (0.006 g, 0.152 mmol, 60%) was added, the reaction mixture was stirred at 25° C. for 10 minutes, MeI (0.054 g, 0.380 mmol) was added. The reaction mixture was stirred at 25° C. for 2 hours, then quenched with $H_2O$ (0.5 mL), and isolated and purified by preparative HPLC (column: Phenomenex Gemini C18 150*25 mm*5 μm, eluting agent: MeCN+0.05% $NH_3.H_2O$, $H_2O$+0.05% $NH_3.H_2O$) to deliver the target compound YD_0327 (yellow solid, 0.004 g, yield 9.74%). $^1$H NMR (400 MHz, $CD_3OD$): δ 8.19 (s, 1H), 7.98 (d, J=9.2 Hz, 1H), 7.72 (d, J=9.2 Hz, 1H), 7.61 (s, 1H), 7.53 (s, 1H), 4.51 (d, J=13.2 Hz, 1H), 3.92 (d, J=13.2 Hz, 1H), 3.80 (s, 3H), 3.40-3.30 (m, 1H), 3.15-3.10 (m, 1H), 2.70-2.65 (m, 1H), 2.15-2.05 (m, 3H), 1.95-1.80 (m, 2H), 1.10-1.05 (m, 2H), 0.85-0.75 (m, 2H). MS (ESI) m/z: 540 $[M+H]^+$.

Embodiment 26: YD_0329

Step 1: Synthesis of Compound YD_0329

Compound YD_0329 was synthesized according to the steps of 1-2 in embodiment 25 (compound YD_0327), except for that the starting materials were compound BB-9 and 2-amino-5-fluoropyridine. $^1$H NMR (400 MHz, $CD_3OD$): δ 8.17 (s, 1H), 8.10-8.05 (m, 1H), 7.80-7.75 (m, 1H), 7.62 (s, 1H), 7.54 (s, 1H), 4.52 (d, J=13.2 Hz, 1H), 3.92 (d, J=13.2 Hz, 1H), 3.83 (s, 3H), 3.40-3.30 (m, 1H), 3.15-3.10 (m, 1H), 2.70-2.65 (m, 1H), 2.15-2.05 (m, 3H), 1.95-1.80 (m, 2H), 1.10-1.05 (m, 2H), 0.85-0.75 (m, 2H). MS (ESI) m/z: 524 $[M+H]^+$.

Embodiment 27: YD_0321

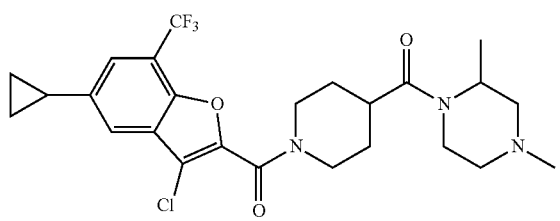

YD_0321

Synthetic Route:

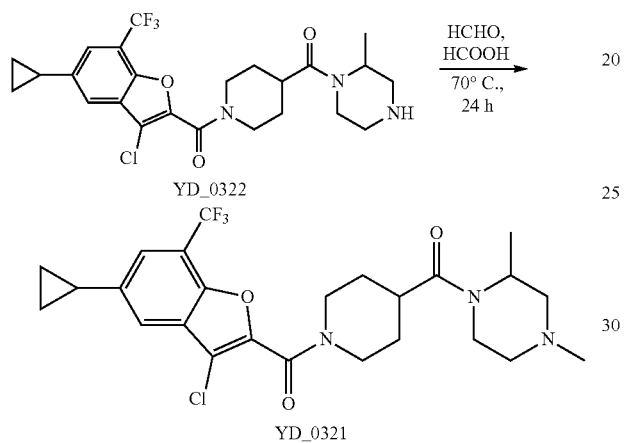

Step 1: Synthesis of Compound YD_0321

Compound YD_0322 (0.065 g, 0.130 mmol) was added to 2 mL MeOH, then aqueous formaldehyde solution (0.008 g, 0.266 mmol), formic acid (22 mg, 0.458 mmol) were added. The reaction mixture was stirred at 70° C. for 24 hours. The reaction mixture was evaporated to dry under reduced pressure, then isolated by preparative HPLC (column: Phenomenex Gemini C18 150*25 mm*5 µm, eluting agent: MeCN+0.05% NH$_3$.H$_2$O, H$_2$O+0.05% NH$_3$.H$_2$O) to deliver compound YD_0321 (0.008 g, yield 12%). MS-ESI: m/z: 512 [M+H]$^+$. $^1$H NMR (400 MHz, CDCl$_3$): δ 7.49 (m, 1H), 7.42 (m, 1H), 4.61-4.75 (m, 2H), 4.03-4.09 (m, 1H), 3.45-3.61 (m, 2H), 3.20-3.27 (m, 1H), 2.91-3.09 (m, 2H), 2.68-2.83 (m, 3H), 2.26 (s, 3H), 2.01-2.09 (m, 2H), 1.86-2.04 (m, 3H), 1.39-1.40 (m, 1H), 1.22-1.26 (m, 2H), 1.05-1.10 (m, 2H), 0.77-0.79 (m, 2H).

Embodiment 28: YD_0325

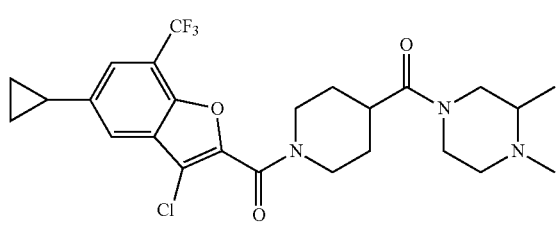

YD_0325

Step 1: Synthesis of Compound YD_0325

Compound YD_0325 was synthesized according to the step 1 in embodiment 27 (compound YD_0321), except for that the starting material was compound YD_0326. $^1$H NMR (400 MHz, CDCl$_3$): δ 7.62 (m, 1H), 7.49 (m, 1H), 4.55-4.63 (m, 1H), 4.31-4.46 (m, 1H), 4.02-4.11 (m, 1H), 3.58-3.80 (m, 1H), 3.12-3.43 (m, 2H), 2.79-3.10 (m, 4H), 2.49-2.56 (m, 1H), 2.31 (s, 3H), 2.01-2.11 (m, 2H), 1.72-1.96 (m, 4H), 1.12-1.21 (m, 2H), 0.77-0.79 (m, 2H). MS-ESI: m/z 512 [M+H]$^+$.

Embodiment 29: YD_0351

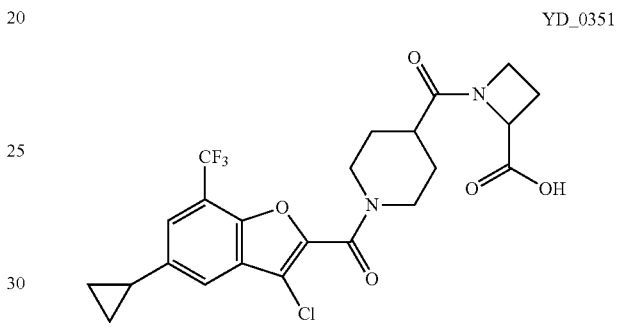

YD_0351

Synthetic Route:

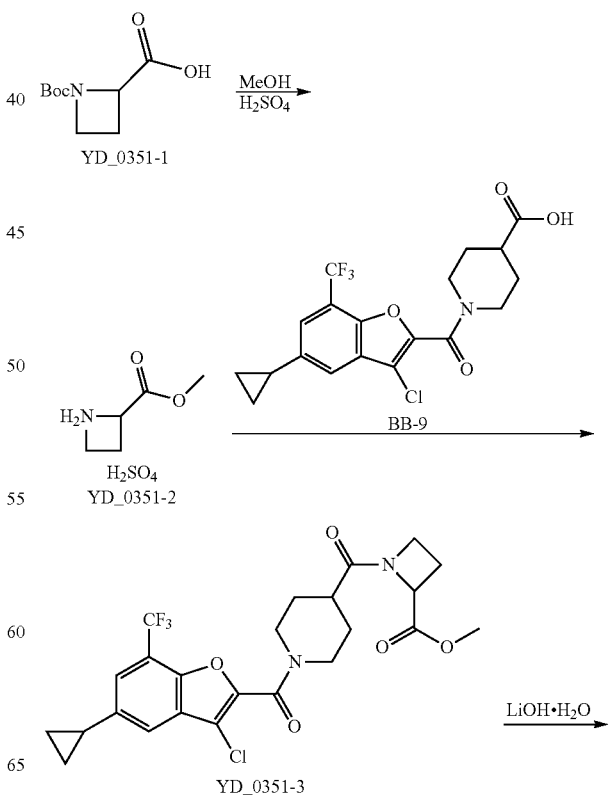

115
-continued

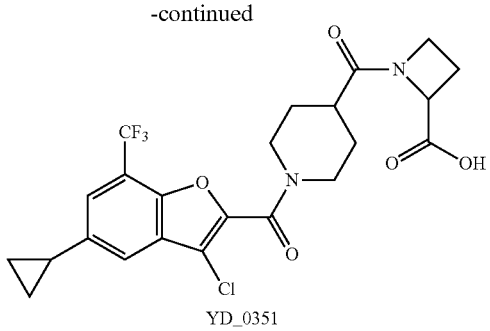

YD_0351

Step 1: Synthesis of Compound YD_0351-2

Compound YD_0351-1 (0.090 g, 0.449 mmol) was dissolved in MeOH (5 mL), then conc. sulfuric acid (0.008 g, 0.081 mmol) was added, the reaction mixture was stirred at reflux for 5 hours. After the reaction was complete, the solvent was removed by concentration under reduced pressure to deliver the crude product YD_0351-2 (yellow oil, 0.090 g, crude product) which was used for the next step directly. $^1$H NMR (400 MHz, CDCl$_3$): δ 5.19-5.14 (m, 1H), 4.18-4.12 (m, 1H), 3.99-3.94 (m, 1H), 3.71 (s, 3H), 2.86-2.82 (m, 1H), 2.75-2.69 (m, 1H).

Step 2: Synthesis of Compound YD_0351-3

Compound YD_0351-2 (0.031 g, 0.144 mmol) was dissolved in DMF (2 mL), then compound BB-9 (0.060 g, 0.144 mmol), DIPEA (0.093 g, 0.722 mmol) and HATU (0.066 g, 0.173 mmol) were added, the reaction mixture was stirred at r.t. for 6 hours. After the reaction was complete, H$_2$O (5 mL) was added, the mixture was extracted with EA (10 mL×2). The organic phases were combined and dried over sodium sulfate, filtered, and concentrated to deliver the crude product YD_0351-3 (yellow oil, 0.130 g, crude product). MS (ESI) m/z: 513 [M+H]$^+$.

Step 3: Synthesis of Compound YD_0351

Compound YD_0351-3 (0.130 g, 0.253 mmol) was dissolved in MeOH (3 mL) and H$_2$O (1 mL), then lithium hydroxide monohydrate (0.032 g, 0.760 mmol) was added, the reaction mixture was stirred at r.t. for 2 hours. After the reaction was complete, the solvent was removed by concentration under reduced pressure, the resulting residue was dissolved in H$_2$O again and pH was adjusted to about 2-3 with 2N aqueous hydrochloric acid solution. The solid was collected to deliver the crude product, which was isolated and purified by preparative HPLC (column: Synergy 150*30 mm, eluting agent: MeCN+0.075% TFA, H$_2$O+0.075% TFA) to deliver YD_0351 (white solid, 0.030 g, yield 24%). $^1$H NMR (400 MHz, CD$_3$OD): δ 7.64 (s, 1H), 7.56 (s, 1H), 5.15-5.11 (m, 0.5H), 4.71-4.75 (m, 0.5H), 4.61-4.57 (m, 1H), 4.36-4.29 (m, 1H), 4.01-3.96 (m, 2H), 3.39-3.34 (m, 0.5H), 3.14-3.03 (m, 0.5H), 3.02-2.85 (m, 0.5H), 2.75-2.73 (m, 2H), 2.59-2.52 (m, 0.5H), 2.21-2.16 (m, 2H), 1.83-1.80 (m, 4H), 1.14-1.09 (m, 2H), 0.84-0.82 (m, 2H). MS (ESI) m/z: 499 [M+H]$^+$.

116

Embodiment 30: YD_0019

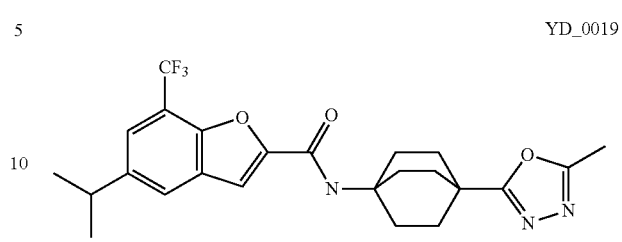

Synthetic Route:

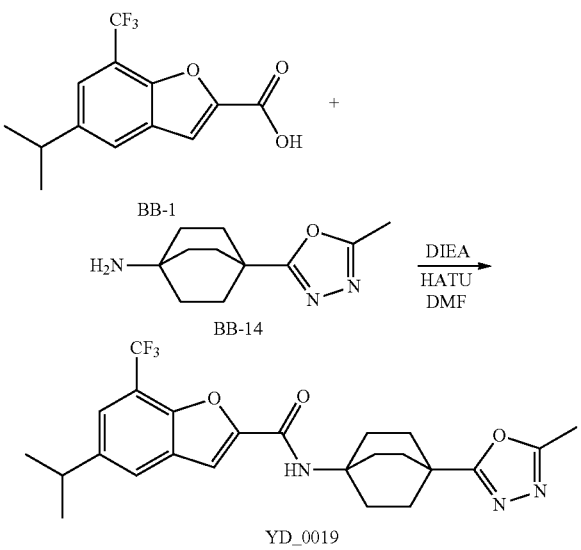

Step 1: Synthesis of Compound YD_0019

Compound BB-1 (0.035 g, 0.128 mmol) was dissolved in DMF (2 mL), then compound BB-14 (0.027 g, 0.128 mmol), DIPEA (0.050 g, 0.386 mmol) and HATU (0.063 g, 0.167 mmol) were added. The reaction mixture was stirred at r.t. for 2 hours. After the reaction was complete, EA (100 mL) was added, then the mixture was washed with brine, dried over anhydrous sodium sulfate, and concentrated to deliver the crude product, which was isolated by thick silica gel plate (developing agent: PE/EA=1/1) to deliver the target compound YD_0019 (white solid, 0.050 g, yield 84%). MS (ESI) m/z: 462 [M+H]$^+$. $^1$H NMR (400 MHz, MeOD): δ 7.87 (s, 1H), 7.62 (s, 1H), 7.55 (s, 1H), 3.15-3.11 (m, 1H), 2.52 (s, 3H), 2.13-2.26 (m, 12H), 1.36 (d, J=7.2 Hz, 6H).

The embodiments in the table below were synthesized according to the step 1 in embodiment 30 (compound YD_0019)

| Embodiments | Structure | Fragment 1 | Fragment 2 | MS m/z | Compound |
|---|---|---|---|---|---|
| 31 | 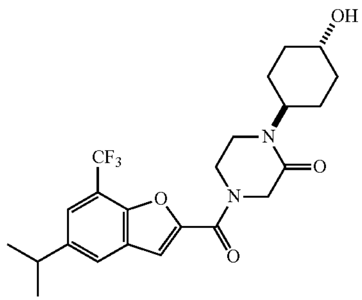 | | | BB-10 453 [M+H]+ | YD_0044 |
| 32 | 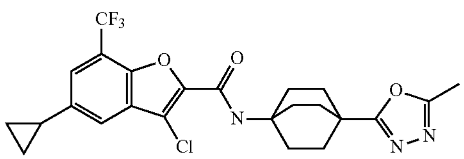 [SMILES: Cc1nnc(C23CCC(NC(=O)c4oc5c(C(F)(F)F)cc(C6CC6)cc5c4Cl)(CC2)CC3)o1] | | BB-2 | BB-14 494 [M+H]+ | YD_0056 |
| 33 | 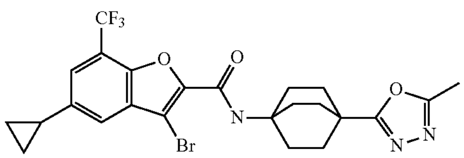 [SMILES: Cc1nnc(C23CCC(NC(=O)c4oc5c(C(F)(F)F)cc(C6CC6)cc5c4Br)(CC2)CC3)o1] | | BB-4 | BB-14 540 [M+H]+ | YD_0057 |
| 34 | 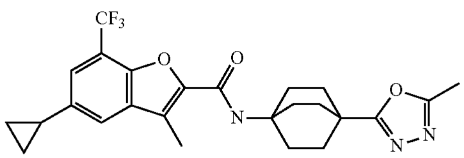 [SMILES: Cc1nnc(C23CCC(NC(=O)c4oc5c(C(F)(F)F)cc(C6CC6)cc5c4C)(CC2)CC3)o1] | | BB-5 | BB-14 474 [M+H]+ | YD_0058 |
| 35 | 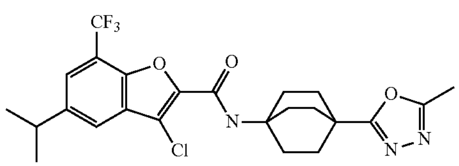 [SMILES: Cc1nnc(C23CCC(NC(=O)c4oc5c(C(F)(F)F)cc(C(C)C)cc5c4Cl)(CC2)CC3)o1] | | BB-3 | BB-14 496 [M+H]+ | YD_0059 |

-continued

| Embodiments | Structure | Fragment 1 | Fragment 2 | MS m/z | Compound |
|---|---|---|---|---|---|
| 36 | 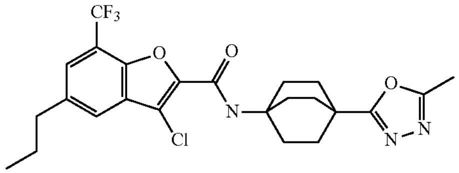 [SMILES: CCCc1cc(C(F)(F)F)c2oc(C(=O)NC34CCC(c5nnc(C)o5)(CC3)CC4)c(Cl)c2c1] | BB-3a | BB-14 | 496 [M + H]+ | YD_0060 |
| 37 | 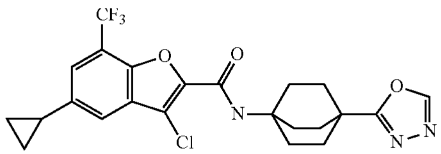 [SMILES: O=C(NC12CCC(c3nnco3)(CC1)CC2)c1oc2c(C(F)(F)F)cc(C3CC3)cc2c1Cl] | BB-2 | BB-13 | 480 [M + H]+ | YD_0122 |
| 38 | 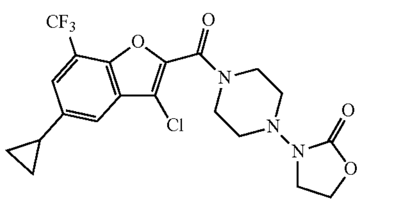 [SMILES: O=C(c1oc2c(C(F)(F)F)cc(C3CC3)cc2c1Cl)N1CCN(N2CCOC2=O)CC1] | BB-2 | BB-17 | 458 [M + H]+ | YD_0214 |
| 39 | 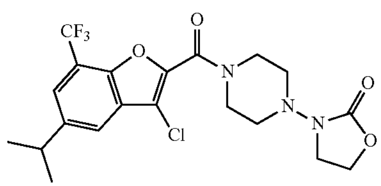 [SMILES: CC(C)c1cc(C(F)(F)F)c2oc(C(=O)N3CCN(N4CCOC4=O)CC3)c(Cl)c2c1] | BB-3 | BB-17 | 460 [M + H]+ | YD_0215 |
| 40 | 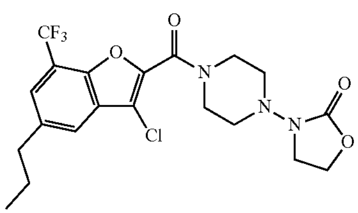 [SMILES: CCCc1cc(C(F)(F)F)c2oc(C(=O)N3CCN(N4CCOC4=O)CC3)c(Cl)c2c1] | BB-3a | BB-17 | 460 [M + H]+ | YD_0216 |

-continued

| Embodi-ments | Structure | Fragment 1 | | Fragment 2 | | MS m/z | Compound |
|---|---|---|---|---|---|---|---|
| 41 | 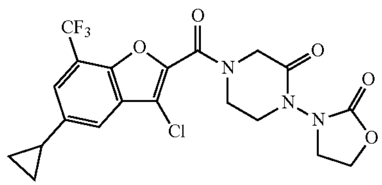 [SMILES: O=C(c1oc2c(C(F)(F)F)cc(C3CC3)cc2c1Cl)N1CCN(N2CCOC2=O)C(=O)C1] | | BB-8 | | BB-11 | 472 [M + H]+ | YD_0219 |
| 42 | 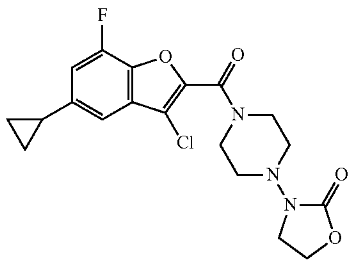 [SMILES: O=C(c1oc2c(F)cc(C3CC3)cc2c1Cl)N1CCN(N2CCOC2=O)CC1] | | BB-7 | | BB-17 | 408 [M + H]+ | YD_0245 |
| 43 | 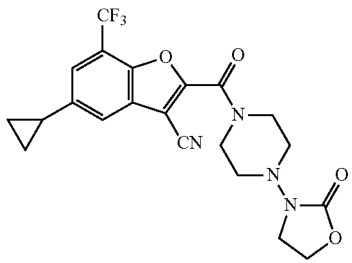 [SMILES: N#Cc1c(C(=O)N2CCN(N3CCOC3=O)CC2)oc2c(C(F)(F)F)cc(C3CC3)cc12] | | BB-6 | | BB-17 | 449 [M + H]+ | YD_0250 |
| 44 | 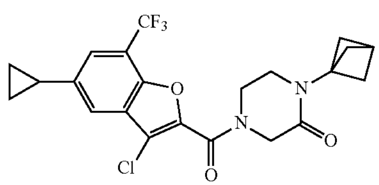 [SMILES: O=C(c1oc2c(C(F)(F)F)cc(C3CC3)cc2c1Cl)N1CCN(C23CC(C2)C3)C(=O)C1] | | BB-2 | | BB-15 | 453 [M + H]+ | YD_0253 |

-continued

| Embodiments | Structure | Fragment 1 | | Fragment 2 | | MS m/z | Compound |
|---|---|---|---|---|---|---|---|
| 45 | 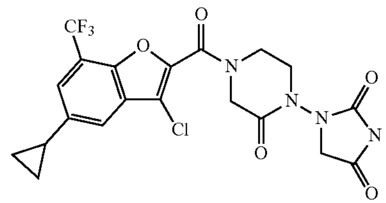 [SMILES: O=C1CN(N2CCN(C(=O)c3oc4c(C(F)(F)F)cc(C5CC5)cc4c3Cl)CC2=O)C(=O)N1] | | BB-2 | | BB-12 | 485 [M + H]⁺ | YD_0272 |
| 46 | 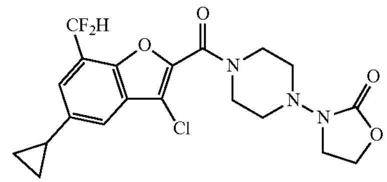 [SMILES: O=C(c1oc2c(C(F)F)cc(C3CC3)cc2c1Cl)N1CCN(N2CCOC2=O)CC1] | | BB-8 | | BB-17 | 440 [M + H]⁺ | YD_0278 |
| 47 | 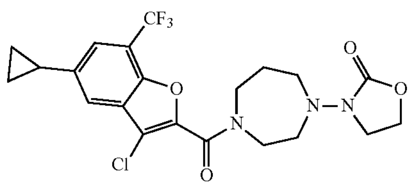 [SMILES: O=C(c1oc2c(C(F)(F)F)cc(C3CC3)cc2c1Cl)N1CCCN(N2CCOC2=O)CC1] | | BB-3 | | BB-18 | 472 [M + H]⁺ | YD_0279 |
| 48 | 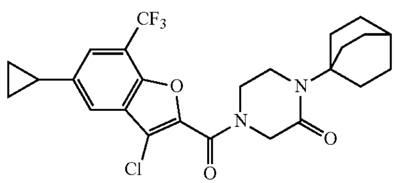 [SMILES: O=C(c1oc2c(C(F)(F)F)cc(C3CC3)cc2c1Cl)N1CCN(C23CCC(CC2)CC3)C(=O)C1] | | BB-2 | | BB-16 | 495 [M + H]⁺ | YD_0280 |

-continued

| Embodiments | Structure | Fragment 1 | | Fragment 2 | MS m/z | Compound |
|---|---|---|---|---|---|---|
| 49 | 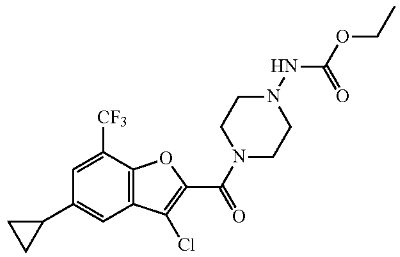 [SMILES: CCOC(=O)NN1CCN(C(=O)c2oc3c(C(F)(F)F)cc(C4CC4)cc3c2Cl)CC1] | | BB-2 | | 460 [M + H]+ BB-19 | YD_0312 |
| 50 | 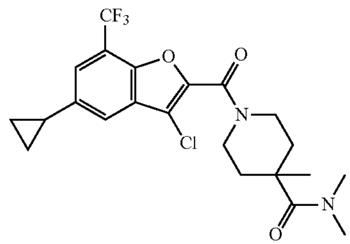 [SMILES: CN(C)C(=O)C1(C)CCN(C(=O)c2oc3c(C(F)(F)F)cc(C4CC4)cc3c2Cl)CC1] | | BB-2 | | 457 [M + H]+ BB-27 | YD_0317 |
| 51 | 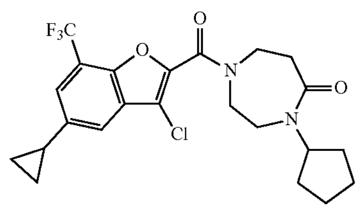 [SMILES: O=C(c1oc2c(C(F)(F)F)cc(C3CC3)cc2c1Cl)N1CCC(=O)N(C2CCCC2)CC1] | | BB-2 | | 469 [M + H]+ BB-28 | YD_0330 |
| 52 | 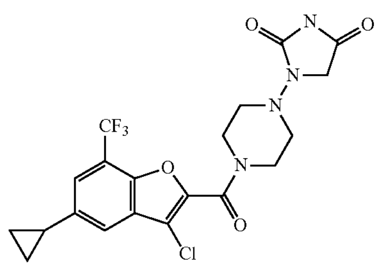 [SMILES: O=C1CN(N2CCN(C(=O)c3oc4c(C(F)(F)F)cc(C5CC5)cc4c3Cl)CC2)C(=O)N1] | | BB-2 | | 471 [M + H]+ BB-29 | YD_0331 |

| Embodiments | Structure | Fragment 1 | | Fragment 2 | | MS m/z | Compound |
|---|---|---|---|---|---|---|---|
| 53 | 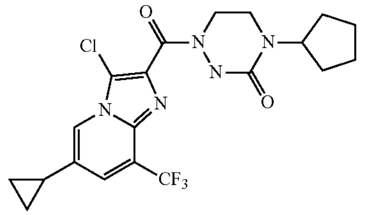 [SMILES: O=C(c1nc2c(C(F)(F)F)cc(C3CC3)cn2c1Cl)N1CCN(C2CCCC2)C(=O)N1] | | BB-21 | | BB-20 | 456 [M + H]⁺ | YA_0338 |
| 54 | 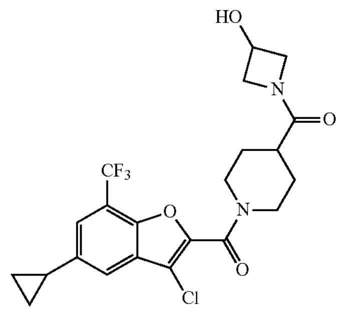 [SMILES: O=C(c1oc2c(C(F)(F)F)cc(C3CC3)cc2c1Cl)N1CCC(C(=O)N2CC(O)C2)CC1] | | BB-6 | | BB-31 | 462 [M + H]⁺ | YD_0356 |
| 55 | 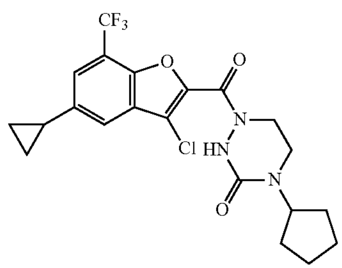 [SMILES: O=C(c1oc2c(C(F)(F)F)cc(C3CC3)cc2c1Cl)N1CCN(C2CCCC2)C(=O)N1] | | BB-2 | | BB-20 | 456 [M + H]⁺ | YD_0357 |
| 56 | 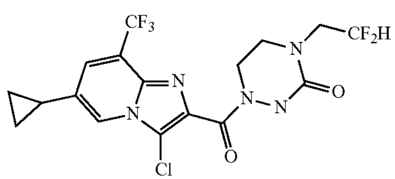 [SMILES: O=C1NN(C(=O)c2nc3c(C(F)(F)F)cc(C4CC4)cn3c2Cl)CCN1CC(F)F] | | BB-21 | | BB-35 | 452 [M + H]⁺ | YA_0358 |

| Embodiments | Structure | Fragment 1 | | Fragment 2 | | Compound | MS m/z |
|---|---|---|---|---|---|---|---|
| 57 | 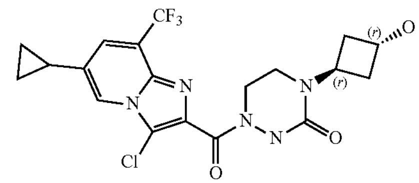 [SMILES: O=C(c1nc2c(C(F)(F)F)cc(C3CC3)cn2c1Cl)N1CCN([C@H]2C[C@H](O)C2)C(=O)N1] | | BB-21 | | BB-34 | YA_0359 | 458 [M + H]+ |
| 58 | 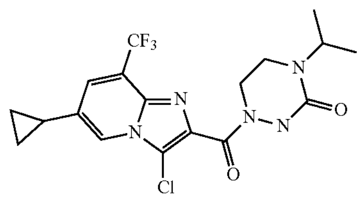 [SMILES: CC(C)N1CCN(C(=O)c2nc3c(C(F)(F)F)cc(C4CC4)cn3c2Cl)NC1=O] | | BB-21 | | BB-33 | YA_0360 | 430 [M + H]+ |
| 59 | 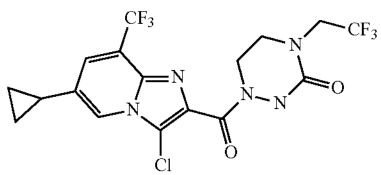 [SMILES: O=C1NN(C(=O)c2nc3c(C(F)(F)F)cc(C4CC4)cn3c2Cl)CCN1CC(F)(F)F] | | BB-21 | | BB-40 | YA_0361 | 470 [M + H]+ |
| 60 | 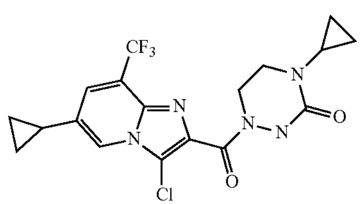 [SMILES: O=C(c1nc2c(C(F)(F)F)cc(C3CC3)cn2c1Cl)N1CCN(C2CC2)C(=O)N1] | | BB-21 | | BB-41 | YA_0362 | 428 [M + H]+ |
| 61 | 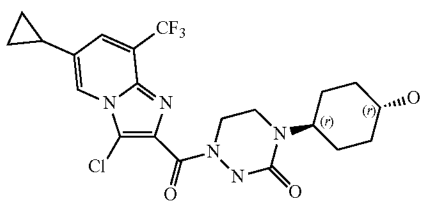 [SMILES: O=C(c1nc2c(C(F)(F)F)cc(C3CC3)cn2c1Cl)N1CCN([C@H]2CC[C@H](O)CC2)C(=O)N1] | | BB-21 | | BB-36 | YA_0363 | 486 [M + H]+ |

-continued

| Embodi-ments | Structure | Fragment 1 | Fragment 2 | MS m/z | Compound |
|---|---|---|---|---|---|
| 62 | 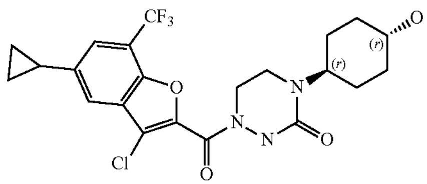 [SMILES: O=C(c1oc2c(C(F)(F)F)cc(C3CC3)cc2c1Cl)N1CCN([C@H]2CC[C@H](O)CC2)C(=O)N1] | | BB-2 | BB-36 486 [M + H]⁺ | YD_0365 |
| 63 | 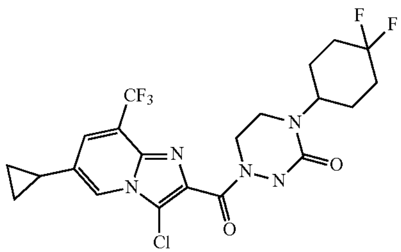 [SMILES: O=C(c1nc2c(C(F)(F)F)cc(C3CC3)cn2c1Cl)N1CCN(C2CCC(F)(F)CC2)C(=O)N1] | | BB-21 | BB-37 506 [M + H]⁺ | YA_0366 |
| 64 | 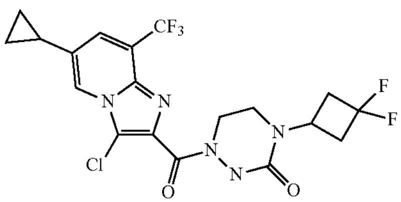 [SMILES: O=C(c1nc2c(C(F)(F)F)cc(C3CC3)cn2c1Cl)N1CCN(C2CC(F)(F)C2)C(=O)N1] | | BB-21 | BB-38 478 [M + H]⁺ | YA_0367 |
| 65 | 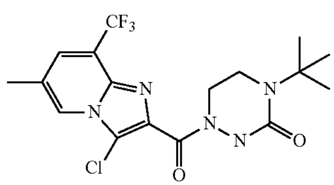 | | BB-21 | BB-39 444 [M + H]⁺ | YA_0368 |

| Embodiments | Structure | Fragment 1 | | Fragment 2 | MS m/z | Compound |
|---|---|---|---|---|---|---|
| 66 | 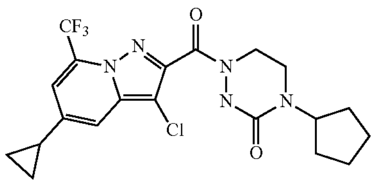 [SMILES: O=C(c1nn2c(C(F)(F)F)cc(C3CC3)cc2c1Cl)N1CCN(C2CCCC2)C(=O)N1] | | BB-32 | | BB-20 456 [M + H]⁺ | YH_0369 |
| 67 | 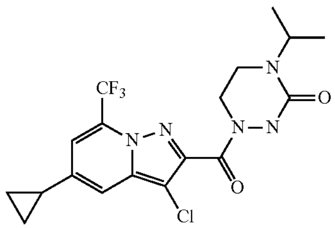 [SMILES: CC(C)N1CCN(C(=O)c2nn3c(C(F)(F)F)cc(C4CC4)cc3c2Cl)NC1=O] | | BB-32 | | BB-33 430 [M + H]⁺ | YH_0373 |
| 68 | 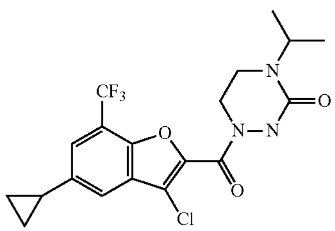 [SMILES: CC(C)N1CCN(C(=O)c2oc3c(C(F)(F)F)cc(C4CC4)cc3c2Cl)NC1=O] | | BB-2 | | BB-33 430 [M + H]⁺ | YD_0374 |

Experiment 1: Assay In Vitro

Experimental Objective:

The $EC_{50}$ and $CC_{50}$ values of anti-HCV compounds were determined by HCV genotype 1a (HCV-1a) and 1b (HCV-1b) stable transfected replication (replicon) cells. The source of genotype 1a replicon is H77 clones containing K1691R, K2040R and S2204I adaptive mutations. The source of genotype 1b replicon is Con1 clones containing E1202G, T1280I and K1846T adaptive mutations.

Background Introduction:

HCV 1a (HCV-1a) and 1b (HCV-1b) gene subtype replicon system contains the related HCV gene subtype non-structural protein gene, G418 resistance gene NEO and luciferase gene, which results in that HCV related protein and luciferase can be stably expressed in cells. By detecting the level of expression of luciferase gene, the level of HCV replication can be determined. Therefore, the system is used as a model for screening the activity of anti-HCV compound in vitro.

Experimental Materials:

HCV replicon cell lines: HCV-1a and HCV-1b cells

Cell culture medium: DMEM (Invitrogen, Cat. #11960077) medium, add 10% fetal bovine serum (FBS, Sigma, Cat. #12003C) and 1% penicillin-streptomycin (penicillin 5000 IU/mL, streptomycin 10 mg/mL, Hyclone, Cat. #SV30010)

Trypsin (Invitrogen, Cat. #25200072)
PBS (Invitrogen, Cat. #10010023)
Trypan blue (Invitrogen, Cat. #15250061)
Cell Titer-fluor (Promega, Cat. #G6082)
Bright-Glo (Promega, Cat. #E2650)
$CO_2$ incubator, Thermo 240 I
Multidrop, Thermo
POD 810 Plate Assembler, Labcyte
Scepter Handheld Automated Cell Counter, Millipore
Microplate Spectrophotometer, Molecular Device.

Experimental Procedure and Method:

a) Preparation, Dilution and Addition of Compound Solution:

The compound powder was dissolved in 100% DMSO. Then the compound was diluted 5 times with 6 points, and added into the cell plate with Echo liquid handler. Ensure the final concentration of DMSO was 0.5%. Each compound was tested in duplicate.

b) Cell Culture (HCV-1a or HCV-1b Replicon Cell):

1) Absorbing the culture supernatant of the cell culture and washing the cells with 10 mL PBS.

2) Adding prewarmed trypsin to the washed cell culture flasks, rotating culture bottle to make the bottom of the culture bottle uniformly covered by trypsin, then placed into 37° C., 5% $CO_2$ incubator to digest.

3) Suspending cells in each T150 tissue culture flask with 10-15 mL culture medium, absorbing 0.1 mL liquid and diluting 2 times by trypan blue solution as counted.

4) Diluting cells to $8 \times 10^4$ cells/mL with the culture medium, adding the diluted cells into the compound-containing 96-well plate (Greiner, Cat. #655090) (100 μL/well, 8000 cells/well) with automatic liquid separator (Thermo Scientific). Then place into a 37° C., 5% $CO_2$ incubator for 3 days. Cell control well: no compound, only containing 0.5% DMSO.

5) Adding fluorescence substrate Cell Titer-fluor to the cell well, after incubation for 30 minutes, detecting the signal by microplate reader Envison (Ex at 405 nm and read at 515 nm). The effect of the compounds on the cytotoxicity of HCV replicon cells was analyzed according to the fluorescence data, which was used to calculate the $CC_{50}$ values.

6) Then adding luciferase substrate Bright-Glo, after incubation for 5 minutes, detecting the luciferase activity by microplate reader Envison (wavelength>700 nm); analyzing the anti-HCV inhibitory activity of the compounds according to luminescence data, which was used to calculate $EC_{50}$ values.

c) Data Processing and Analysis:

The $EC_{50}$ or $CC_{50}$ values were obtained by nonlinear fitting regression on inhibition percentage (inh %) data with GraphPad Prism software.

The results of the experiments were shown in Table 1:

TABLE 1

Experimental results of $EC_{50}/CC_{50}$ of HCV replicon cells

| Embodiment | Compound ID | $EC_{50}$(1b) | $EC_{50}$(1a) | $CC_{50}$ |
| --- | --- | --- | --- | --- |
| 1 | YD_0346 | B | B | >3000 |
| 2 | YD_0273 | A | A | >3000 |
| 3 | YD_0302 | C | B | >3000 |
| 4 | YD_0303 | A | A | >3000 |
| 5 | YD_0304 | A | B | >3000 |
| 6 | YD_0305 | C | B | >3000 |
| 7 | YD_0311 | B | B | >3000 |
| 8 | YD_0313 | A | A | >3000 |
| 9 | YD_0318 | C | B | >3000 |
| 10 | YD_0322 | B | B | >3000 |
| 11 | YD_0323 | B | B | >3000 |
| 12 | YD_0324 | A | A | >3000 |
| 13 | YD_0326 | C | B | >3000 |
| 14 | YD_0340 | B | B | >3000 |
| 15 | YD_0342 | A | A | >3000 |
| 16 | YD_0343 | C | B | >3000 |
| 17 | YD_0344 | C | B | >3000 |
| 18 | YD_0345 | C | B | >3000 |
| 19 | YD_0348 | C | B | >3000 |
| 20 | YD_0349 | B | B | >3000 |
| 21 | YD_0350 | B | B | >3000 |
| 22 | YD_0352 | C | B | >3000 |
| 23 | YD_0353 | C | B | >3000 |
| 24 | YD_0355 | C | B | >3000 |
| 25 | YD_0327 | C | B | >3000 |
| 26 | YD_0329 | B | B | >3000 |
| 27 | YD_0321 | C | B | >3000 |
| 28 | YD_0325 | C | B | >3000 |
| 29 | YD_0351 | C | B | >3000 |
| 30 | YD_0019 | B | N/A | >3000 |
| 31 | YD_0044 | A | N/A | >3000 |
| 32 | YD_0056 | C | N/A | >3000 |
| 33 | YD_0057 | B | N/A | >3000 |
| 34 | YD_0058 | B | N/A | >3000 |
| 35 | YD_0059 | B | A | >3000 |
| 36 | YD_0060 | B | N/A | >3000 |
| 37 | YD_0122 | B | A | >3000 |
| 38 | YD_0214 | A | A | >3000 |
| 39 | YD_0215 | A | A | >3000 |
| 40 | YD_0216 | A | A | >3000 |
| 41 | YD_0219 | A | A | >3000 |
| 42 | YD_0245 | A | A | >3000 |
| 43 | YD_0250 | A | A | >3000 |
| 44 | YD_0253 | A | B | >3000 |
| 45 | YD_0272 | B | B | >3000 |
| 46 | YD_0278 | A | A | >3000 |
| 47 | YD_0279 | A | A | >3000 |
| 48 | YD_0280 | B | B | >3000 |
| 49 | YD_0312 | B | B | >3000 |
| 50 | YD_0317 | C | B | >3000 |
| 51 | YD_0330 | A | B | >3000 |
| 52 | YD_0331 | A | A | >3000 |
| 53 | YA_0338 | A | A | >3000 |
| 54 | YD_0356 | A | A | >3000 |
| 55 | YD_0357 | A | A | >3000 |
| 56 | YA_0358 | B | B | >3000 |
| 57 | YA_0359 | N/A | N/A | >3000 |
| 58 | YA_0360 | A | A | >3000 |

TABLE 1-continued

Experimental results of $EC_{50}/CC_{50}$ of HCV replicon cells

| Embodiment | Compound ID | $EC_{50}$(1b) | $EC_{50}$(1a) | $CC_{50}$ |
|---|---|---|---|---|
| 59 | YA_0361 | N/A | N/A | >3000 |
| 60 | YA_0362 | N/A | N/A | >3000 |
| 61 | YA_0363 | A | A | >3000 |
| 62 | YD_0365 | A | A | >3000 |
| 63 | YA_0366 | A | A | >3000 |
| 64 | YA_0367 | A | A | >3000 |
| 65 | YA_0368 | B | A | >3000 |
| 66 | YH_0369 | C | B | >3000 |
| 67 | YH_0373 | A | A | >3000 |
| 68 | YD_0374 | A | A | >3000 |

Note:
A (0.1 nM-100 nM); B (100.01 nM-1000 nM); C (1000.01 nM-5000 nM).
Conclusion: the compounds of the present invention have excellent anti-HCV activity in vitro.

What is claimed is:

1. A compound of formula (I) or a pharmaceutically acceptable salt thereof,

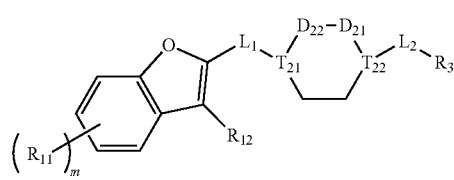

wherein,
$L_1$ is —C(═O)—;
the moiety

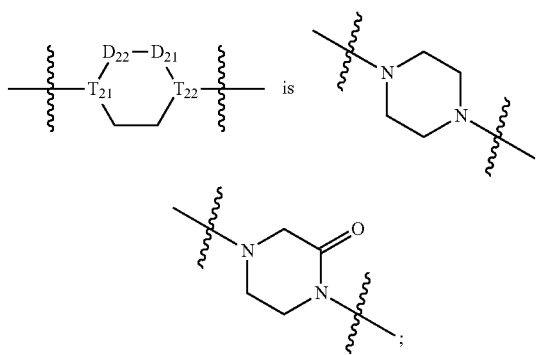

$L_2$ is a bond;
$R_3$ is selected from the group consisting of

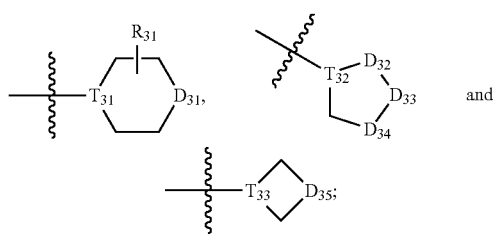

each of $T_{31-33}$ is N;

each of $D_{31-35}$ is dependently selected from the group consisting of —[C($R_{d1}$)($R_{d2}$)]$_{0-2}$—, —C(═O)—, —C(═O)N($R_{d3}$)—, —N($R_{d4}$)—, —C(═N$R_{d5}$)—, —S(═O)$_2$N($R_{d6}$)—, —S(═O)N($R_{d7}$)—, —O—, —S—, —C(═O)O—, —C(═S)—, —S(═O)— and —S(═O)$_2$—;

$R_{31}$ is selected from the group consisting of H, F, Cl, Br, I, CN, OH, SH, NH$_2$, CHO, COOH, and C(═O)NH$_2$, or selected from the group consisting of a $C_{1-10}$ alkyl or heteroalkyl optionally substituted by $R_{01}$, a $C_{3-10}$ cyclohydrocarbyl, a $C_{1-10}$ alkyl or heteroalkyl substituted by a $C_{3-10}$ cyclohydrocarbyl;

or, there is another linking bond $(CH_2)_{1-3}$ between $T_{31}$ and $D_{31}$, $D_{33}$ and $D_{34}$, $T_{33}$ and $D_{35}$;

each of $R_{11-12}$, $R_{d1}$, $R_{d2}$ is independently selected from the group consisting of H, F, Cl, Br, I, CN, OH, SH, NH$_2$, CHO, COOH, C(═O)NH$_2$, or selected from the group, optionally substituted by none, one, two or three of $R_{01}$, consisting of a $C_{1-10}$ alkyl or heteroalkyl, a $C_{3-10}$ cyclohydrocarbyl, a $C_{1-10}$ alkyl or heteroalkyl substituted by a $C_{3-10}$ cyclohydrocarbyl;

$R_{01}$ is selected from the group consisting of F, Cl, Br, I, CN, OH, SH, NH$_2$, and $R_{02}$;

$R_{02}$ is selected from the group consisting of a $C_{1-10}$ alkyl, a $C_{1-10}$ alkylamino, a alkyl)amino, a $C_{1-10}$ alkoxyl, a $C_{1-10}$ alkanoyl, a $C_{1-10}$ alkoxycarbonyl, a $C_{1-10}$ alkylsulfonyl, a $C_{1-10}$ alkylsulfinyl, a $C_{3-10}$ cycloalkyl, a $C_{3-10}$ cycloalkylamino, a $C_{3-10}$ heterocycloalkylamino, a $C_{3-10}$ cycloalkoxyl, a $C_{3-10}$ cycloalkanoyl, a $C_{3-10}$ cycloalkoxycarbonyl, a $C_{3-10}$ cycloalkylsulfonyl, and a $C_{3-10}$ cycloalkylsulfinyl;

the "hetero" represents a heteroatom or a heteroatomic group, which is selected from the group consisting of —C(═O)N($R_{d3}$)—, —N($R_{d4}$)—, —C(═N$R_{d5}$)—, —S(═O)$_2$N($R_{d6}$)$^-$, —S(═O)N($R_{d7}$)—, —O—, —S—, —C(═O)O—, —C(═O)—, —C(═S)—, —S(═O)—, —S(═O)$_2$— and —N($R_{d8}$)C(═O)N($R_{d9}$)—;

each of $R_{d3-d9}$ is independently selected from the group consisting of H, OH, NH$_2$, and $R_{02}$;

$R_{02}$ is optionally substituted by $R_{001}$;

$R_{001}$ is selected from the group consisting of F, Cl, Br, I, CN, OH, N(CH$_3$)$_2$, NH(CH$_3$), NH$_2$, CHO, COOH, C(═O)NH$_2$, trihalomethyl, dihalomethyl, monohalomethyl, aminomethyl, hydroxymethyl, methyl, methylamino, formyl, methoxycarbonyl, methylsulfonyl, and methylsulfinyl;

the number of $R_{01}$, $R_{001}$, the heteroatom or the heteroatomic group is independently selected from the group consisting of 0, 1, 2 and 3.

2. The compound or the pharmaceutically acceptable salt thereof according to claim 1, wherein the moiety

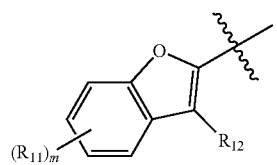

is selected from

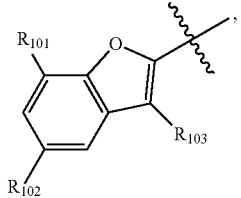

each of $R_{101-103}$ is independently selected from the group consisting of H, F, Cl, Br, I, CN, OH, SH, $NH_2$, CHO, COOH, $C(=O)NH_2$, or selected from the group, optionally substituted by none, one, two or three of $R_{01}$, consisting of a $C_{1-10}$ alkyl or heteroalkyl, a $C_{3-10}$ cyclohydrocarbyl, and a $C_{1-10}$ alkyl or heteroalkyl substituted by a $C_{3-10}$ cyclohydrocarbyl, $R_{01}$ is defined as claim 1.

3. The compound or the pharmaceutically acceptable salt thereof according to claim 2, wherein each of $R_{101-103}$ is independently selected from the group consisting of F, Cl, Br, $-CF_3$, $-CHF_2$, CN, Me, ethyl, propyl, cyclopropyl and iso-propyl.

4. The compound or the pharmaceutically acceptable salt thereof according to claim 2, wherein the moiety

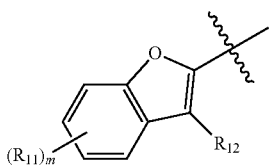

is selected from the group consisting of

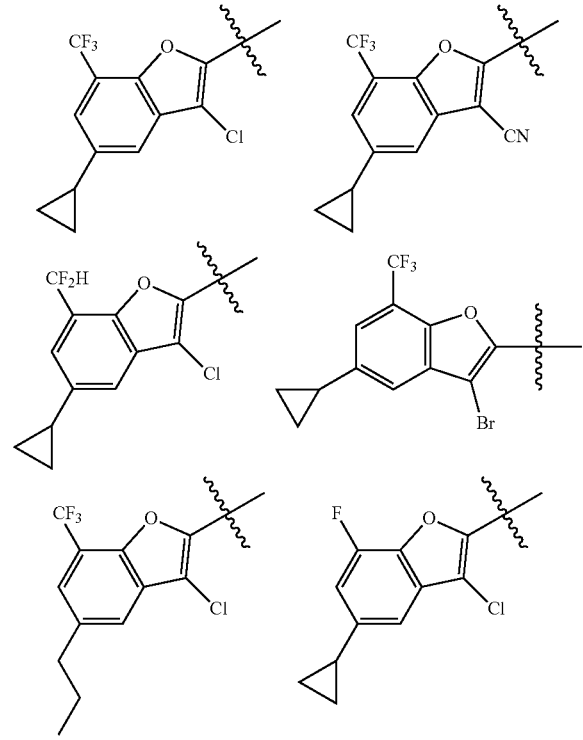

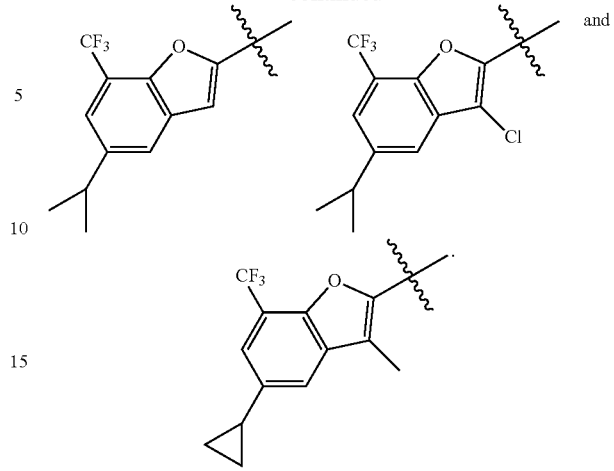

5. The compound or the pharmaceutically acceptable salt thereof according to claim 1, wherein each of $D_{31-35}$ is dependently selected from the group consisting of $-C(=O)-$, $-O-$, methylene, $-N(CH_3)-$, $-CH(OH)-$, and $-CF_2-$; $R_{31}$ is selected from the group consisting of H, methyl, ethyl, n-propyl, and iso-propyl.

6. The compound or the pharmaceutically acceptable salt thereof according to claim 1, wherein $R_3$ is selected from the group consisting of

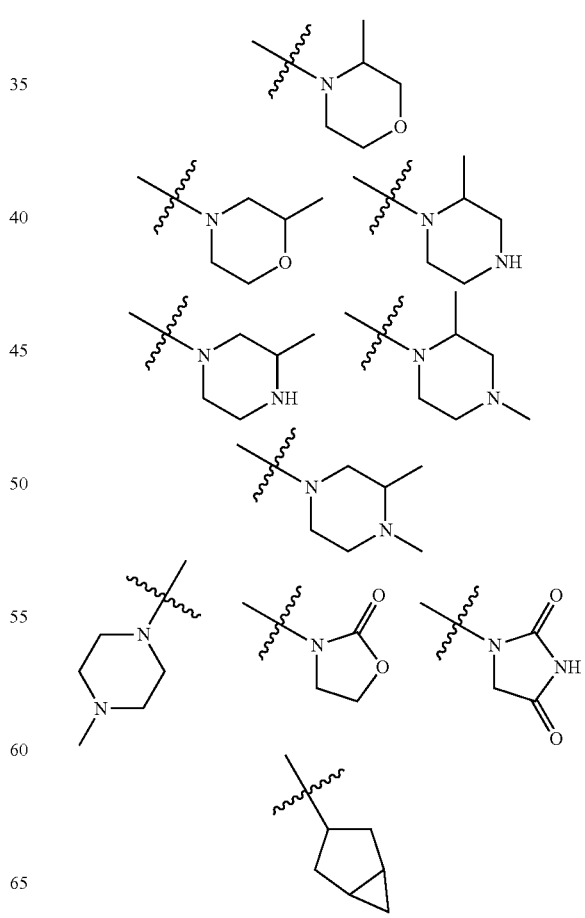

-continued
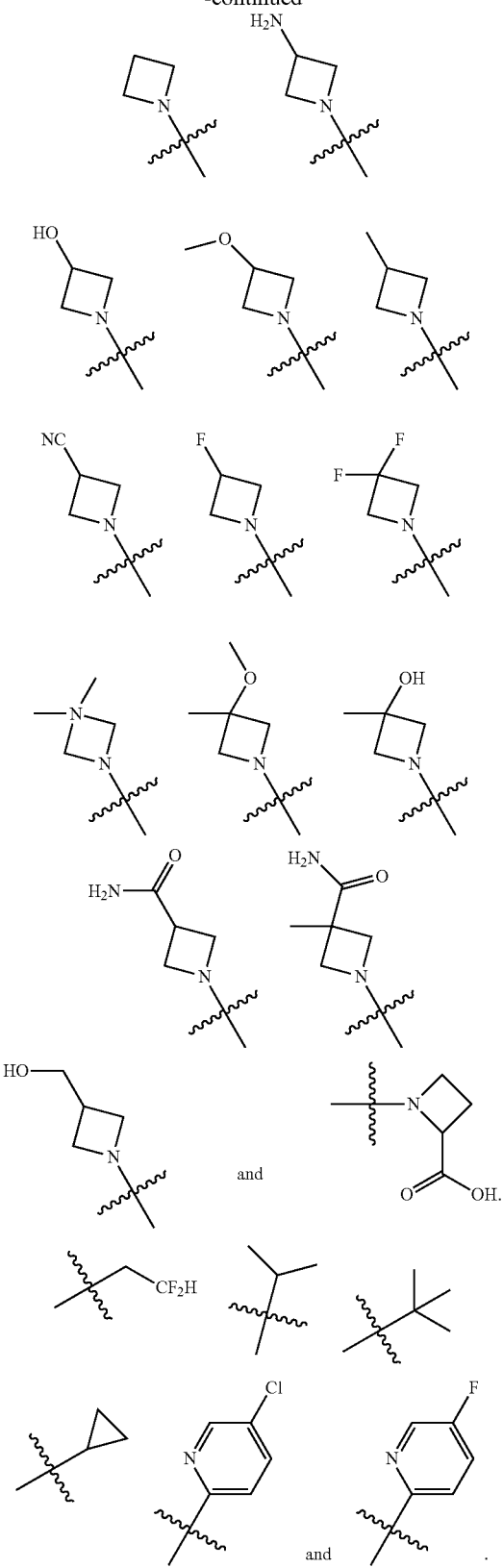
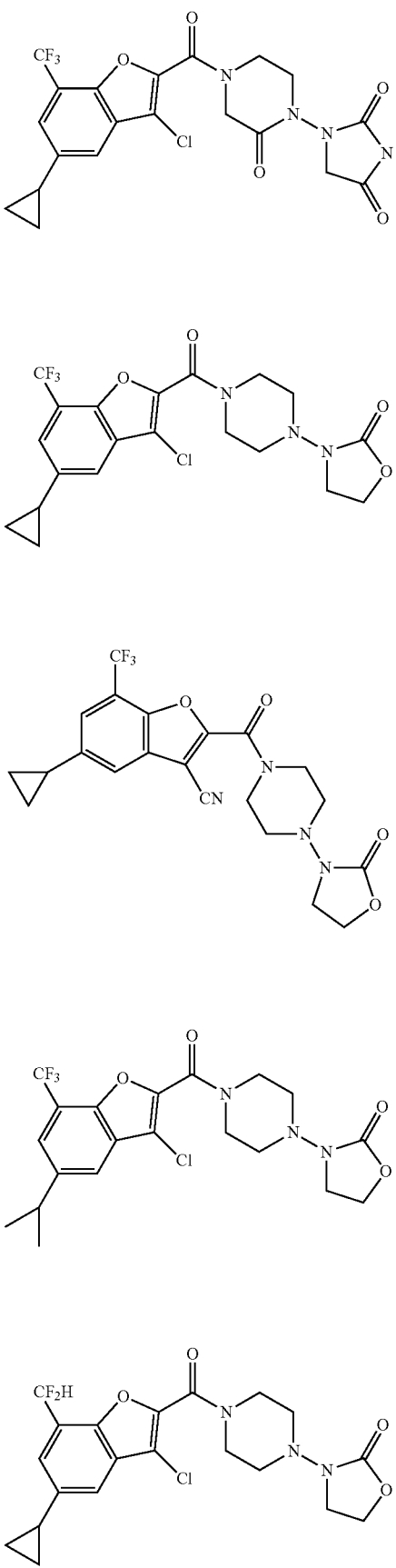
7. The compound or the pharmaceutically acceptable salt thereof according to claim 1, which is selected from the group consisting of

143
-continued
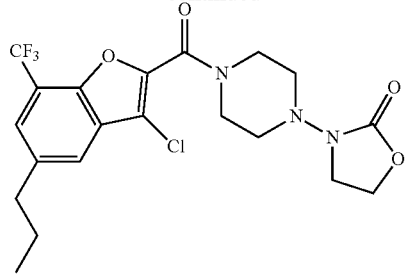
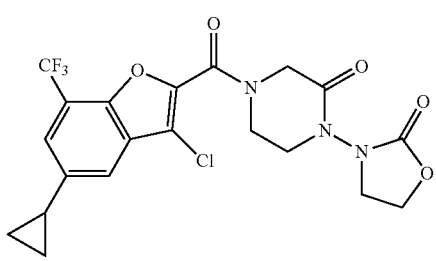
144
-continued
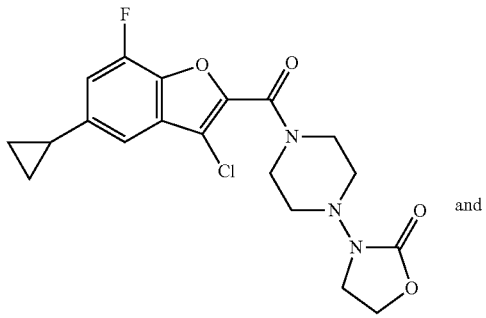
and
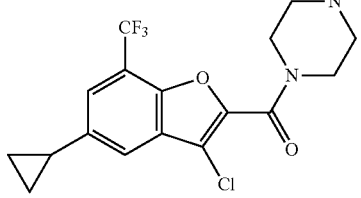
* * * * *